(12) United States Patent
Labrie et al.

(10) Patent No.: US 8,735,080 B2
(45) Date of Patent: May 27, 2014

(54) METHODS AND DEVICES FOR DETECTING OBSTRUCTIVE UROPATHY AND ASSOCIATED DISORDERS

(75) Inventors: Samuel T. Labrie, Austin, TX (US); James P. Mapes, Lakeway, TX (US); Ralph L. McDade, Austin, TX (US); Dominic Eisinger, Keene, NY (US); Karri L. Ballard, Austin, TX (US); Michael D. Spain, Austin, TX (US)

(73) Assignee: Rules-Based Medicine, Inc., Austin, TX (US)

( * ) Notice: Subject to any disclaimer, the term of this patent is extended or adjusted under 35 U.S.C. 154(b) by 95 days.

(21) Appl. No.: 12/852,236

(22) Filed: Aug. 6, 2010

(65) Prior Publication Data

US 2011/0065137 A1 Mar. 17, 2011

Related U.S. Application Data

(60) Provisional application No. 61/327,389, filed on Apr. 23, 2010, provisional application No. 61/232,091, filed on Aug. 7, 2009.

(51) Int. Cl.
*G01N 33/53* (2006.01)

(52) U.S. Cl.
USPC .............................. 435/7.1; 435/7.2

(58) Field of Classification Search
None
See application file for complete search history.

(56) References Cited

U.S. PATENT DOCUMENTS

| | | | |
|---|---|---|---|
| 7,235,358 B2 | 6/2007 | Wolgemuth et al. | |
| 7,560,244 B2 | 7/2009 | Krolewski | |
| 2003/0199000 A1 | 10/2003 | Virkirs et al. | |
| 2006/0008804 A1* | 1/2006 | Chibout et al. | 435/6 |
| 2006/0269949 A1 | 11/2006 | Halloran et al. | |
| 2007/0087387 A1 | 4/2007 | Devarajan | |
| 2007/0087448 A1 | 4/2007 | Nelsestuen et al. | |
| 2007/0124086 A1 | 5/2007 | Mendrick et al. | |
| 2007/0248989 A1 | 10/2007 | Devarajan et al. | |
| 2007/0287188 A1 | 12/2007 | Hu et al. | |
| 2008/0090304 A1 | 4/2008 | Barasch et al. | |
| 2008/0153092 A1 | 6/2008 | Kienle et al. | |
| 2008/0318803 A1 | 12/2008 | Jain et al. | |
| 2009/0081713 A1 | 3/2009 | Klein et al. | |
| 2009/0093010 A1 | 4/2009 | Nickerson et al. | |
| 2009/0176217 A1 | 7/2009 | Sella-Tavor et al. | |
| 2009/0197287 A1 | 8/2009 | Hu et al. | |
| 2010/0035263 A1 | 2/2010 | Dihazi et al. | |
| 2010/0125288 A1 | 5/2010 | Gelfand | |
| 2010/0143956 A1 | 6/2010 | Maurer et al. | |
| 2011/0117583 A1 | 5/2011 | Hoffmann et al. | |

FOREIGN PATENT DOCUMENTS

| | | |
|---|---|---|
| WO | WO 2004030521 | 4/2004 |
| WO | WO2004042346 | 5/2004 |
| WO | WO 2006083986 | 2/2006 |
| WO | WO 2006066587 | 6/2006 |
| WO | WO 2007000466 | 1/2007 |
| WO | WO 2007121922 | 11/2007 |
| WO | WO 2007138011 | 12/2007 |
| WO | WO 2008109797 | 3/2008 |
| WO | WO 2008109797 | 6/2008 |
| WO | WO 2008116867 | 10/2008 |
| WO | WO 2008128043 | 10/2008 |
| WO | WO 2008154238 | 12/2008 |
| WO | WO 2010022210 | 8/2009 |

OTHER PUBLICATIONS

Dziukas et al., Renal localization of Tamm-horsfall protein in unilateral obstructive uropathy in rats, Lab Invest. (Aug. 1982), vol. 47, No. 2, pp. 185-193.; abstract only.
Devarajan et al., Neutrophil gelatinase-associated lipocalin (NGAL): A new marker of kidney disease. Scand J Clin Lab Invest Suppl. 2008, vol. 241, pp. 89-94.
Freedman et al., Use of Urinary Beta-2-Microglobulin to Predict Severe Renal Damage in Fetal Obstructive Uropathy, Fetal Diagn Ther, Jan.-Feb. 1997, vol. 12, No. 1, pp. 1-6; abstract only.
Mussap et al., Predictive value of amniotic fluid cystatin C levels for the early identification of fetuses with obstructive uropathies, BJOG: an International Journal of Obstetrics and Gynaecology Jul. 2002, vol. 109, pp. 778-783; abstract.
Eddy, Molecular basis of renal fibrosis, Pediatr Nephrol (2000), vol. 15, pp. 290-301.
Hepfer, et al., Development and Validation of a Multi-Analyte Profile (MAP) of Putative Biomarkers of Human Kidney Damage, http://www.rulesbasedmedicine.com/scientific-literature/abstracts-posters.aspx, Mar. 13, 2009.
Ferguson et al., Biomarkers of nephrotoxic acute kidney, Toxicology, vol. 245 pp. 182-193 (2008).
Trof et al., "Biomarkers of Acute Renal Injury and Renal Failure." Shock [online], Sep. 2006 [Retrieved on Sep. 29, 2010], vol. 26, No. 3, pp. 245-253, Retrieved from the Internet: <URL: http://journals.www.com/shockjournal/Fulltext/2006/09000/Biomarkers_of_Acute_Renal_Injury_and_Renal_Failure.4.aspx>.
Liao et al., High-throughput miniaturized immunoassay for human interleukin-6 using electrochemical sandwich-type enzyme immunosensors. Current Pharmaceutical Analysis, May 2009, vol. 5, No. 2, pp. 164-170; abstract.
Everaert et al., A review on urinary proteins in outflow disease of the upper urinary tract. Clinica Chimica Acta, Jul. 2000, vol. 297, No. 1-2, pp. 183-189; abstract.
Huang et al., Assessment of Cisplatin-Induced Nephrotoxicity by Microarray Technology. Toxicological Sciences, Oct. 2001, vol. 63, No. 2, pp. 196-207; abstract.
Bruning et al., Pathological Excretion Patterns of Urinary Proteins in Miners Highly Exposed to Dinitrotoluene. Jul. 2001, vol. 43, No. 7, pp. 610-615; abstract.

(Continued)

*Primary Examiner* — Jacob Cheu
(74) *Attorney, Agent, or Firm* — Myriad Genetics, Inc.

(57) ABSTRACT

Methods and devices for diagnosing, monitoring, or determining obstructive uropathy or an associated disorder in a mammal are described. In particular, methods and devices for diagnosing, monitoring, or determining obstructive uropathy or an associated disorder using measured concentrations of a combination of three or more analytes in a test sample taken from the mammal are described.

22 Claims, 36 Drawing Sheets

(56) References Cited

OTHER PUBLICATIONS

Penders et al., Alpha-1 microglobulin: clinical laboratory aspects and applications. Clinica Chimica Acta, Aug. 16, 2004, vol. 346, No. 2, pp. 107-118; abstract.

Torffivit et al., Tubular Secretion of Tamm-Horsfall Protein Is Decreased in Type 1 (Insulin-Dependent) Diabetic Patients with Diabetic Nephropathy. Nephron, 1993, vol. 65, pp. 227-231; abstract.

Malyszko et al., Resistin, a new adipokine, is related to inflammation and renal function in kidney allograft recipients. Transplantation proceedings, 2006, vol. 38, Issue 10, pp. 3434-3436; abstract.

Eng et al., Chronic angiotensin-converting enzyme inhibition up-regulates mouse kidney growth arrest specific-6 protein and the AXL subfamily of receptor tyrosine kinases. Journal of Renin-Angiotensin-Aldosterone System, Dec. 2008, vol. 9, No. 4, pp. 238-241; p. 238.

Kerby et al., Immunolocalization of Fgf-1 and receptors in glomerular lesions associated with chronic human renal allograft rejection 1. Transplantation. Jul. 27, 1996, vol. 62, No. 2. pp. 190-200; abstract.

D'Amico et al., Urinary protein and enzyme excretion as markers of tubular damage. Current Opinion in Nephrology and Hypertension, Nov. 2003, vol. 12, No. 6, pp. 639-643; abstract.

Sanders et al., Renal expression of matrix metalloproteinases in human ANCA-associated glomerulonephritis. Nephrol dial. Transplant. Jun. 2004, vol. 19, No. 6, pp. 1412-1419; abstract.

Yu et al., IL-1 up regulates osteopontin expression in experimental crescentic glomerulonephritis in the rat, American Journal of Pathology, Mar. 1999, vol. 154, No. 3, pp. 833-841; abstract.

Kuwabara et al., "Urinary Neutrophil gelatinase-associated lipocalin levels reflect damage to glomeruli, proximal tubules, and distal nephrons" by Kuwabara et al. Kidney Internal 75: 285-294 (Feb. 2009; published online Oct. 1, 2008). p. 285.

Vaidya, V.S. et al., Biomarkers of Acute Kidney Injury. Annu. Rev. Pharmacol. Toxicol. Oct. 15, 2007, vol. 48, pp. 463-493.

Yu, M. et al., Clinical Significance of Determination of Urinary Albumin, Beta 2 Microglobulin and Tamm-Horsfall Protein in Diabetics. Zhonghua Nei Ke Za Zhi. Jun. 1991, vol. 30(6), pp. 354-356, 383: abstract.

Thomson, S.E. et al., Renal Connective Tissue Growth Factor Correlates with Glomerular Basement Membrane Thickness and Prospective Albuminuria in a Non-Human Primate Model of Diabetes: Possible Predictive Marker for Incipient Diabetic Nephropathy. Journal of Diabetes and Its Complications . Apr. 16, 2008, vol. 22(4), pp. 284-294: abstract.

Kim, N.H. et al., Plasma and Urinary Vascular Endothelial Growth Factor and Diabetic Nephropathy in Type 2 Diabetes Mellitus. Jun. 2004, vol. 21(6), pp. 545-551: abstract.

Hu, Y. et al., Functional Annotations of Diabetes Nephropathy Susceptibility Loci through Analysis of Genome-Wide Renal Gene Expression in Rat Models of Diabetes Mellitus. Jul. 9, 2009, vol. 2:41, pp. 1-12.

Peng et al., Prediction of subclinical renal allograft rejection by vascular endothelial growth factor in serum and urine J. Nephrol. Jul.-Aug. 2008, vol. 21, No. 4, pp. 535-542.

Simonson et al., Elevated neointimal endothelin-1 in transplantation-associated arteriosclerosis of renal allograft recipients. Kidney Int. Sep. 1998, vol. 53, No. 3, pp. 960-971.

Li et al., Interference of globin genes with biomarker discovery for allograft rejection in peripheral blood samples. Physiol. Genomics. Jan. 17, 2008, vol. 32, No. 2, pp. 190-197.

Kim et al., Urinary HLA-DR and CD54 expression—indicators for inflammatory activity in decoy cell shedding patients. Nephrol. Dial. Transplant. Sep. 2006, vol. 21, No. 9, pp. 2601-2606.

Boonstra et al., Expression and function of Fas (CD95) on human renal tubular epithelial cells. J. Am. Soc. Nephrol. Oct. 1997, vol. 8, No. 10, pp. 1517-1524.

Nossel et al., The generation of fibrinopeptide A in clinical blood samples: evidence for thrombin activity. J. Clin. Invest. Nov. 1976, vol. 58, No. 5, pp. 1136-1144.

Sererger et al., The Duffy antigen receptor for chemokines is up-regulated during acute renal transplant rejection and crescentic glomerulonephritis. Kidney Int. Oct. 2000, vol. 58, No. 4, pp. 1546-1556.

Clarke et al., Characterization of renal allograft rejection by urinary proteomic analysis. Ann. Surg. May 2003, vol. 237, No. 5, pp. 660-665.

Anglicheau et al., MicroRNA expression profiles predictive of human renal allograft status. Proc. Natl. Acad. Sci. USA. Mar. 31, 2009, vol. 106, No. 13, pp. 5330-5335.

Rodrigo et al., Circulating levels of matrix metalloproteinases MMP-3 and MMP-2 in renal transplant rebipients with chronic transplant nephropathy. Nephrol. Dial. Transplant. Dec. 2000, vol. 15, No. 12, pp. 2041-2045.

Benkali et al., A new strategy for faster urinary biomarkers identification by Nano-LC-MALDI-TOF/TOF mass spectrometry. BMC Genomics. Nov. 14, 2008, vol. 9, No. 541, pp. 1-9.

Schiffer et al., B-cell-attracting chemokine CXCL13 as a marker of disease activity and renal involvement in systemic lupus erythematosus (SLE); Nephrol Dial Transplant, vol. 24, pp. 3708-3712, 2007.

Kosmaczewska et al. CD40L, CD28, and CTLA-4 Expression on CD4+ T cells in kidney graft recipients: A relationship with post-transplantation clinical course; Transplant Immunology, vol. 16, pp. 32-40, 2006.

Ferreira et al., Effect of type of dialysis membrane on bone in haemodialysis patients; Nephrol Dial Transplant, vol. 16, pp. 1230-1238, 2001.

Perez-Fontan et al., Short-term regulation of peptide YY secretion by a mixed meal of peritoneal glucose-based dialysate in patients with chronic renal failure; Nephrol Dial Transplant, vol. 23, pp. 2696-3703, 2008.

El Kossi et al. Stem Cell Factor and crescentic glomerulonephritis; American J Kidney Diseases, vol. 41, No. 4, pp. 785-795, 2003.

Liu et al., Predictive and pathogenic value of plasma biomarkers for acute kidney injury in patients with acute lung injury; Crit Care Med, vol. 35, No. 12, 27-55-2761, 2007.

Yin et al. Expression of growth arrest-specific gene 6 and its receptors in dysfunctional human renal allografts; Transplant Int, vol. 16, No. 9, pp. 681-688, 2003.

Collins et al., The application of genomic and proteomic technologies in predictive, preventative and personalized medicine; Vascular Pharmacology, vol. 45, No. 5, pp. 258-267, 2006.

Hong, Markers of Diabetic Nephropathy, Journal of Diabetes and Its Complications, 12:43-60, 1998.

Rysz, Serum matric metalloproteinases MMP-2 and MMP-9 and metalloproteinase tissue inhibitors TIMP-1 and TIMP-2 in diabetic nephropathy (Abstract only), Journal of Nephrology, 20(4), 444-452, 2007.

Asami T et al., "Study on the relation between renal tubular disorders and glomerular dysfunction in the early phase of insulin-dependent diabetes mellitus in children.", Nihon Jinzo Gakkai Shi, vol. 34, No. 1, pp. 57-63, 1992. Abstract only.

Aoki et al., "Contribution of hyperglycemia and renal damage to urinary C-peptide clearance in non-insulin-dependent diabetic patients", Diabetes Res Clin Pract. vol. 14, No. 2, pp. 85-89, 1991.

Asami T et al., "Study on the relation between renal tubular disorders and glomerular dysfunction in the early phase of insulin-dependent diabetes mellitus in children.", Nihon Jinzo Gakkai Shi, vol. 34, No. 1, pp. 57-63, Abstract only, 1992.

Bao et al., "A Novel Accurate Rapid ELISA for Detection of Urinary Connective Tissue Growth Factor, a Biomarker of Chronic Allograft Nephropathy." Transplant Proc. vol. 40, No. 7, pp. 2361-2364, 2008.

Bauvois et al. (Nephrol Dial Transplant, 2007, 22(4): 1115-1122).

Gillespie A et al: "Biomarkers in renal transplantation", Biomarkers in Medicine 2008 GB, vol. 2, No. 6, 2008, pp. 603-612, XP008158885, ISSN: 1752-0363.

Han et al. (Kidney, 2002, 62(1): 237-244).

Hedberg et al.: "Analysis of kidney biomarkers in plasma and urine from patients with renal injury", Society of Toxicology Annual Meeting, Feb. 15, 2010, XP055047050.

Hedberg et al. : "Analysis of kidney biomarkers in plasma and urine from patients with renal injury", Internet Citation, Mar. 5, 2010,

(56) References Cited

OTHER PUBLICATIONS

XP002688772, Retrieved from the Internet: URL: http://www.myriadrbm.com/docs/sot2010-hedberg-poster.pdf [retrieved on Dec. 6, 2012].
Hepfer et al. (Development of a Multi-Analyate Profile (MAP) of Putative Biomarkers of Human Kidney Damage, 2009, http://www.rulesbasedmedicine.com/scientific-literature/abstracts-posters.aspx).
Horstrup et al. (Neophrol Dial Transplant, 2002, 17: 1005-1013).
Kanauchi et al., "Glomerular Lesions in Patients with Non-Insulin-Dependent Diabetes Mellitus and Microalbuminuria", Internal Medicine, vol. 32, No. 10, pp. 753-757, Oct. 1993.
Kusters S et al., "Development and validation of a multi-analyte profile (MAP) of putative biomarkers of human kidney damage", Toxicology Letters, Elsevier Biomedical Press, vol. 189, Sep. 13, 2009.
Lervang et al., "Does increased glomerular filtration rate or disturbed tubular function early in the course of childhood type 1 diabetes predict the development of nephropathy?" Diabet Med., vol. 9, No. 7, pp. 635-640, Aug.-Sep. 1992. Abstract.
Liangos et al., "Comparative Analysis of Urinary Biomarkers for Early Detection of Acute Kidney Injury Following Cardiopulmonary Bypass." Biomarkers, vol. 14, No. 6, pp. 423-431, 2009.
Miyake H et al., "Urinary laminin P1 as an index of glycemic control in children with insulin-dependent diabetes mellitus." Diabetes Res., vol. 23, No. 3, pp. 131-138, 1993. Abstract.
Mocan Z et al., "Urinary beta 2-microglobulin levels and urinary N-acetyl-beta-D-glucosaminidase enzyme activities in early diagnosis of non-insulin-dependent diabetes mellitus nephropathy." Diabetes Res., vol. 26, No. 3, pp. 101-107, 1994. Abstract.
Mutti et al., "Urinary excretion of brush-border antigen and plasma proteins in early stages of diabetic nephropathy." Clin Chim Acta., vol. 188, No. 2, pp. 93-100, Apr. 30, 1990. Abstract.
Neri S et al., "[Plasma beta 2-microglobulin in patients with non-insulin-dependent diabetes mellitus]." Minerva Med., vol. 86, No. 1-2, pp. 11-5, Jan.-Feb. 1995. Abstract.
Scherberich et al (Klin Wochenschr, 1989, 67 Suppl 17: Abstract).
Sejdiu et al. (Scand J Urol Nephrol, 2008, 42(2): 168-174).
Serafini-Cessi et al., "Tamm-Horsfall Glycoprotein: Biology and Clinical Relevance." Amer J Kidney Diseases, vol. 42, No. 4, pp. 658-676, 2003.
Shimizu H et al., "Changes in urinary retinol binding protein excretion and other indices of renal tubular damage in patients with non-insulin dependent diabetes," Diabetes Res Clin Pract., vol. 18, No. 3, pp. 207-210, 1992. Abstract.
Sitjar de Togores et al., "[Urinary excretion of N-acetyl-beta-D-glucosaminidase and macroglobulin 2 in type I diabetes mellitus]." An Esp Pediatr. vol. 34, No. 3, pp. 225-229, Mar. 1991. Abstract.
Stehouwer CD et al., "Diurnal variation in urinary protein excretion in diabetic nephropathy." Nephrol Dial Transplant., vol. 6, No. 4, pp. 238-243, 1991. Abstract.
Stiegler H et al., "Morbidity, mortality, and albuminuria in type 2 diabetic patients: a three-year prospective study of a random cohort in general practice." Diabet Med., vol. 9, No. 7, pp. 646-653, Aug.-Sep. 1992. Abstract.
Thongboonkerd, V. et al., Proteomic Identification and Immunolocalization of Increased Renal Calbindin-D28k Expression in OVE26 Diabetic Mice. The Review of Diabetic Studies. May 2005, vol. 2(1), pp. 19-26: abstract.
Tockman et al. (Cancer Res., 1992, 52: 2711s-2718s).
Tsai et al (Nephron, 2000, 85(3): 207-214).
Uwe Poge et al: "Time course of low molecular weight proteins in the early kidney transplantation period—influence of corticosteroids", Nephrology Dialysis Transplantation, vol. 19, No. 11, Sep. 22, 2004, pp. 2858-2863, XP055048192, DOI: 10.1093/ndt/gfh341.
Watts GF et al., "Low-molecular-weight proteinuria in insulin-dependent diabetes mellitus: a study of the urinary excretion of beta 2-microglobulin and retinol-binding protein in alkalinized patients with and without microalbuminuria." Diabetes Res. vol. 12, No. 1, pp. 31-36, Sep. 1989. Abstract.
Yu JY et al., "[Clinical observation on diabetic nephropathy treated with alcohol of *Abelmoschus manihot*]." Zhongguo Zhong Xi Yi Jie He Za Zhi, vol. 15, No. 5, pp. 263-265, May 1995. Abstract.

\* cited by examiner

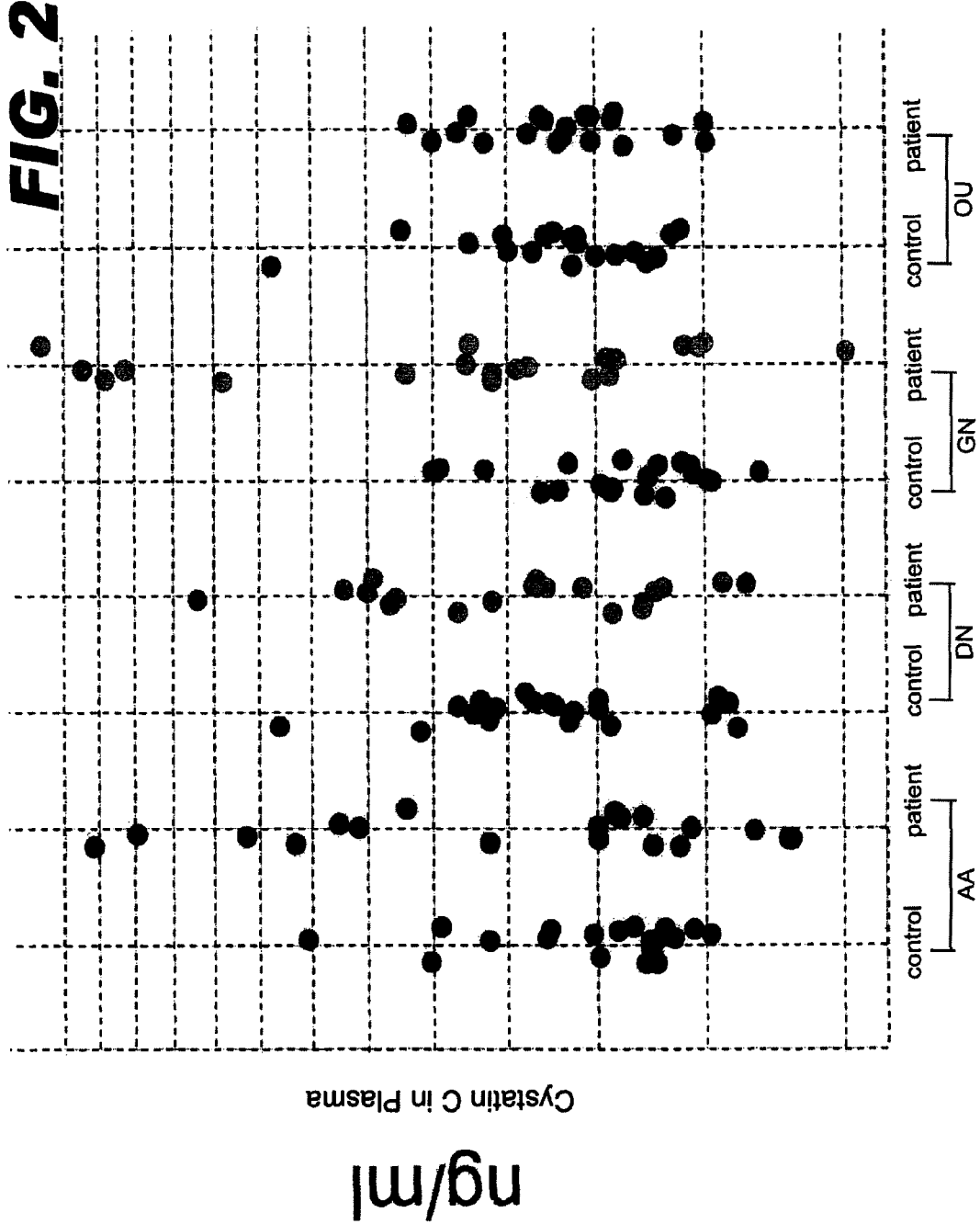

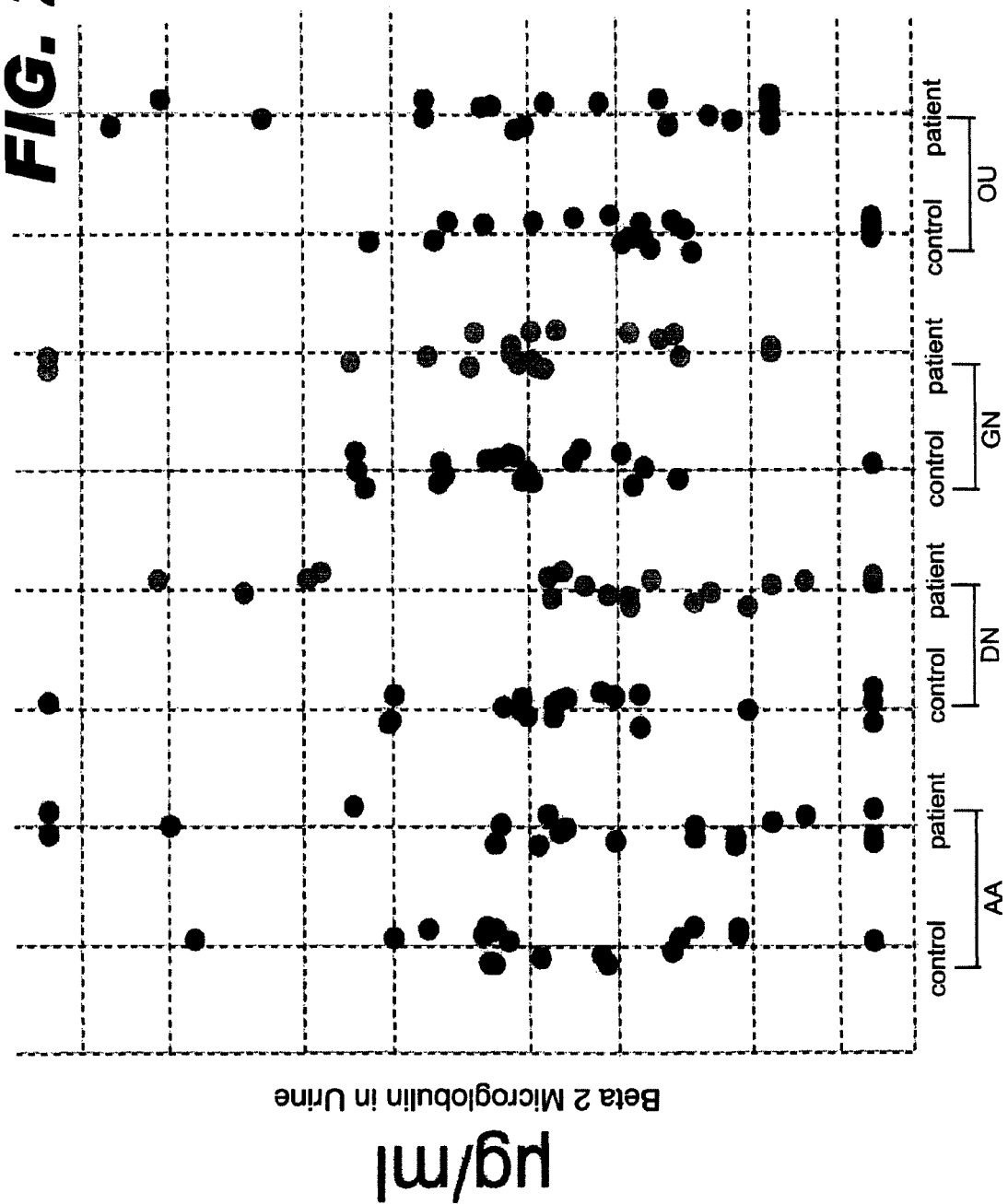

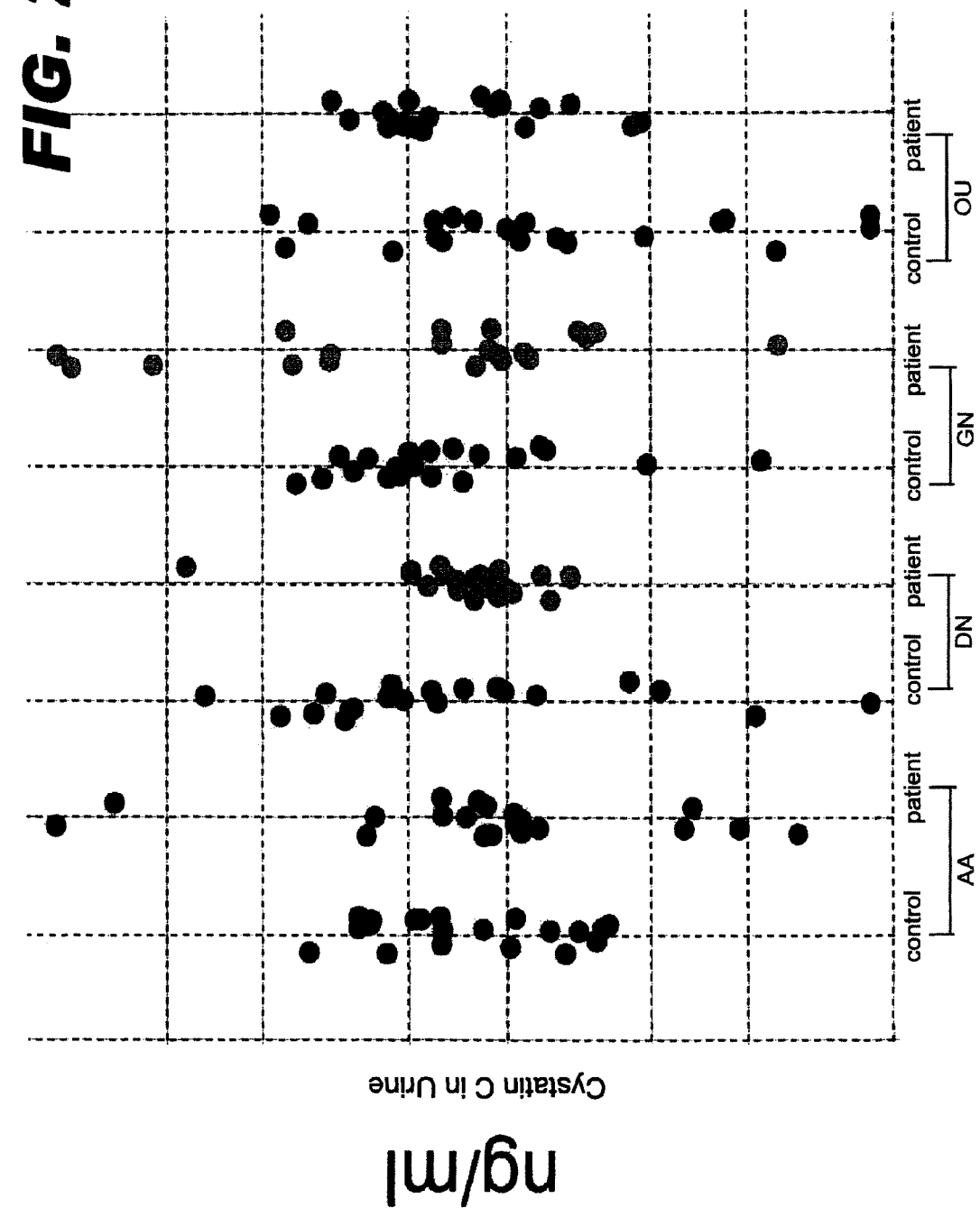

METHODS AND DEVICES FOR DETECTING OBSTRUCTIVE UROPATHY AND ASSOCIATED DISORDERS

CROSS REFERENCE TO RELATED APPLICATIONS

This application claims the priority of U.S. provisional application Ser. No. 61/327,389, filed Apr. 23, 2010, and U.S. provisional application Ser. No. 61/232,091, filed Aug. 7, 2009, each of which is hereby incorporated by reference in its entirety and is related to U.S. patent application Ser. Nos. 12/852,202, 12/852,152, 12/852,295, 12/852,312, 12/852,322, 12/852,282, entitled Computer Methods and Devices for Detecting Kidney Damage, Methods and Devices for Detecting Glomerulonephritis and Associated Disorders, Methods and Devices for Detecting Kidney Damage, Devices for Detecting Renal Disorders, Methods and Devices for Detecting Kidney Transplant Rejection, Methods and Devices for Detecting Diabetic Nephropathy and Associated Disorders, filed on the same date as this application, the entire contents of which are incorporated herein by reference.

FIELD OF THE INVENTION

The invention encompasses methods and devices for diagnosing, monitoring, or determining obstructive uropathy or an associated disorder in a mammal. In particular, the present invention provides methods and devices for diagnosing, monitoring, or determining obstructive uropathy or an associated disorder using measured concentrations of a combination of three or more analytes in a test sample taken from the mammal.

BACKGROUND OF THE INVENTION

The urinary system, in particular the kidneys, perform several critical functions such as maintaining electrolyte balance and eliminating toxins from the bloodstream. In the human body, the pair of kidneys together process roughly 20% of the total cardiac output, amounting to about 1 L/min in a 70-kg adult male. Because compounds in circulation are concentrated in the kidney up to 1000-fold relative to the plasma concentration, the kidney is especially vulnerable to injury due to exposure to toxic compounds.

An obstruction causing the flow of urine to back up into the kidneys can cause permanent damage to the kidneys, and may result in renal failure. Existing diagnostic tests such as BUN and serum creatine tests typically detect only advanced stages of kidney damage. Other diagnostic tests such as kidney tissue biopsies or CAT scans have the advantage of enhanced sensitivity to earlier stages of kidney damage, but these tests are also generally costly, slow, and/or invasive.

A need exists in the art for a fast, simple, reliable, and sensitive method of detecting obstructive uropathy or an associated disorder. In a clinical setting, the early detection of kidney damage would help medical practitioners to diagnose and treat kidney damage more quickly and effectively.

SUMMARY OF THE INVENTION

The present invention provides methods and devices for diagnosing, monitoring, or determining a renal disorder in a mammal. In particular, the present invention provides methods and devices for diagnosing, monitoring, or determining a renal disorder using measured concentrations of a combination of three or more analytes in a test sample taken from the mammal.

One aspect of the invention encompasses a method for diagnosing, monitoring, or determining obstructive uropathy or an associated disorder in a mammal. The method typically comprises providing a test sample comprising a sample of bodily fluid taken from the mammal. Then, the method comprises determining a combination of sample concentrations for three or more sample analytes in the test sample, wherein the sample analytes are selected from the group consisting of alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF. The combination of sample concentrations may be compared to a data set comprising at least one entry, wherein each entry of the data set comprises a list comprising three or more minimum diagnostic concentrations indicative of obstructive uropathy or an associated disorder. Each minimum diagnostic concentration comprises a maximum of a range of analyte concentrations for a healthy mammal. Next, the method comprises determining a matching entry of the dataset in which all minimum diagnostic concentrations are less than the corresponding sample concentrations and identifying an indicated disorder comprising the particular disorder of the matching entry.

Another aspect of the invention encompasses a method for diagnosing, monitoring, or determining obstructive uropathy or an associated disorder in a mammal. The method generally comprises providing a test sample comprising a sample of bodily fluid taken from the mammal. Then the method comprises determining the concentrations of three or more sample analytes in a panel of biomarkers in the test sample, wherein the sample analytes are selected from the group consisting of alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF. Diagnostic analytes are identified in the test sample, wherein the diagnostic analytes are the sample analytes whose concentrations are statistically different from concentrations found in a control group of humans who do not suffer from obstructive uropathy or an associated disorder. The combination of diagnostic analytes is compared to a dataset comprising at least one entry, wherein each entry of the dataset comprises a combination of three or more diagnostic analytes reflective of obstructive uropathy or an associated disorder. The particular disorder having the combination of diagnostic analytes that essentially match the combination of sample analytes is then identified.

Yet another aspect of the invention encompasses a computer readable media encoded with an application comprising modules executable by a processor and configured to diagnose, monitor, or determine obstructive uropathy or an associated disorder in a mammal. The application usually comprises an analyte input module to receive three or more sample analyte concentrations selected from the group consisting of alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF. The media also comprises a comparison module to compare each sample analyte concentration to an entry of an obstructive uropathy or an associated disorder database, wherein each entry comprises a list of minimum diagnostic concentrations reflective of obstructive uropathy or an associated disorder. The media further comprises an analysis module to determine a most likely disorder by combining the particular disorders identified by the comparison module for all of the sample analyte concentrations.

Still another aspect of the invention encompasses a system for diagnosing, monitoring, or determining obstructive uropathy or an associated disorder in a mammal. The system typically comprises, in part, a database to store a plurality of obstructive uropathy or an associated disorder database entries. The system also comprises a processing device comprising a disorder diagnosis application comprising modules executable by the processing device. The disorder diagnosis application comprises an analyte input module to receive three or more sample analyte concentrations selected from the group consisting of alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF; a comparison module to compare each sample analyte concentration to an entry of the obstructive uropathy or an associated disorder database, wherein each entry comprises a list of minimum diagnostic concentrations reflective of obstructive uropathy or an associated disorder; and an analysis module to determine a most likely disorder by combining the particular disorders identified by the comparison module for all of the sample analyte concentrations.

An additional aspect of the invention encompasses a method for diagnosing, monitoring, or determining obstructive uropathy or an associated disorder in a mammal. The method usually comprises providing an analyte concentration measurement device comprising three or more detection antibodies. Each detection antibody comprises an antibody coupled to an indicator, wherein the antigenic determinants of the antibodies are sample analytes associated with obstructive uropathy or an associated disorder. The sample analytes are generally selected from the group consisting of alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF. The method next comprises providing a test sample comprising three or more sample analytes and a bodily fluid taken from the mammal. The test sample is contacted with the detection antibodies and the detection antibodies are allowed to bind to the sample analytes. The concentrations of the sample analytes are determined by detecting the indicators of the detection antibodies bound to the sample analytes in the test sample. The concentrations of each sample analyte correspond to a corresponding minimum diagnostic concentration reflective of obstructive uropathy or an associated disorder.

Other aspects and iterations of the invention are described in more detail below.

DETAILED DESCRIPTION OF THE INVENTION

Figure 1:
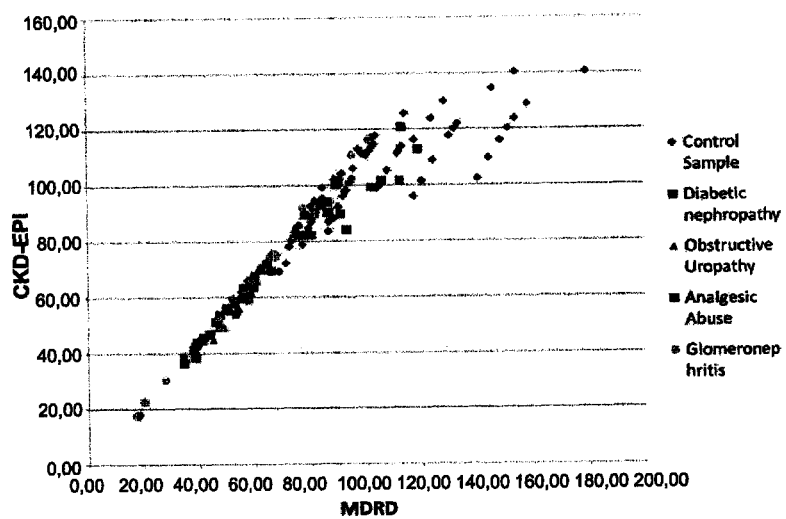
FIG. 1 shows the four different disease groups from which samples were analyzed, and a plot of two different estimations on eGFR outlining the distribution within each group.

It has been discovered that a multiplexed panel of three, six, or preferably 16, biomarkers may be used to detect obstructive uropathy and associated disorders. As used herein, the term "obstructive uropathy" refers to a structural or functional hindrance of normal urine flow. The term may encompass chronic unilateral obstructive uropathy, chronic bilateral obstructive uropathy, acute unilateral obstructive uropathy, or acute bilateral obstructive uropathy. Additionally, the present invention encompasses biomarkers that may be used to detect a disorder associated with obstructive uropathy. As used herein, the phrase "a disorder associated with obstructive uropathy" refers to a disorder that stems from a structural or functional hindrance of normal urine flow. For instance, non-limiting examples of associated disorders may include hydronephrosis and obstructive nephropathy.

The biomarkers included in a multiplexed panel of the invention are analytes known in the art that may be detected in the urine, serum, plasma and other bodily fluids of mammals. As such, the analytes of the multiplexed panel may be readily extracted from the mammal in a test sample of bodily fluid. The concentrations of the analytes within the test sample may be measured using known analytical techniques such as a multiplexed antibody-based immunological assay. The combination of concentrations of the analytes in the test sample may be compared to empirically determined combinations of minimum diagnostic concentrations and combinations of diagnostic concentration ranges associated with healthy kidney function or obstructive uropathy or an associated disorder to determine whether obstructive uropathy is indicated in the mammal.

One embodiment of the present invention provides a method for diagnosing, monitoring, or determining obstructive uropathy or an associated disorder in a mammal that includes determining the presence or concentration of a combination of three or more sample analytes in a test sample containing the bodily fluid of the mammal. The measured concentrations of the combination of sample analytes is compared to the entries of a dataset in which each entry contains the minimum diagnostic concentrations of a combination of three of more analytes reflective of obstructive uropathy or an associated disorder. Other embodiments provide computer-readable media encoded with applications containing executable modules, systems that include databases and processing devices containing executable modules configured to diagnose, monitor, or determine a renal disorder in a mammal. Still other embodiments provide antibody-based devices for diagnosing, monitoring, or determining obstructive uropathy or an associated disorder in a mammal.

The analytes used as biomarkers in the multiplexed assay, methods of diagnosing, monitoring, or determining a renal disorder using measurements of the analytes, systems and applications used to analyze the multiplexed assay measurements, and antibody-based devices used to measure the analytes are described in detail below.

I. Analytes in Multiplexed Assay

One embodiment of the invention measures the concentrations of three, six, or preferably sixteen, biomarker analytes within a test sample taken from a mammal and compares the measured analyte concentrations to minimum diagnostic concentrations to diagnose, monitor, or determine obstructive uropathy or an associated disorder in a mammal. In this aspect, the biomarker analytes are known in the art to occur in the urine, plasma, serum and other bodily fluids of mammals. The biomarker analytes are proteins that have known and documented associations with early renal damage in humans. As defined herein, the biomarker analytes include but are not limited to alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF. A description of each biomarker analyte is given below.

(a) Alpha-1 Microglobulin (A1M)

Alpha-1 microglobulin (A1M, Swiss-Prot Accession Number P02760) is a 26 kDa glycoprotein synthesized by the liver and reabsorbed in the proximal tubules. Elevated levels of A1M in human urine are indicative of glomerulotubular dysfunction. A1M is a member of the lipocalin super family and is found in all tissues. Alpha-1-microglobulin exists in blood in both a free form and complexed with immunoglobulin A (IgA) and heme. Half of plasma A1M exists in a free form, and the remainder exists in complexes with other molecules including prothrombin, albumin, immunoglobulin A and heme. Nearly all of the free A1M in human urine is reabsorbed by the megalin receptor in proximal tubular cells, where it is then catabolized. Small amounts of A1M are excreted in the urine of healthy humans. Increased A1M concentrations in human urine may be an early indicator of renal damage, primarily in the proximal tubule.

(b) Beta-2 Microglobulin (B2M)

Beta-2 microglobulin (B2M, Swiss-Prot Accession Number P61769) is a protein found on the surfaces of all nucleated cells and is shed into the blood, particularly by tumor cells and lymphocytes. Due to its small size, B2M passes through the glomerular membrane, but normally less than 1% is excreted due to reabsorption of B2M in the proximal tubules of the kidney. Therefore, high plasma levels of B2M occur as a result of renal failure, inflammation, and neoplasms, especially those associated with B-lymphocytes.

(c) Calbindin

Calbindin (Calbindin D-28K, Swiss-Prot Accession Number P05937) is a Ca-binding protein belonging to the troponin C superfamily. It is expressed in the kidney, pancreatic islets, and brain. Calbindin is found predominantly in subpopulations of central and peripheral nervous system neurons, in certain epithelial cells involved in Ca2+ transport such as distal tubular cells and cortical collecting tubules of the kidney, and in enteric neuroendocrine cells.

(d) Clusterin

Clusterin (Swiss-Prot Accession Number P10909) is a highly conserved protein that has been identified independently by many different laboratories and named SGP2, S35-S45, apolipoprotein J, SP-40, 40, ADHC-9, gp80, GPIII, and testosterone-repressed prostate message (TRPM-2). An increase in clusterin levels has been consistently detected in apoptotic heart, brain, lung, liver, kidney, pancreas, and retinal tissue both in vivo and in vitro, establishing clusterin as a ubiquitous marker of apoptotic cell loss. However, clusterin protein has also been implicated in physiological processes that do not involve apoptosis, including the control of complement-mediated cell lysis, transport of beta-amyloid precursor protein, shuttling of aberrant beta-amyloid across the blood-brain barrier, lipid scavenging, membrane remodeling, cell aggregation, and protection from immune detection and tumor necrosis factor induced cell death.

(e) Connective Tissue Growth Factor (CTGF)

Connective tissue growth factor (CTGF, Swiss-Prot Accession Number P29279) is a 349-amino acid cysteine-rich polypeptide belonging to the CCN family. In vitro studies have shown that CTGF is mainly involved in extracellular matrix synthesis and fibrosis. Up-regulation of CTGF mRNA and increased CTGF levels have been observed in various diseases, including diabetic nephropathy and cardiomyopathy, fibrotic skin disorders, systemic sclerosis, biliary atresia, liver fibrosis and idiopathic pulmonary fibrosis, and nondiabetic acute and progressive glomerular and tubulointerstitial lesions of the kidney. A recent cross-sectional study found that urinary CTGF may act as a progression promoter in diabetic nephropathy.

(f) Creatinine

Creatinine is a metabolite of creatine phosphate in muscle tissue, and is typically produced at a relatively constant rate by the body. Creatinine is chiefly filtered out of the blood by the kidneys, though a small amount is actively secreted by the kidneys into the urine. Creatinine levels in blood and urine may be used to estimate the creatinine clearance, which is representative of the overall glomerular filtration rate (GFR), a standard measure of renal function. Variations in creatinine concentrations in the blood and urine, as well as variations in the ratio of urea to creatinine concentration in the blood, are common diagnostic measurements used to assess renal function.

(g) Cystatin C (Cyst C)

Cystatin C (Cyst C, Swiss-Prot Accession Number P01034) is a 13 kDa protein that is a potent inhibitor of the C1 family of cysteine proteases. It is the most abundant extracellular inhibitor of cysteine proteases in testis, epididymis, prostate, seminal vesicles and many other tissues. Cystatin C, which is normally expressed in vascular wall smooth muscle cells, is severely reduced in both atherosclerotic and aneurismal aortic lesions.

(h) Glutathione S-Transferase alpha (GST-alpha)

Glutathione S-transferase alpha (GST-alpha, Swiss-Prot Accession Number P08263) belongs to a family of enzymes that utilize glutathione in reactions contributing to the transformation of a wide range of compounds, including carcinogens, therapeutic drugs, and products of oxidative stress. These enzymes play a key role in the detoxification of such substances.

(i) Kidney Injury Molecule-1 (KIM-1)

Kidney injury molecule-1 (KIM-1, Swiss-Prot Accession Number Q96D42) is an immunoglobulin superfamily cell-surface protein highly upregulated on the surface of injured kidney epithelial cells. It is also known as TIM-1 (T-cell immunoglobulin mucin domain-1), as it is expressed at low levels by subpopulations of activated T-cells and hepatitis A virus cellular receptor-1 (HAVCR-1). KIM-1 is increased in expression more than any other protein in the injured kidney and is localized predominantly to the apical membrane of the surviving proximal epithelial cells.

(j) Microalbumin

Albumin is the most abundant plasma protein in humans and other mammals. Albumin is essential for maintaining the osmotic pressure needed for proper distribution of body fluids between intravascular compartments and body tissues. Healthy, normal kidneys typically filter out albumin from the urine. The presence of albumin in the urine may indicate damage to the kidneys. Albumin in the urine may also occur in patients with long-standing diabetes, especially type 1 diabetes. The amount of albumin eliminated in the urine has been used to differentially diagnose various renal disorders. For example, nephrotic syndrome usually results in the excretion of about 3.0 to 3.5 grams of albumin in human urine every 24 hours. Microalbuminuria, in which less than 300 mg of albumin is eliminated in the urine every 24 hours, may indicate the early stages of diabetic nephropathy.

(k) Neutrophil Gelatinase-Associated Lipocalin (NGAL)

Neutrophil gelatinase-associated lipocalin (NGAL, Swiss-Prot Accession Number P80188) forms a disulfide bond-linked heterodimer with MMP-9. It mediates an innate immune response to bacterial infection by sequestrating iron. Lipocalins interact with many different molecules such as cell surface receptors and proteases, and play a role in a variety of processes such as the progression of cancer and allergic reactions.

(l) Osteopontin (OPN)

Osteopontin (OPN, Swiss-Prot Accession Number P10451) is a cytokine involved in enhancing production of interferon-gamma and IL-12, and inhibiting the production of IL-10. OPN is essential in the pathway that leads to type I immunity. OPN appears to form an integral part of the mineralized matrix. OPN is synthesized within the kidney and has been detected in human urine at levels that may effectively inhibit calcium oxalate crystallization. Decreased concentrations of OPN have been documented in urine from patients with renal stone disease compared with normal individuals.

(m) Tamm-Horsfall Protein (THP)

Tamm-Horsfall protein (THP, Swiss-Prot Accession Number P07911), also known as uromodulin, is the most abundant protein present in the urine of healthy subjects and has been shown to decrease in individuals with kidney stones. THP is secreted by the thick ascending limb of the loop of Henley. THP is a monomeric glycoprotein of ~85 kDa with ~30% carbohydrate moiety that is heavily glycosylated. THP may act as a constitutive inhibitor of calcium crystallization in renal fluids.

(n) Tissue Inhibitor of Metalloproteinase-1 (TIMP-1)

Tissue inhibitor of metalloproteinase-1 (TIMP-1, Swiss-Prot Accession Number P01033) is a major regulator of extracellular matrix synthesis and degradation. A certain balance of MMPs and TIMPs is essential for tumor growth and health. Fibrosis results from an imbalance of fibrogenesis and fibrolysis, highlighting the importance of the role of the inhibition of matrix degradation role in renal disease.

(o) Trefoil Factor 3 (TFF3)

Trefoil factor 3 (TFF3, Swiss-Prot Accession Number Q07654), also known as intestinal trefoil factor, belongs to a small family of mucin-associated peptides that include TFF1, TFF2, and TFF3. TFF3 exists in a 60-amino acid monomeric form and a 118-amino acid dimeric form. Under normal conditions TFF3 is expressed by goblet cells of the intestine and the colon. TFF3 expression has also been observed in the human respiratory tract, in human goblet cells and in the human salivary gland. In addition, TFF3 has been detected in the human hypothalamus.

(p) Vascular Endothelial Growth Factor (VEGF)

Vascular endothelial growth factor (VEGF, Swiss-Prot Accession Number P15692) is an important factor in the pathophysiology of neuronal and other tumors, most likely functioning as a potent promoter of angiogenesis. VEGF may also be involved in regulating blood-brain-barrier functions under normal and pathological conditions. VEGF secreted from the stromal cells may be responsible for the endothelial cell proliferation observed in capillary hemangioblastomas, which are typically composed of abundant microvasculature and primitive angiogenic elements represented by stromal cells.

II. Combinations of Analytes Measured by Multiplexed Assay

The method for diagnosing, monitoring, or determining a renal disorder involves determining the presence or concentrations of a combination of sample analytes in a test sample. The combinations of sample analytes, as defined herein, are any group of three or more analytes selected from the biomarker analytes, including but not limited to alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF. In one embodiment, the combination of analytes may be selected to provide a group of analytes associated with obstructive uropathy or an associated disorder.

In one embodiment, the combination of sample analytes may be any three of the biomarker analytes. In other embodiments, the combination of sample analytes may be any four, any five, any six, any seven, any eight, any nine, any ten, any eleven, any twelve, any thirteen, any fourteen, any fifteen, or all sixteen of the sixteen biomarker analytes. In some embodiments, the combination of sample analytes comprises alpha-1 microglobulin, beta-2 microglobulin, cystatin C, KIM-1, THP, and TIMP-1. In another embodiment, the combination of sample analytes may comprise a combination listed in Table A.

TABLE A

| | | |
|---|---|---|
| alpha-1 microglobulin | beta-2 microglobulin | calbindin |
| alpha-1 microglobulin | beta-2 microglobulin | clusterin |
| alpha-1 microglobulin | beta-2 microglobulin | CTGF |
| alpha-1 microglobulin | beta-2 microglobulin | creatinine |
| alpha-1 microglobulin | beta-2 microglobulin | cystatin C |
| alpha-1 microglobulin | beta-2 microglobulin | GST-alpha |
| alpha-1 microglobulin | beta-2 microglobulin | KIM-1 |
| alpha-1 microglobulin | beta-2 microglobulin | microalbumin |
| alpha-1 microglobulin | beta-2 microglobulin | NGAL |
| alpha-1 microglobulin | beta-2 microglobulin | osteopontin |
| alpha-1 microglobulin | beta-2 microglobulin | THP |
| alpha-1 microglobulin | beta-2 microglobulin | TIMP-1 |
| alpha-1 microglobulin | beta-2 microglobulin | TFF-3 |
| alpha-1 microglobulin | beta-2 microglobulin | VEGF |
| alpha-1 microglobulin | calbindin | clusterin |
| alpha-1 microglobulin | calbindin | CTGF |
| alpha-1 microglobulin | calbindin | creatinine |
| alpha-1 microglobulin | calbindin | cystatin C |
| alpha-1 microglobulin | calbindin | GST-alpha |
| alpha-1 microglobulin | calbindin | KIM-1 |
| alpha-1 microglobulin | calbindin | microalbumin |
| alpha-1 microglobulin | calbindin | NGAL |
| alpha-1 microglobulin | calbindin | osteopontin |
| alpha-1 microglobulin | calbindin | THP |
| alpha-1 microglobulin | calbindin | TIMP-1 |
| alpha-1 microglobulin | calbindin | TFF-3 |
| alpha-1 microglobulin | calbindin | VEGF |
| alpha-1 microglobulin | clusterin | CTGF |
| alpha-1 microglobulin | clusterin | creatinine |
| alpha-1 microglobulin | clusterin | cystatin C |
| alpha-1 microglobulin | clusterin | GST-alpha |
| alpha-1 microglobulin | clusterin | KIM-1 |
| alpha-1 microglobulin | clusterin | microalbumin |
| alpha-1 microglobulin | clusterin | NGAL |
| alpha-1 microglobulin | clusterin | osteopontin |
| alpha-1 microglobulin | clusterin | THP |
| alpha-1 microglobulin | clusterin | TIMP-1 |
| alpha-1 microglobulin | clusterin | TFF-3 |
| alpha-1 microglobulin | clusterin | VEGF |
| alpha-1 microglobulin | CTGF | creatinine |
| alpha-1 microglobulin | CTGF | cystatin C |
| alpha-1 microglobulin | CTGF | GST-alpha |
| alpha-1 microglobulin | CTGF | KIM-1 |
| alpha-1 microglobulin | CTGF | microalbumin |
| alpha-1 microglobulin | CTGF | NGAL |
| alpha-1 microglobulin | CTGF | osteopontin |
| alpha-1 microglobulin | CTGF | THP |
| alpha-1 microglobulin | CTGF | TIMP-1 |
| alpha-1 microglobulin | CTGF | TFF-3 |
| alpha-1 microglobulin | CTGF | VEGF |
| alpha-1 microglobulin | creatinine | cystatin C |
| alpha-1 microglobulin | creatinine | GST-alpha |
| alpha-1 microglobulin | creatinine | KIM-1 |
| alpha-1 microglobulin | creatinine | microalbumin |
| alpha-1 microglobulin | creatinine | NGAL |
| alpha-1 microglobulin | creatinine | osteopontin |
| alpha-1 microglobulin | creatinine | THP |
| alpha-1 microglobulin | creatinine | TIMP-1 |
| alpha-1 microglobulin | creatinine | TFF-3 |
| alpha-1 microglobulin | creatinine | VEGF |
| alpha-1 microglobulin | cystatin C | GST-alpha |
| alpha-1 microglobulin | cystatin C | KIM-1 |
| alpha-1 microglobulin | cystatin C | microalbumin |
| alpha-1 microglobulin | cystatin C | NGAL |
| alpha-1 microglobulin | cystatin C | osteopontin |
| alpha-1 microglobulin | cystatin C | THP |
| alpha-1 microglobulin | cystatin C | TIMP-1 |
| alpha-1 microglobulin | cystatin C | TFF-3 |
| alpha-1 microglobulin | cystatin C | VEGF |
| alpha-1 microglobulin | GST-alpha | KIM-1 |
| alpha-1 microglobulin | GST-alpha | microalbumin |
| alpha-1 microglobulin | GST-alpha | NGAL |
| alpha-1 microglobulin | GST-alpha | osteopontin |
| alpha-1 microglobulin | GST-alpha | THP |
| alpha-1 microglobulin | GST-alpha | TIMP-1 |
| alpha-1 microglobulin | GST-alpha | TFF-3 |
| alpha-1 microglobulin | GST-alpha | VEGF |
| alpha-1 microglobulin | KIM-1 | microalbumin |
| alpha-1 microglobulin | KIM-1 | NGAL |
| alpha-1 microglobulin | KIM-1 | osteopontin |
| alpha-1 microglobulin | KIM-1 | THP |
| alpha-1 microglobulin | KIM-1 | TIMP-1 |
| alpha-1 microglobulin | KIM-1 | TFF-3 |
| alpha-1 microglobulin | KIM-1 | VEGF |
| alpha-1 microglobulin | microalbumin | NGAL |
| alpha-1 microglobulin | microalbumin | osteopontin |
| alpha-1 microglobulin | microalbumin | THP |
| alpha-1 microglobulin | microalbumin | TIMP-1 |
| alpha-1 microglobulin | microalbumin | TFF-3 |
| alpha-1 microglobulin | microalbumin | VEGF |
| alpha-1 microglobulin | NGAL | osteopontin |
| alpha-1 microglobulin | NGAL | THP |
| alpha-1 microglobulin | NGAL | TIMP-1 |
| alpha-1 microglobulin | NGAL | TFF-3 |
| alpha-1 microglobulin | NGAL | VEGF |
| alpha-1 microglobulin | osteopontin | THP |
| alpha-1 microglobulin | osteopontin | TIMP-1 |
| alpha-1 microglobulin | osteopontin | TFF-3 |
| alpha-1 microglobulin | osteopontin | VEGF |
| alpha-1 microglobulin | THP | TIMP-1 |
| alpha-1 microglobulin | THP | TFF-3 |
| alpha-1 microglobulin | THP | VEGF |
| alpha-1 microglobulin | TIMP-1 | TFF-3 |
| alpha-1 microglobulin | TIMP-1 | VEGF |
| alpha-1 microglobulin | TFF-3 | VEGF |
| beta-2 microglobulin | calbindin | clusterin |
| beta-2 microglobulin | calbindin | CTGF |
| beta-2 microglobulin | calbindin | creatinine |
| beta-2 microglobulin | calbindin | cystatin C |
| beta-2 microglobulin | calbindin | GST-alpha |
| beta-2 microglobulin | calbindin | KIM-1 |
| beta-2 microglobulin | calbindin | microalbumin |
| beta-2 microglobulin | calbindin | NGAL |
| beta-2 microglobulin | calbindin | osteopontin |
| beta-2 microglobulin | calbindin | THP |
| beta-2 microglobulin | calbindin | TIMP-1 |
| beta-2 microglobulin | calbindin | TFF-3 |
| beta-2 microglobulin | calbindin | VEGF |
| beta-2 microglobulin | clusterin | CTGF |
| beta-2 microglobulin | clusterin | creatinine |
| beta-2 microglobulin | clusterin | cystatin C |
| beta-2 microglobulin | clusterin | GST-alpha |
| beta-2 microglobulin | clusterin | KIM-1 |
| beta-2 microglobulin | clusterin | microalbumin |
| beta-2 microglobulin | clusterin | NGAL |
| beta-2 microglobulin | clusterin | osteopontin |
| beta-2 microglobulin | clusterin | THP |
| beta-2 microglobulin | clusterin | TIMP-1 |
| beta-2 microglobulin | clusterin | TFF-3 |
| beta-2 microglobulin | clusterin | VEGF |
| beta-2 microglobulin | CTGF | creatinine |
| beta-2 microglobulin | CTGF | cystatin C |
| beta-2 microglobulin | CTGF | GST-alpha |
| beta-2 microglobulin | CTGF | KIM-1 |
| beta-2 microglobulin | CTGF | microalbumin |
| beta-2 microglobulin | CTGF | NGAL |
| beta-2 microglobulin | CTGF | osteopontin |
| beta-2 microglobulin | CTGF | THP |
| beta-2 microglobulin | CTGF | TIMP-1 |
| beta-2 microglobulin | CTGF | TFF-3 |
| beta-2 microglobulin | CTGF | VEGF |
| beta-2 microglobulin | creatinine | cystatin C |
| beta-2 microglobulin | creatinine | GST-alpha |
| beta-2 microglobulin | creatinine | KIM-1 |
| beta-2 microglobulin | creatinine | microalbumin |
| beta-2 microglobulin | creatinine | NGAL |
| beta-2 microglobulin | creatinine | osteopontin |
| beta-2 microglobulin | creatinine | THP |
| beta-2 microglobulin | creatinine | TIMP-1 |
| beta-2 microglobulin | creatinine | TFF-3 |
| beta-2 microglobulin | creatinine | VEGF |
| beta-2 microglobulin | cystatin C | GST-alpha |
| beta-2 microglobulin | cystatin C | KIM-1 |
| beta-2 microglobulin | cystatin C | microalbumin |
| beta-2 microglobulin | cystatin C | NGAL |

TABLE A-continued

| | | |
|---|---|---|
| beta-2 microglobulin | cystatin C | osteopontin |
| beta-2 microglobulin | cystatin C | THP |
| beta-2 microglobulin | cystatin C | TIMP-1 |
| beta-2 microglobulin | cystatin C | TFF-3 |
| beta-2 microglobulin | cystatin C | VEGF |
| beta-2 microglobulin | GST-alpha | KIM-1 |
| beta-2 microglobulin | GST-alpha | microalbumin |
| beta-2 microglobulin | GST-alpha | NGAL |
| beta-2 microglobulin | GST-alpha | osteopontin |
| beta-2 microglobulin | GST-alpha | THP |
| beta-2 microglobulin | GST-alpha | TIMP-1 |
| beta-2 microglobulin | GST-alpha | TFF-3 |
| beta-2 microglobulin | GST-alpha | VEGF |
| beta-2 microglobulin | KIM-1 | microalbumin |
| beta-2 microglobulin | KIM-1 | NGAL |
| beta-2 microglobulin | KIM-1 | osteopontin |
| beta-2 microglobulin | KIM-1 | THP |
| beta-2 microglobulin | KIM-1 | TIMP-1 |
| beta-2 microglobulin | KIM-1 | TFF-3 |
| beta-2 microglobulin | KIM-1 | VEGF |
| beta-2 microglobulin | microalbumin | NGAL |
| beta-2 microglobulin | microalbumin | osteopontin |
| beta-2 microglobulin | microalbumin | THP |
| beta-2 microglobulin | microalbumin | TIMP-1 |
| beta-2 microglobulin | microalbumin | TFF-3 |
| beta-2 microglobulin | microalbumin | VEGF |
| beta-2 microglobulin | NGAL | osteopontin |
| beta-2 microglobulin | NGAL | THP |
| beta-2 microglobulin | NGAL | TIMP-1 |
| beta-2 microglobulin | NGAL | TFF-3 |
| beta-2 microglobulin | NGAL | VEGF |
| beta-2 microglobulin | osteopontin | THP |
| beta-2 microglobulin | osteopontin | TIMP-1 |
| beta-2 microglobulin | osteopontin | TFF-3 |
| beta-2 microglobulin | osteopontin | VEGF |
| beta-2 microglobulin | THP | TIMP-1 |
| beta-2 microglobulin | THP | TFF-3 |
| beta-2 microglobulin | THP | VEGF |
| beta-2 microglobulin | TIMP-1 | TFF-3 |
| beta-2 microglobulin | TIMP-2 | VEGF |
| beta-2 microglobulin | TFF-3 | VEGF |
| calbindin | clusterin | CTGF |
| calbindin | clusterin | creatinine |
| calbindin | clusterin | cystatin C |
| calbindin | clusterin | GST-alpha |
| calbindin | clusterin | KIM-1 |
| calbindin | clusterin | microalbumin |
| calbindin | clusterin | NGAL |
| calbindin | clusterin | osteopontin |
| calbindin | clusterin | THP |
| calbindin | clusterin | TIMP-1 |
| calbindin | clusterin | TFF-3 |
| calbindin | clusterin | VEGF |
| calbindin | CTGF | creatinine |
| calbindin | CTGF | cystatin C |
| calbindin | CTGF | GST-alpha |
| calbindin | CTGF | KIM-1 |
| calbindin | CTGF | microalbumin |
| calbindin | CTGF | NGAL |
| calbindin | CTGF | osteopontin |
| calbindin | CTGF | THP |
| calbindin | CTGF | TIMP-1 |
| calbindin | CTGF | TFF-3 |
| calbindin | CTGF | VEGF |
| calbindin | creatinine | cystatin C |
| calbindin | creatinine | GST-alpha |
| calbindin | creatinine | KIM-1 |
| calbindin | creatinine | microalbumin |
| calbindin | creatinine | NGAL |
| calbindin | creatinine | osteopontin |
| calbindin | creatinine | THP |
| calbindin | creatinine | TIMP-1 |
| calbindin | creatinine | TFF-3 |
| calbindin | creatinine | VEGF |
| calbindin | cystatin C | GST-alpha |
| calbindin | cystatin C | KIM-1 |
| calbindin | cystatin C | microalbumin |
| calbindin | cystatin C | NGAL |
| calbindin | cystatin C | osteopontin |
| calbindin | cystatin C | THP |
| calbindin | cystatin C | TIMP-1 |
| calbindin | cystatin C | TFF-3 |
| calbindin | cystatin C | VEGF |
| calbindin | GST-alpha | KIM-1 |
| calbindin | GST-alpha | microalbumin |
| calbindin | GST-alpha | NGAL |
| calbindin | GST-alpha | osteopontin |
| calbindin | GST-alpha | THP |
| calbindin | GST-alpha | TIMP-1 |
| calbindin | GST-alpha | TFF-3 |
| calbindin | GST-alpha | VEGF |
| calbindin | KIM-1 | microalbumin |
| calbindin | KIM-1 | NGAL |
| calbindin | KIM-1 | osteopontin |
| calbindin | KIM-1 | THP |
| calbindin | KIM-1 | TIMP-1 |
| calbindin | KIM-1 | TFF-3 |
| calbindin | KIM-1 | VEGF |
| calbindin | microalbumin | NGAL |
| calbindin | microalbumin | osteopontin |
| calbindin | microalbumin | THP |
| calbindin | microalbumin | TIMP-1 |
| calbindin | microalbumin | TFF-3 |
| calbindin | microalbumin | VEGF |
| calbindin | NGAL | osteopontin |
| calbindin | NGAL | THP |
| calbindin | NGAL | TIMP-1 |
| calbindin | NGAL | TFF-3 |
| calbindin | NGAL | VEGF |
| calbindin | osteopontin | THP |
| calbindin | osteopontin | TIMP-1 |
| calbindin | osteopontin | TFF-3 |
| calbindin | osteopontin | VEGF |
| calbindin | THP | TIMP-1 |
| calbindin | THP | TFF-3 |
| calbindin | THP | VEGF |
| calbindin | TIMP-1 | TFF-3 |
| calbindin | TIMP-1 | VEGF |
| calbindin | TFF-3 | VEGF |
| clusterin | CTGF | creatinine |
| clusterin | CTGF | cystatin C |
| clusterin | CTGF | GST-alpha |
| clusterin | CTGF | KIM-1 |
| clusterin | CTGF | microalbumin |
| clusterin | CTGF | NGAL |
| clusterin | CTGF | osteopontin |
| clusterin | CTGF | THP |
| clusterin | CTGF | TIMP-1 |
| clusterin | CTGF | TFF-3 |
| clusterin | CTGF | VEGF |
| clusterin | creatinine | cystatin C |
| clusterin | creatinine | GST-alpha |
| clusterin | creatinine | KIM-1 |
| clusterin | creatinine | microalbumin |
| clusterin | creatinine | NGAL |
| clusterin | creatinine | osteopontin |
| clusterin | creatinine | THP |
| clusterin | creatinine | TIMP-1 |
| clusterin | creatinine | TFF-3 |
| clusterin | creatinine | VEGF |
| clusterin | cystatin C | GST-alpha |
| clusterin | cystatin C | KIM-1 |
| clusterin | cystatin C | microalbumin |
| clusterin | cystatin C | NGAL |
| clusterin | cystatin C | osteopontin |
| clusterin | cystatin C | THP |
| clusterin | cystatin C | TIMP-1 |
| clusterin | cystatin C | TFF-3 |
| clusterin | cystatin C | VEGF |
| clusterin | GST-alpha | KIM-1 |
| clusterin | GST-alpha | microalbumin |
| clusterin | GST-alpha | NGAL |
| clusterin | GST-alpha | osteopontin |
| clusterin | GST-alpha | THP |
| clusterin | GST-alpha | TIMP-1 |
| clusterin | GST-alpha | TFF-3 |
| clusterin | GST-alpha | VEGF |
| clusterin | KIM-1 | microalbumin |
| clusterin | KIM-1 | NGAL |
| clusterin | KIM-1 | osteopontin |

TABLE A-continued

| | | |
|---|---|---|
| clusterin | KIM-1 | THP |
| clusterin | KIM-1 | TIMP-1 |
| clusterin | KIM-1 | TFF-3 |
| clusterin | KIM-1 | VEGF |
| clusterin | microalbumin | NGAL |
| clusterin | microalbumin | osteopontin |
| clusterin | microalbumin | THP |
| clusterin | microalbumin | TIMP-1 |
| clusterin | microalbumin | TFF-3 |
| clusterin | microalbumin | VEGF |
| clusterin | NGAL | osteopontin |
| clusterin | NGAL | THP |
| clusterin | NGAL | TIMP-1 |
| clusterin | NGAL | TFF-3 |
| clusterin | NGAL | VEGF |
| clusterin | osteopontin | THP |
| clusterin | osteopontin | TIMP-1 |
| clusterin | osteopontin | TFF-3 |
| clusterin | osteopontin | VEGF |
| clusterin | THP | TIMP-1 |
| clusterin | THP | TFF-3 |
| clusterin | THP | VEGF |
| clusterin | TIMP-1 | TFF-3 |
| clusterin | TIMP-1 | VEGF |
| clusterin | TFF-3 | VEGF |
| CTGF | creatinine | cystatin C |
| CTGF | creatinine | GST-alpha |
| CTGF | creatinine | KIM-1 |
| CTGF | creatinine | microalbumin |
| CTGF | creatinine | NGAL |
| CTGF | creatinine | osteopontin |
| CTGF | creatinine | THP |
| CTGF | creatinine | TIMP-1 |
| CTGF | creatinine | TFF-3 |
| CTGF | creatinine | VEGF |
| CTGF | cystatin C | GST-alpha |
| CTGF | cystatin C | KIM-1 |
| CTGF | cystatin C | microalbumin |
| CTGF | cystatin C | NGAL |
| CTGF | cystatin C | osteopontin |
| CTGF | cystatin C | THP |
| CTGF | cystatin C | TIMP-1 |
| CTGF | cystatin C | TFF-3 |
| CTGF | cystatin C | VEGF |
| CTGF | GST-alpha | KIM-1 |
| CTGF | GST-alpha | microalbumin |
| CTGF | GST-alpha | NGAL |
| CTGF | GST-alpha | osteopontin |
| CTGF | GST-alpha | THP |
| CTGF | GST-alpha | TIMP-1 |
| CTGF | GST-alpha | TFF-3 |
| CTGF | GST-alpha | VEGF |
| CTGF | KIM-1 | microalbumin |
| CTGF | KIM-1 | NGAL |
| CTGF | KIM-1 | osteopontin |
| CTGF | KIM-1 | THP |
| CTGF | KIM-1 | TIMP-1 |
| CTGF | KIM-1 | TFF-3 |
| CTGF | KIM-1 | VEGF |
| CTGF | microalbumin | NGAL |
| CTGF | microalbumin | osteopontin |
| CTGF | microalbumin | THP |
| CTGF | microalbumin | TIMP-1 |
| CTGF | microalbumin | TFF-3 |
| CTGF | microalbumin | VEGF |
| CTGF | NGAL | osteopontin |
| CTGF | NGAL | THP |
| CTGF | NGAL | TIMP-1 |
| CTGF | NGAL | TFF-3 |
| CTGF | NGAL | VEGF |
| CTGF | osteopontin | THP |
| CTGF | osteopontin | TIMP-1 |
| CTGF | osteopontin | TFF-3 |
| CTGF | osteopontin | VEGF |
| CTGF | THP | TIMP-1 |
| CTGF | THP | TFF-3 |
| CTGF | THP | VEGF |
| CTGF | TIMP-1 | TFF-3 |
| CTGF | TIMP-1 | VEGF |
| CTGF | TFF-3 | VEGF |
| creatinine | cystatin C | GST-alpha |
| creatinine | cystatin C | KIM-1 |
| creatinine | cystatin C | microalbumin |
| creatinine | cystatin C | NGAL |
| creatinine | cystatin C | osteopontin |
| creatinine | cystatin C | THP |
| creatinine | cystatin C | TIMP-1 |
| creatinine | cystatin C | TFF-3 |
| creatinine | cystatin C | VEGF |
| creatinine | GST-alpha | KIM-1 |
| creatinine | GST-alpha | microalbumin |
| creatinine | GST-alpha | NGAL |
| creatinine | GST-alpha | osteopontin |
| creatinine | GST-alpha | THP |
| creatinine | GST-alpha | TIMP-1 |
| creatinine | GST-alpha | TFF-3 |
| creatinine | GST-alpha | VEGF |
| creatinine | KIM-1 | microalbumin |
| creatinine | KIM-1 | NGAL |
| creatinine | KIM-1 | osteopontin |
| creatinine | KIM-1 | THP |
| creatinine | KIM-1 | TIMP-1 |
| creatinine | KIM-1 | TFF-3 |
| creatinine | KIM-1 | VEGF |
| creatinine | microalbumin | NGAL |
| creatinine | microalbumin | osteopontin |
| creatinine | microalbumin | THP |
| creatinine | microalbumin | TIMP-1 |
| creatinine | microalbumin | TFF-3 |
| creatinine | microalbumin | VEGF |
| creatinine | NGAL | osteopontin |
| creatinine | NGAL | THP |
| creatinine | NGAL | TIMP-1 |
| creatinine | NGAL | TFF-3 |
| creatinine | NGAL | VEGF |
| creatinine | osteopontin | THP |
| creatinine | osteopontin | TIMP-1 |
| creatinine | osteopontin | TFF-3 |
| creatinine | osteopontin | VEGF |
| creatinine | THP | TIMP-1 |
| creatinine | THP | TFF-3 |
| creatinine | THP | VEGF |
| creatinine | TIMP-1 | TFF-3 |
| creatinine | TIMP-1 | VEGF |
| creatinine | TFF-3 | VEGF |
| cystatin C | GST-alpha | KIM-1 |
| cystatin C | GST-alpha | microalbumin |
| cystatin C | GST-alpha | NGAL |
| cystatin C | GST-alpha | osteopontin |
| cystatin C | GST-alpha | THP |
| cystatin C | GST-alpha | TIMP-1 |
| cystatin C | GST-alpha | TFF-3 |
| cystatin C | GST-alpha | VEGF |
| cystatin C | KIM-1 | microalbumin |
| cystatin C | KIM-1 | NGAL |
| cystatin C | KIM-1 | osteopontin |
| cystatin C | KIM-1 | THP |
| cystatin C | KIM-1 | TIMP-1 |
| cystatin C | KIM-1 | TFF-3 |
| cystatin C | KIM-1 | VEGF |
| cystatin C | microalbumin | NGAL |
| cystatin C | microalbumin | osteopontin |
| cystatin C | microalbumin | THP |
| cystatin C | microalbumin | TIMP-1 |
| cystatin C | microalbumin | TFF-3 |
| cystatin C | microalbumin | VEGF |
| cystatin C | NGAL | osteopontin |
| cystatin C | NGAL | THP |
| cystatin C | NGAL | TIMP-1 |
| cystatin C | NGAL | TFF-3 |
| cystatin C | NGAL | VEGF |
| cystatin C | osteopontin | THP |
| cystatin C | osteopontin | TIMP-1 |
| cystatin C | osteopontin | TFF-3 |
| cystatin C | osteopontin | VEGF |
| cystatin C | THP | TIMP-1 |
| cystatin C | THP | TFF-3 |
| cystatin C | THP | VEGF |
| cystatin C | TIMP-1 | TFF-3 |
| cystatin C | TIMP-1 | VEGF |

TABLE A-continued

| | | |
|---|---|---|
| cystatin C | TFF-3 | VEGF |
| GST-alpha | KIM-1 | microalbumin |
| GST-alpha | KIM-1 | NGAL |
| GST-alpha | KIM-1 | osteopontin |
| GST-alpha | KIM-1 | THP |
| GST-alpha | KIM-1 | TIMP-1 |
| GST-alpha | KIM-1 | TFF-3 |
| GST-alpha | KIM-1 | VEGF |
| GST-alpha | microalbumin | NGAL |
| GST-alpha | microalbumin | osteopontin |
| GST-alpha | microalbumin | THP |
| GST-alpha | microalbumin | TIMP-1 |
| GST-alpha | microalbumin | TFF-3 |
| GST-alpha | microalbumin | VEGF |
| GST-alpha | NGAL | osteopontin |
| GST-alpha | NGAL | THP |
| GST-alpha | NGAL | TIMP-1 |
| GST-alpha | NGAL | TFF-3 |
| GST-alpha | NGAL | VEGF |
| GST-alpha | osteopontin | THP |
| GST-alpha | osteopontin | TIMP-1 |
| GST-alpha | osteopontin | TFF-3 |
| GST-alpha | osteopontin | VEGF |
| GST-alpha | THP | TIMP-1 |
| GST-alpha | THP | TFF-3 |
| GST-alpha | THP | VEGF |
| GST-alpha | TIMP-1 | TFF-3 |
| GST-alpha | TIMP-1 | VEGF |
| GST-alpha | TFF-3 | VEGF |
| KIM-1 | microalbumin | NGAL |
| KIM-1 | microalbumin | osteopontin |
| KIM-1 | microalbumin | THP |
| KIM-1 | microalbumin | TIMP-1 |
| KIM-1 | microalbumin | TFF-3 |
| KIM-1 | microalbumin | VEGF |
| KIM-1 | NGAL | osteopontin |
| KIM-1 | NGAL | THP |
| KIM-1 | NGAL | TIMP-1 |
| KIM-1 | NGAL | TFF-3 |
| KIM-1 | NGAL | VEGF |
| KIM-1 | osteopontin | THP |
| KIM-1 | osteopontin | TIMP-1 |
| KIM-1 | osteopontin | TFF-3 |
| KIM-1 | osteopontin | VEGF |
| KIM-1 | THP | TIMP-1 |
| KIM-1 | THP | TFF-3 |
| KIM-1 | THP | VEGF |
| KIM-1 | TIMP-1 | TFF-3 |
| KIM-1 | TIMP-1 | VEGF |
| KIM-1 | TFF-3 | VEGF |
| microalbumin | NGAL | osteopontin |
| microalbumin | NGAL | THP |
| microalbumin | NGAL | TIMP-1 |
| microalbumin | NGAL | TFF-3 |
| microalbumin | NGAL | VEGF |
| microalbumin | osteopontin | THP |
| microalbumin | osteopontin | TIMP-1 |
| microalbumin | osteopontin | TFF-3 |
| microalbumin | osteopontin | VEGF |
| microalbumin | THP | TIMP-1 |
| microalbumin | THP | TFF-3 |
| microalbumin | THP | VEGF |
| microalbumin | TIMP-1 | TFF-3 |
| microalbumin | TIMP-1 | VEGF |
| microalbumin | TFF-3 | VEGF |
| NGAL | osteopontin | THP |
| NGAL | osteopontin | TIMP-1 |
| NGAL | osteopontin | TFF-3 |
| NGAL | osteopontin | VEGF |
| NGAL | THP | TIMP-1 |
| NGAL | THP | TFF-3 |
| NGAL | THP | VEGF |
| NGAL | TIMP-1 | TFF-3 |
| NGAL | TIMP-1 | VEGF |
| NGAL | TFF-3 | VEGF |
| osteopontin | THP | TIMP-1 |
| osteopontin | THP | TFF-3 |
| osteopontin | THP | VEGF |
| osteopontin | TIMP-1 | TFF-3 |
| osteopontin | TIMP-1 | VEGF |
| osteopontin | TFF-3 | VEGF |
| THP | TIMP-1 | TFF-3 |
| THP | TIMP-1 | VEGF |
| THP | TFF-3 | VEGF |
| TIMP-1 | TFF-3 | VEGF |

In one exemplary embodiment, the combination of sample analytes may include creatinine, KIM-1, and THP. In another exemplary embodiment, the combination of sample analytes may include microalbumin, creatinine, and KIM-1. In yet another exemplary embodiment, the combination of sample analytes may include creatinine, THP, and A1M. In still another exemplary embodiment, the combination of sample analytes may include microalbumin, TIMP-1, and osteopontin. In an alternative exemplary embodiment, the combination of sample analytes may include creatinine, THP, alpha 1 microglobulin, clusterin, NGAL, and osteopontin.

III. Test Sample

The method for diagnosing, monitoring, or determining a renal disorder involves determining the presence of sample analytes in a test sample. A test sample, as defined herein, is an amount of bodily fluid taken from a mammal. Non-limiting examples of bodily fluids include urine, blood, plasma, serum, saliva, semen, perspiration, tears, mucus, and tissue lysates. In an exemplary embodiment, the bodily fluid contained in the test sample is urine, plasma, or serum.

(a) Mammals

A mammal, as defined herein, is any organism that is a member of the class Mammalia. Non-limiting examples of mammals appropriate for the various embodiments may include humans, apes, monkeys, rats, mice, dogs, cats, pigs, and livestock including cattle and oxen. In an exemplary embodiment, the mammal is a human.

(b) Devices and Methods of Taking Bodily Fluids from Mammals

The bodily fluids of the test sample may be taken from the mammal using any known device or method so long as the analytes to be measured by the multiplexed assay are not rendered undetectable by the multiplexed assay. Non-limiting examples of devices or methods suitable for taking bodily fluid from a mammal include urine sample cups, urethral catheters, swabs, hypodermic needles, thin needle biopsies, hollow needle biopsies, punch biopsies, metabolic cages, and aspiration.

In order to adjust the expected concentrations of the sample analytes in the test sample to fall within the dynamic range of the multiplexed assay, the test sample may be diluted to reduce the concentration of the sample analytes prior to analysis. The degree of dilution may depend on a variety of factors including but not limited to the type of multiplexed assay used to measure the analytes, the reagents utilized in the multiplexed assay, and the type of bodily fluid contained in the test sample. In one embodiment, the test sample is diluted by adding a volume of diluent ranging from about ½ of the original test sample volume to about 50,000 times the original test sample volume.

In one exemplary embodiment, if the test sample is human urine and the multiplexed assay is an antibody-based capture-sandwich assay, the test sample is diluted by adding a volume of diluent that is about 100 times the original test sample volume prior to analysis. In another exemplary embodiment, if the test sample is human serum and the multiplexed assay is an antibody-based capture-sandwich assay, the test sample is diluted by adding a volume of diluent that is about 5 times the original test sample volume prior to analysis. In yet another exemplary embodiment, if the test sample is human plasma and the multiplexed assay is an antibody-based capture-sandwich assay, the test sample is diluted by adding a volume of diluent that is about 2,000 times the original test sample volume prior to analysis.

The diluent may be any fluid that does not interfere with the function of the multiplexed assay used to measure the concentration of the analytes in the test sample. Non-limiting examples of suitable diluents include deionized water, distilled water, saline solution, Ringer's solution, phosphate buffered saline solution, TRIS-buffered saline solution, standard saline citrate, and HEPES-buffered saline.

IV. Multiplexed Assay Device

In one embodiment, the concentration of a combination of sample analytes is measured using a multiplexed assay device capable of measuring the concentrations of three or more, preferably sixteen, of the biomarker analytes. A multiplexed assay device, as defined herein, is an assay capable of simultaneously determining the concentration of three or more different sample analytes using a single device and/or method. Any known method of measuring the concentration of the biomarker analytes may be used for the multiplexed assay device. Non-limiting examples of measurement methods suitable for the multiplexed assay device may include electrophoresis, mass spectrometry, protein microarrays, surface plasmon resonance and immunoassays including but not limited to western blot, immunohistochemical staining, enzyme-linked immunosorbent assay (ELISA) methods, and particle-based capture-sandwich immunoassays.

(a) Multiplexed Immunoassay Device

In one embodiment, the concentrations of the analytes in the test sample are measured using a multiplexed immunoassay device that utilizes capture antibodies marked with indicators to determine the concentration of the sample analytes.

(i) Capture Antibodies

In the same embodiment, the multiplexed immunoassay device includes three or more capture antibodies. Capture antibodies, as defined herein, are antibodies in which the antigenic determinant is one of the biomarker analytes. Each of the at least three capture antibodies has a unique antigenic determinant that is one of the biomarker analytes. When contacted with the test sample, the capture antibodies form antigen-antibody complexes in which the analytes serve as antigens.

The term "antibody," as used herein, encompasses a monoclonal ab, an antibody fragment, a chimeric antibody, and a single-chain antibody.

In some embodiments, the capture antibodies may be attached to a substrate in order to immobilize any analytes captured by the capture antibodies. Non-limiting examples of suitable substrates include paper, cellulose, glass, or plastic strips, beads, or surfaces, such as the inner surface of the well of a microtitration tray. Suitable beads may include polystyrene or latex microspheres.

(ii) Indicators

In one embodiment of the multiplexed immunoassay device, an indicator is attached to each of the three or more capture antibodies. The indicator, as defined herein, is any compound that registers a measurable change to indicate the presence of one of the sample analytes when bound to one of the capture antibodies. Non-limiting examples of indicators include visual indicators and electrochemical indicators.

Visual indicators, as defined herein, are compounds that register a change by reflecting a limited subset of the wavelengths of light illuminating the indicator, by fluorescing light after being illuminated, or by emitting light via chemiluminescence. The change registered by visual indicators may be in the visible light spectrum, in the infrared spectrum, or in the ultraviolet spectrum. Non-limiting examples of visual indicators suitable for the multiplexed immunoassay device include nanoparticulate gold, organic particles such as polyurethane or latex microspheres loaded with dye compounds, carbon black, fluorophores, phycoerythrin, radioactive isotopes, nanoparticles, quantum dots, and enzymes such as horseradish peroxidase or alkaline phosphatase that react with a chemical substrate to form a colored or chemiluminescent product.

Electrochemical indicators, as defined herein, are compounds that register a change by altering an electrical property. The changes registered by electrochemical indicators may be an alteration in conductivity, resistance, capacitance, current conducted in response to an applied voltage, or voltage required to achieve a desired current. Non-limiting examples of electrochemical indicators include redox species such as ascorbate (vitamin C), vitamin E, glutathione, polyphenols, catechols, quercetin, phytoestrogens, penicillin, carbazole, murranes, phenols, carbonyls, benzoates, and trace metal ions such as nickel, copper, cadmium, iron and mercury.

In this same embodiment, the test sample containing a combination of three or more sample analytes is contacted with the capture antibodies and allowed to form antigen-antibody complexes in which the sample analytes serve as the antigens. After removing any uncomplexed capture antibodies, the concentrations of the three or more analytes are determined by measuring the change registered by the indicators attached to the capture antibodies.

In one exemplary embodiment, the indicators are polyurethane or latex microspheres loaded with dye compounds and phycoerythrin.

(b) Multiplexed Sandwich Immunoassay Device

In another embodiment, the multiplexed immunoassay device has a sandwich assay format. In this embodiment, the multiplexed sandwich immunoassay device includes three or more capture antibodies as previously described. However, in this embodiment, each of the capture antibodies is attached to a capture agent that includes an antigenic moiety. The antigenic moiety serves as the antigenic determinant of a detection antibody, also included in the multiplexed immunoassay device of this embodiment. In addition, an indicator is attached to the detection antibody.

In this same embodiment, the test sample is contacted with the capture antibodies and allowed to form antigen-antibody complexes in which the sample analytes serve as antigens. The detection antibodies are then contacted with the test sample and allowed to form antigen-antibody complexes in which the capture agent serves as the antigen for the detection antibody. After removing any uncomplexed detection antibodies the concentration of the analytes are determined by measuring the changes registered by the indicators attached to the detection antibodies.

(c) Multiplexing Approaches

In the various embodiments of the multiplexed immunoassay devices, the concentrations of each of the sample analytes may be determined using any approach known in the art. In one embodiment, a single indicator compound is attached to each of the three or more antibodies. In addition, each of the capture antibodies having one of the sample analytes as an antigenic determinant is physically separated into a distinct region so that the concentration of each of the sample analytes may be determined by measuring the changes registered by the indicators in each physically separate region corresponding to each of the sample analytes.

In another embodiment, each antibody having one of the sample analytes as an antigenic determinant is marked with a unique indicator. In this manner, a unique indicator is attached to each antibody having a single sample analyte as its antigenic determinant. In this embodiment, all antibodies may occupy the same physical space. The concentration of each sample analyte is determined by measuring the change registered by the unique indicator attached to the antibody having the sample analyte as an antigenic determinant.

(d) Microsphere-Based Capture-Sandwich Immunoassay Device

In an exemplary embodiment, the multiplexed immunoassay device is a microsphere-based capture-sandwich immunoassay device. In this embodiment, the device includes a mixture of three or more capture-antibody microspheres, in which each capture-antibody microsphere corresponds to one of the biomarker analytes. Each capture-antibody microsphere includes a plurality of capture antibodies attached to the outer surface of the microsphere. In this same embodiment, the antigenic determinant of all of the capture antibodies attached to one microsphere is the same biomarker analyte.

In this embodiment of the device, the microsphere is a small polystyrene or latex sphere that is loaded with an indicator that is a dye compound. The microsphere may be between about 3 μm and about 5 μm in diameter. Each capture-antibody microsphere corresponding to one of the biomarker analytes is loaded with the same indicator. In this manner, each capture-antibody microsphere corresponding to a biomarker analyte is uniquely color-coded.

In this same exemplary embodiment, the multiplexed immunoassay device further includes three or more biotinylated detection antibodies in which the antigenic determinant of each biotinylated detection antibody is one of the biomarker analytes. The device further includes a plurality of streptaviden proteins complexed with a reporter compound. A reporter compound, as defined herein, is an indicator selected to register a change that is distinguishable from the indicators used to mark the capture-antibody microspheres.

The concentrations of the sample analytes may be determined by contacting the test sample with a mixture of capture-antigen microspheres corresponding to each sample analyte to be measured. The sample analytes are allowed to form antigen-antibody complexes in which a sample analyte serves as an antigen and a capture antibody attached to the microsphere serves as an antibody. In this manner, the sample analytes are immobilized onto the capture-antigen microspheres. The biotinylated detection antibodies are then added to the test sample and allowed to form antigen-antibody complexes in which the analyte serves as the antigen and the biotinylated detection antibody serves as the antibody. The streptaviden-reporter complex is then added to the test sample and allowed to bind to the biotin moieties of the biotinylated detection antibodies. The antigen-capture microspheres may then be rinsed and filtered.

In this embodiment, the concentration of each analyte is determined by first measuring the change registered by the indicator compound embedded in the capture-antigen microsphere in order to identify the particular analyte. For each microsphere corresponding to one of the biomarker analytes, the quantity of analyte immobilized on the microsphere is determined by measuring the change registered by the reporter compound attached to the microsphere.

For example, the indicator embedded in the microspheres associated with one sample analyte may register an emission of orange light, and the reporter may register an emission of green light. In this example, a detector device may measure the intensity of orange light and green light separately. The measured intensity of the green light would determine the concentration of the analyte captured on the microsphere, and the intensity of the orange light would determine the specific analyte captured on the microsphere.

Any sensor device may be used to detect the changes registered by the indicators embedded in the microspheres and the changes registered by the reporter compound, so long as the sensor device is sufficiently sensitive to the changes registered by both indicator and reporter compound. Non-limiting examples of suitable sensor devices include spectrophotometers, photosensors, colorimeters, cyclic coulometry devices, and flow cytometers. In an exemplary embodiment, the sensor device is a flow cytometer.

V. Method for Diagnosing, Monitoring, or Determining a Renal Disorder

In one embodiment, a method is provided for diagnosing, monitoring, or determining obstructive uropathy or an associated disorder that includes providing a test sample, determining the concentration of a combination of three or more sample analytes, comparing the measured concentrations of the combination of sample analytes to the entries of a dataset, and identifying obstructive uropathy or an associated disorder based on the comparison between the concentrations of the sample analytes and the minimum diagnostic concentrations contained within each entry of the dataset.

(a) Diagnostic Dataset

In an embodiment, the concentrations of the sample analytes are compared to the entries of a dataset. In this embodiment, each entry of the dataset includes a combination of three or more minimum diagnostic concentrations indicative of a particular renal disorder. A minimum diagnostic concentration, as defined herein, is the concentration of an analyte that defines the limit between the concentration range corresponding to normal, healthy renal function and the concentration reflective of a particular renal disorder. In one embodiment, each minimum diagnostic concentration is the maximum concentration of the range of analyte concentrations for a healthy, normal individual. The minimum diagnostic concentration of an analyte depends on a number of factors including but not limited to the particular analyte and the type of bodily fluid contained in the test sample. As an illustrative example, Table 1 lists the expected normal ranges of the biomarker analytes in human plasma, serum, and urine.

TABLE 1

Normal Concentration Ranges In Human Plasma, Serum, and Urine Samples

| Analyte | Units | Plasma | | Sera | | Urine | |
| --- | --- | --- | --- | --- | --- | --- | --- |
| | | low | high | low | high | low | high |
| Calbindin | ng/ml | — | <5.0 | — | <2.6 | 4.2 | 233 |
| Clusterin | μg/ml | 86 | 134 | 37 | 152 | — | <0.089 |
| CTGF | ng/ml | 2.8 | 7.5 | — | <8.2 | — | <0.90 |
| GST-alpha | ng/ml | 6.7 | 62 | 1.2 | 52 | — | <26 |

TABLE 1-continued

Normal Concentration Ranges In Human Plasma, Serum, and Urine Samples

| Analyte | Units | Plasma low | Plasma high | Sera low | Sera high | Urine low | Urine high |
|---|---|---|---|---|---|---|---|
| KIM-1 | ng/ml | 0.053 | 0.57 | — | <0.35 | 0.023 | 0.67 |
| VEGF | pg/ml | 222 | 855 | 219 | 1630 | 69 | 517 |
| B2M | μg/ml | 0.68 | 2.2 | 1.00 | 2.6 | — | <0.17 |
| Cyst C | ng/ml | 608 | 1170 | 476 | 1250 | 3.9 | 79 |
| NGAL | ng/ml | 89 | 375 | 102 | 822 | 2.9 | 81 |
| OPN | ng/ml | 4.1 | 25 | 0.49 | 12 | 291 | 6130 |
| TIMP-1 | ng/ml | 50 | 131 | 100 | 246 | — | <3.9 |
| A1M | μg/ml | 6.2 | 16 | 5.7 | 17 | — | <4.2 |
| THP | μg/ml | 0.0084 | 0.052 | 0.0079 | 0.053 | 0.39 | 2.6 |
| TFF3 | μg/ml | 0.040 | 0.49 | 0.021 | 0.17 | — | <21 |
| Creatinine | mg/dL | — | — | — | — | 13 | 212 |
| Microalbumin | μg/ml | — | — | — | — | — | >16 |

In one embodiment, the high values shown for each of the biomarker analytes in Table 1 for the analytic concentrations in human plasma, sera and urine are the minimum diagnostics values for the analytes in human plasma, sera, and urine, respectively. In one exemplary embodiment, the minimum diagnostic concentration in human plasma of alpha-1 microglobulin is about 16 μg/ml, beta-2 microglobulin is about 2.2 μg/ml, calbindin is greater than about 5 ng/ml, clusterin is about 134 μg/ml, CTGF is about 16 ng/ml, cystatin C is about 1170 ng/ml, GST-alpha is about 62 ng/ml, KIM-1 is about 0.57 ng/ml, NGAL is about 375 ng/ml, osteopontin is about 25 ng/ml, THP is about 0.052 μg/ml, TIMP-1 is about 131 ng/ml, TFF-3 is about 0.49 μg/ml, and VEGF is about 855 pg/ml.

In another exemplary embodiment, the minimum diagnostic concentration in human sera of alpha-1 microglobulin is about 17 μg/ml, beta-2 microglobulin is about 2.6 μg/ml, calbindin is greater than about 2.6 ng/ml, clusterin is about 152 μg/ml, CTGF is greater than about 8.2 ng/ml, cystatin C is about 1250 ng/ml, GST-alpha is about 52 ng/ml, KIM-1 is greater than about 0.35 ng/ml, NGAL is about 822 ng/ml, osteopontin is about 12 ng/ml, THP is about 0.053 μg/ml, TIMP-1 is about 246 ng/ml, TFF-3 is about 0.17 μg/ml, and VEGF is about 1630 pg/ml.

In yet another exemplary embodiment, the minimum diagnostic concentration in human urine of alpha-1 microglobulin is about 233 μg/ml, beta-2 microglobulin is greater than about 0.17 μg/ml, calbindin is about 233 ng/ml, clusterin is greater than about 0.089 μg/ml, CTGF is greater than about 0.90 ng/ml, cystatin C is about 1170 ng/ml, GST-alpha is greater than about 26 ng/ml, KIM-1 is about 0.67 ng/ml, NGAL is about 81 ng/ml, osteopontin is about 6130 ng/ml, THP is about 2.6 μg/ml, TIMP-1 is greater than about 3.9 ng/ml, TFF-3 is greater than about 21 μg/ml, and VEGF is about 517 pg/ml.

In one embodiment, the minimum diagnostic concentrations represent the maximum level of analyte concentrations falling within an expected normal range. Obstructive uropathy or an associated disorder may be indicated if the concentration of an analyte is higher than the minimum diagnostic concentration for the analyte.

If diminished concentrations of a particular analyte are known to be associated with obstructive uropathy or an associated disorder, the minimum diagnostic concentration may not be an appropriate diagnostic criterion for identifying obstructive uropathy or an associated disorder indicated by the sample analyte concentrations. In these cases, a maximum diagnostic concentration may define the limit between the expected normal concentration range for the analyte and a sample concentration reflective of obstructive uropathy or an associated disorder. In those cases in which a maximum diagnostic concentration is the appropriate diagnostic criterion, sample concentrations that fall below a maximum diagnostic concentration may indicate obstructive uropathy or an associated disorder.

A critical feature of the method of the multiplexed analyte panel is that a combination of sample analyte concentrations may be used to diagnose obstructive uropathy or an associated disorder. In addition to comparing subsets of the biomarker analyte concentrations to diagnostic criteria, the analytes may be algebraically combined and compared to corresponding diagnostic criteria. In one embodiment, two or more sample analyte concentrations may be added and/or subtracted to determine a combined analyte concentration. In another embodiment, two or more sample analyte concentrations may be multiplied and/or divided to determine a combined analyte concentration. To identify obstructive uropathy or an associated disorder, the combined analyte concentration may be compared to a diagnostic criterion in which the corresponding minimum or maximum diagnostic concentrations are combined using the same algebraic operations used to determine the combined analyte concentration.

In yet another embodiment, the analyte concentration measured from a test sample containing one type of body fluid may be algebraically combined with an analyte concentration measured from a second test sample containing a second type of body fluid to determine a combined analyte concentration. For example, the ratio of urine calbindin to plasma calbindin may be determined and compared to a corresponding minimum diagnostic urine:plasma calbindin ratio to identify a particular renal disorder.

A variety of methods known in the art may be used to define the diagnostic criteria used to identify obstructive uropathy or an associated disorder. In one embodiment, any sample concentration falling outside the expected normal range indicates obstructive uropathy or an associated disorder. In another embodiment, the multiplexed analyte panel may be used to evaluate the analyte concentrations in test samples taken from a population of patients having obstructive uropathy or an associated disorder and compared to the normal expected analyte concentration ranges. In this same embodiment, any sample analyte concentrations that are significantly higher or lower than the expected normal concentration range may be used to define a minimum or maximum diagnostic concentration, respectively. A number of studies comparing the biomarker concentration ranges of a population of patients having a renal disorder to the corresponding analyte concentrations from a population of normal healthy subjects are described in the examples section below.

In an exemplary embodiment, an analyte value in a test sample higher than the minimum diagnostic value for the top 3 analytes of the particular sample type (e.g. plasma, urine, etc.), wherein the top 3 are determined by the random forest classification method may result in a diagnosis of obstructive uropathy.

VI. Automated Method for Diagnosing, Monitoring, or Determining a Renal Disorder In one embodiment, a system for diagnosing, monitoring, or determining obstructive uropathy or an associated disorder in a mammal is provided that includes a database to store a plurality of renal disorder database entries, and a processing device that includes the modules of a renal disorder determining application. In this embodiment, the modules are executable by the processing device, and include an analyte input module, a comparison module, and an analysis module.

The analyte input module receives three or more sample analyte concentrations that include the biomarker analytes. In one embodiment, the sample analyte concentrations are entered as input by a user of the application. In another embodiment, the sample analyte concentrations are transmitted directly to the analyte input module by the sensor device used to measure the sample analyte concentration via a data cable, infrared signal, wireless connection or other methods of data transmission known in the art.

The comparison module compares each sample analyte concentration to an entry of a renal disorder database. Each entry of the renal disorder database includes a list of minimum diagnostic concentrations reflective of a particular renal disorder. The entries of the renal disorder database may further contain additional minimum diagnostic concentrations to further define diagnostic criteria including but not limited to minimum diagnostic concentrations for additional types of bodily fluids, additional types of mammals, and severities of a particular disorder.

The analysis module determines a most likely renal disorder by combining the particular renal disorders identified by the comparison module for all of the sample analyte concentrations. In one embodiment, the most likely renal disorder is the particular renal disorder from the database entry having the most minimum diagnostic concentrations that are less than the corresponding sample analyte concentrations. In another embodiment, the most likely renal disorder is the particular renal disorder from the database entry having minimum diagnostic concentrations that are all less than the corresponding sample analyte concentrations. In yet other embodiments, the analysis module combines the sample analyte concentrations algebraically to calculate a combined sample analyte concentration that is compared to a combined minimum diagnostic concentration calculated from the corresponding minimum diagnostic criteria using the same algebraic operations. Other combinations of sample analyte concentrations from within the same test sample, or combinations of sample analyte concentrations from two or more different test samples containing two or more different bodily fluids may be used to determine a particular renal disorder in still other embodiments.

The system includes one or more processors and volatile and/or nonvolatile memory and can be embodied by or in one or more distributed or integrated components or systems. The system may include computer readable media (CRM) on which one or more algorithms, software, modules, data, and/or firmware is loaded and/or operates and/or which operates on the one or more processors to implement the systems and methods identified herein. The computer readable media may include volatile media, nonvolatile media, removable media, non-removable media, and/or other media or mediums that can be accessed by a general purpose or special purpose computing device. For example, computer readable media may include computer storage media and communication media, including but not limited to computer readable media. Computer storage media further may include volatile, non-volatile, removable, and/or non-removable media implemented in a method or technology for storage of information, such as computer readable instructions, data structures, program modules, and/or other data. Communication media may, for example, embody computer readable instructions, data structures, program modules, algorithms, and/or other data, including but not limited to as or in a modulated data signal. The communication media may be embodied in a carrier wave or other transport mechanism and may include an information delivery method. The communication media may include wired and wireless connections and technologies and may be used to transmit and/or receive wired or wireless communications. Combinations and/or sub-combinations of the above and systems, components, modules, and methods and processes described herein may be made.

The following examples are included to demonstrate preferred embodiments of the invention.

EXAMPLES

The following examples illustrate various iterations of the invention.

Example 1

Least Detectable Dose and Lower Limit of Quantitation of Assay for Analytes Associated with Renal Disorders To assess the least detectable doses (LDD) and lower limits of quantitation (LLOQ) of a variety of analytes associated with renal disorders, the following experiment was conducted. The analytes measured were alpha-1 microglobulin (A1M), beta-2 microglobulin (B2M), calbindin, clusterin, CTGF, cystatin C, GST-alpha, KIM-1, NGAL, osteopontin (OPN), THP, TIMP-1, TFF-3, and VEGF.

The concentrations of the analytes were measured using a capture-sandwich assay using antigen-specific antibodies. For each analyte, a range of standard sample dilutions ranging over about four orders of magnitude of analyte concentration were measured using the assay in order to obtain data used to construct a standard dose response curve. The dynamic range for each of the analytes, defined herein as the range of analyte concentrations measured to determine its dose response curve, is presented below.

To perform the assay, 5 µL of a diluted mixture of capture-antibody microspheres were mixed with 5 µL of blocker and 10 µL of pre-diluted standard sample in each of the wells of a hard-bottom microtiter plate. After incubating the hard-bottom plate for 1 hour, 10 µL of biotinylated detection antibody was added to each well, and then the hard-bottom plate was incubated for an additional hour. 10 µL of diluted streptavidin-phycoerythrin was added to each well and then the hard-bottom plate was incubated for another 60 minutes.

A filter-membrane microtiter plate was pre-wetted by adding 100 µL wash buffer, and then aspirated using a vacuum manifold device. The contents of the wells of the hard-bottom plate were then transferred to the corresponding wells of the filter-membrane plate. All wells of the hard-bottom plate were vacuum-aspirated and the contents were washed twice with 100 μL of wash buffer. After the second wash, 100 μL of wash buffer was added to each well, and then the washed microspheres were resuspended with thorough mixing. The plate was then analyzed using a Luminex 100 Analyzer (Luminex Corporation, Austin, Tex., USA). Dose response curves were constructed for each analyte by curve-fitting the median fluorescence intensity (MFI) measured from the assays of diluted standard samples containing a range of analyte concentrations.

The least detectable dose (LDD) was determined by adding three standard deviations to the average of the MFI signal measured for 20 replicate samples of blank standard solution (i.e. standard solution containing no analyte). The MFI signal was converted to an LDD concentration using the dose response curve and multiplied by a dilution factor of 2.

The lower limit of quantification (LLOQ), defined herein as the point at which the coefficient of variation (CV) for the analyte measured in the standard samples was 30%, was determined by the analysis of the measurements of increasingly diluted standard samples. For each analyte, the standard solution was diluted by 2 fold for 8 dilutions. At each stage of dilution, samples were assayed in triplicate, and the CV of the analyte concentration at each dilution was calculated and plotted as a function of analyte concentration. The LLOQ was interpolated from this plot and multiplied by a dilution factor of 2.

The LDD and LLOQ results for each analyte are summarized in Table 2:

TABLE 2

LDD, LLOQ, and Dynamic Range of Analyte Assay

| Analyte | Units | LDD | LLOQ | Dynamic Range minimum | Dynamic Range maximum |
|---|---|---|---|---|---|
| Calbindin | ng/mL | 1.1 | 3.1 | 0.516 | 2580 |
| Clusterin | ng/mL | 2.4 | 2.3 | 0.676 | 3378 |
| CTGF | ng/mL | 1.3 | 3.8 | 0.0794 | 400 |
| GST-alpha | ng/mL | 1.4 | 3.6 | 0.24 | 1,200 |
| KIM-1 | ng/mL | 0.016 | 0.028 | 0.00478 | 24 |
| VEGF | pg/mL | 4.4 | 20 | 8.76 | 44,000 |
| β-2 M | μg/mL | 0.012 | 0.018 | 0.0030 | 15 |
| Cystatin C | ng/mL | 2.8 | 3.7 | 0.60 | 3,000 |
| NGAL | ng/mL | 4.1 | 7.8 | 1.2 | 6,000 |
| Osteopontin | ng/mL | 29 | 52 | 3.9 | 19,500 |
| TIMP-1 | ng/mL | 0.71 | 1.1 | 0.073 | 365 |
| A-1 M | μg/mL | 0.059 | 0.29 | 0.042 | 210 |
| THP | μg/mL | 0.46 | 0.30 | 0.16 | 800 |
| TFF-3 | μg/mL | 0.06 | 0.097 | 0.060 | 300 |

The results of this experiment characterized the least detectable dose and the lower limit of quantification for fourteen analytes associated with various renal disorders using a capture-sandwich assay.

Example 2

Precision of Assay for Analytes Associated with Renal Disorders

To assess the precision of an assay used to measure the concentration of analytes associated with renal disorders, the following experiment was conducted. The analytes measured were alpha-1 microglobulin (A1M), beta-2 microglobulin (B2M), calbindin, clusterin, CTGF, cystatin C, GST-alpha, KIM-1, NGAL, osteopontin (OPN), THP, TIMP-1, TFF-3, and VEGF. For each analyte, three concentration levels of standard solution were measured in triplicate during three runs using the methods described in Example 1. The percent errors for each run at each concentration are presented in Table 3 for all of the analytes tested:

TABLE 3

Precision of Analyte Assay

| Analyte | Average concentration (ng/mL) | Run 1 Error (%) | Run 2 Error (%) | Run 2 Error (%) | Interrun Error (%) |
|---|---|---|---|---|---|
| Calbindin | 4.0 | 6 | 2 | 6 | 13 |
|  | 36 | 5 | 3 | 2 | 7 |
|  | 281 | 1 | 6 | 0 | 3 |
| Clusterin | 4.4 | 4 | 9 | 2 | 6 |
|  | 39 | 5 | 1 | 6 | 8 |
|  | 229 | 1 | 3 | 0 | 2 |
| CTGF | 1.2 | 10 | 17 | 4 | 14 |
|  | 2.5 | 19 | 19 | 14 | 14 |
|  | 18 | 7 | 5 | 13 | 9 |
| GST-alpha | 3.9 | 14 | 7 | 5 | 10 |
|  | 16 | 13 | 7 | 10 | 11 |
|  | 42 | 1 | 16 | 6 | 8 |
| KIM-1 | 0.035 | 2 | 0 | 5 | 13 |
|  | 0.32 | 4 | 5 | 2 | 8 |
|  | 2.9 | 0 | 5 | 7 | 4 |
| VEGF | 65 | 10 | 1 | 6 | 14 |
|  | 534 | 9 | 2 | 12 | 7 |
|  | 5,397 | 1 | 13 | 14 | 9 |
| β-2 M | 0.040 | 6 | 1 | 8 | 5 |
|  | 0.43 | 2 | 2 | 0 | 10 |
|  | 6.7 | 6 | 5 | 11 | 6 |
| Cystatin C | 10.5 | 4 | 1 | 7 | 13 |
|  | 49 | 0 | 0 | 3 | 9 |
|  | 424 | 2 | 6 | 2 | 5 |
| NGAL | 18.1 | 11 | 3 | 6 | 13 |
|  | 147 | 0 | 0 | 6 | 5 |
|  | 1,070 | 5 | 1 | 2 | 5 |
| Osteopontin | 44 | 1 | 10 | 2 | 11 |
|  | 523 | 9 | 9 | 9 | 7 |
|  | 8,930 | 4 | 10 | 1 | 10 |
| TIMP-1 | 2.2 | 13 | 6 | 3 | 13 |
|  | 26 | 1 | 1 | 4 | 14 |
|  | 130 | 1 | 3 | 1 | 4 |
| A-1 M | 1.7 | 11 | 7 | 7 | 14 |
|  | 19 | 4 | 1 | 8 | 9 |
|  | 45 | 3 | 5 | 2 | 4 |
| THP | 9.4 | 3 | 10 | 11 | 11 |
|  | 15 | 3 | 7 | 8 | 6 |
|  | 37 | 4 | 5 | 0 | 5 |
| TFF-3 | 0.3 | 13 | 3 | 11 | 12 |
|  | 4.2 | 5 | 8 | 5 | 7 |
|  | 1.2 | 3 | 7 | 0 | 13 |

The results of this experiment characterized the precision of a capture-sandwich assay for fourteen analytes associated with various renal disorders over a wide range of analyte concentrations. The precision of the assay varied between about 1% and about 15% error within a given run, and between about 5% and about 15% error between different runs. The percent errors summarized in Table 2 provide information concerning random error to be expected in an assay measurement caused by variations in technicians, measuring instruments, and times of measurement.

Example 3

Linearity of Assay for Analytes Associated with Renal Disorders

To assess the linearity of an assay used to measure the concentration of analytes associated with renal disorders, the following experiment was conducted. The analytes measured were alpha-1 microglobulin (A1M), beta-2 microglobulin (B2M), calbindin, clusterin, CTGF, cystatin C, GST-alpha, KIM-1, NGAL, osteopontin (OPN), THP, TIMP-1, TFF-3, and VEGF. For each analyte, three concentration levels of standard solution were measured in triplicate during three runs using the methods described in Example 1. Linearity of the assay used to measure each analyte was determined by measuring the concentrations of standard samples that were serially-diluted throughout the assay range. The % recovery was calculated as observed vs. expected concentration based on the dose-response curve. The results of the linearity analysis are summarized in Table 4.

TABLE 4

Linearity of Analyte Assay

| Analyte | Dilution | Expected concentration | Observed concentration | Recovery (%) |
|---|---|---|---|---|
| Calbindin | 1:2 | 61 | 61 | 100 |
| (ng/mL) | 1:4 | 30 | 32 | 106 |
| | 1:8 | 15 | 17 | 110 |
| Clusterin | 1:2 | 41 | 41 | 100 |
| (ng/mL) | 1:4 | 21 | 24 | 116 |
| | 1:8 | 10 | 11 | 111 |
| CTGF | 1:2 | 1.7 | 1.7 | 100 |
| (ng/mL) | 1:4 | 0.84 | 1.0 | 124 |
| | 1:8 | 0.42 | 0.51 | 122 |
| GST-alpha | 1:2 | 25 | 25 | 100 |
| (ng/mL) | 1:4 | 12 | 14 | 115 |
| | 1:8 | 6.2 | 8.0 | 129 |
| KIM-1 | 1:2 | 0.87 | 0.87 | 100 |
| (ng/mL) | 1:4 | 0.41 | 0.41 | 101 |
| | 1:8 | 0.21 | 0.19 | 93 |
| VEGF | 1:2 | 2,525 | 2,525 | 100 |
| (pg/mL) | 1:4 | 1,263 | 1,340 | 106 |
| | 1:8 | 631 | 686 | 109 |
| β-2M | 1:100 | 0.63 | 0.63 | 100 |
| (µg/mL) | 1:200 | 0.31 | 0.34 | 106 |
| | 1:400 | 0.16 | 0.17 | 107 |
| Cystatin C | 1:100 | 249 | 249 | 100 |
| (ng/mL) | 1:200 | 125 | 122 | 102 |
| | 1:400 | 62 | 56 | 110 |
| NGAL | 1:100 | 1,435 | 1,435 | 100 |
| (ng/mL) | 1:200 | 718 | 775 | 108 |
| | 1:400 | 359 | 369 | 103 |
| Osteopontin | 1:100 | 6,415 | 6,415 | 100 |
| (ng/mL) | 1:200 | 3,208 | 3,275 | 102 |
| | 1:400 | 1,604 | 1,525 | 95 |
| TIMP-1 | 1:100 | 35 | 35 | 100 |
| (ng/mL) | 1:200 | 18 | 18 | 100 |
| | 1:400 | 8.8 | 8.8 | 100 |
| A-1M | 1:2000 | 37 | 37 | 100 |
| (µg/mL) | 1:4000 | 18 | 18 | 99 |
| | 1:8000 | 9.1 | 9.2 | 99 |
| THP | 1:2000 | 28 | 28 | 100 |
| (µg/mL) | 1:4000 | 14 | 14 | 96 |
| | 1:8000 | 6.7 | 7.1 | 94 |
| TFF-3 | 1:2000 | 8.8 | 8.8 | 100 |
| (µg/mL) | 1:4000 | 3.8 | 4.4 | 86 |
| | 1:8000 | 1.9 | 2.2 | 86 |

The results of this experiment demonstrated reasonably linear responses of the sandwich-capture assay to variations in the concentrations of the analytes in the tested samples.

Example 4

Spike Recovery of Analytes Associated with Renal Disorders

To assess the recovery of analytes spiked into urine, serum, and plasma samples by an assay used to measure the concentration of analytes associated with renal disorders, the following experiment was conducted. The analytes measured were alpha-1 microglobulin (A1M), beta-2 microglobulin (B2M), calbindin, clusterin, CTGF, cystatin C, GST-alpha, KIM-1, NGAL, osteopontin (OPN), THP, TIMP-1, TFF-3, and VEGF. For each analyte, three concentration levels of standard solution were spiked into known urine, serum, and plasma samples. Prior to analysis, all urine samples were diluted 1:2000 (sample: diluent), all plasma samples were diluted 1:5 (sample: diluent), and all serum samples were diluted 1:2000 (sample: diluent).

The concentrations of the analytes in the samples were measured using the methods described in Example 1. The average % recovery was calculated as the proportion of the measurement of analyte spiked into the urine, serum, or plasma sample (observed) to the measurement of analyte spiked into the standard solution (expected). The results of the spike recovery analysis are summarized in Table 5.

TABLE 5

Spike Recovery of Analyte Assay in Urine, Serum, and Plasma Samples

| Analyte | Spike Concentration | Recovery in Urine Sample (%) | Recovery in Serum Sample (%) | Recovery in Plasma Sample (%) |
|---|---|---|---|---|
| Calbindin | 66 | 76 | 82 | 83 |
| (ng/mL) | 35 | 91 | 77 | 71 |
| | 18 | 80 | 82 | 73 |
| | average | 82 | 80 | 76 |
| Clusterin | 80 | 72 | 73 | 75 |
| (ng/mL) | 37 | 70 | 66 | 72 |
| | 20 | 90 | 73 | 70 |
| | average | 77 | 70 | 72 |
| CTGF | 8.4 | 91 | 80 | 79 |
| (ng/mL) | 4.6 | 114 | 69 | 78 |
| | 2.4 | 76 | 80 | 69 |
| | average | 94 | 77 | 75 |
| GST-alpha | 27 | 75 | 84 | 80 |
| (ng/mL) | 15 | 90 | 75 | 81 |
| | 7.1 | 82 | 84 | 72 |
| | average | 83 | 81 | 78 |
| KIM-1 | 0.63 | 87 | 80 | 83 |
| (ng/mL) | .029 | 119 | 74 | 80 |
| | 0.14 | 117 | 80 | 78 |
| | average | 107 | 78 | 80 |
| VEGF | 584 | 88 | 84 | 82 |
| (pg/mL) | 287 | 101 | 77 | 86 |
| | 123 | 107 | 84 | 77 |
| | average | 99 | 82 | 82 |
| β-2M | 0.97 | 117 | 98 | 98 |
| (µg/mL) | 0.50 | 124 | 119 | 119 |
| | 0.24 | 104 | 107 | 107 |
| | average | 115 | 108 | 105 |
| Cystatin C | 183 | 138 | 80 | 103 |
| (ng/mL) | 90 | 136 | 97 | 103 |
| | 40 | 120 | 97 | 118 |
| | average | 131 | 91 | 108 |
| NGAL | 426 | 120 | 105 | 111 |
| (ng/mL) | 213 | 124 | 114 | 112 |
| | 103 | 90 | 99 | 113 |
| | average | 111 | 106 | 112 |
| Osteopontin | 1,245 | 204 | 124 | 68 |
| (ng/mL) | 636 | 153 | 112 | 69 |
| | 302 | 66 | 103 | 67 |
| | average | 108 | 113 | 68 |
| TIMP-1 | 25 | 98 | 97 | 113 |
| (ng/mL) | 12 | 114 | 89 | 103 |
| | 5.7 | 94 | 99 | 113 |
| | average | 102 | 95 | 110 |
| A-1M | 0.0028 | 100 | 101 | 79 |
| (µg/mL) | 0.0012 | 125 | 80 | 81 |
| | 0.00060 | 118 | 101 | 82 |
| | average | 114 | 94 | 81 |
| THP | 0.0096 | 126 | 108 | 90 |
| (µg/mL) | 0.0047 | 131 | 93 | 91 |
| | 0.0026 | 112 | 114 | 83 |
| | average | 123 | 105 | 88 |

TABLE 5-continued

Spike Recovery of Analyte Assay in Urine, Serum, and Plasma Samples

| Analyte | Spike Concentration | Recovery in Urine Sample (%) | Recovery in Serum Sample (%) | Recovery in Plasma Sample (%) |
|---|---|---|---|---|
| TFF-3 (µg/mL) | 0.0038 | 105 | 114 | 97 |
| | 0.0019 | 109 | 104 | 95 |
| | 0.0010 | 102 | 118 | 93 |
| | average | 105 | 112 | 95 |

The results of this experiment demonstrated that the sandwich-type assay is reasonably sensitive to the presence of all analytes measured, whether the analytes were measured in standard samples, urine samples, plasma samples, or serum samples.

Example 5

Matrix Interferences of Analytes Associated with Renal Disorders

To assess the matrix interference of hemoglobin, bilirubin, and triglycerides spiked into standard samples, the following experiment was conducted. The analytes measured were alpha-1 microglobulin (A1M), beta-2 microglobulin (B2M), calbindin, clusterin, CTGF, cystatin C, GST-alpha, KIM-1, NGAL, osteopontin (OPN), THP, TIMP-1, TFF-3, and VEGF. For each analyte, three concentration levels of standard solution were spiked into known urine, serum, and plasma samples. Matrix interference was assessed by spiking hemoglobin, bilirubin, and triglyceride into standard analyte samples and measuring analyte concentrations using the methods described in Example 1. A % recovery was determined by calculating the ratio of the analyte concentration measured from the spiked sample (observed) divided by the analyte concentration measured form the standard sample (expected). The results of the matrix interference analysis are summarized in Table 6.

TABLE 6

Matrix Interference of Hemoglobin, Bilirubin, and Triglyceride on the Measurement of Analytes

| Analyte | Matrix Compound Spiked into Sample | Maximum Spike Concentration | Overall Recovery (%) |
|---|---|---|---|
| Calbindin (mg/mL) | Hemoglobin | 500 | 110 |
| | Bilirubin | 20 | 98 |
| | Triglyceride | 500 | 117 |
| Clusterin (mg/mL) | Hemoglobin | 500 | 125 |
| | Bilirubin | 20 | 110 |
| | Triglyceride | 500 | 85 |
| CTGF (mg/mL) | Hemoglobin | 500 | 91 |
| | Bilirubin | 20 | 88 |
| | Triglyceride | 500 | 84 |
| GST-alpha (mg/mL) | Hemoglobin | 500 | 100 |
| | Bilirubin | 20 | 96 |
| | Triglyceride | 500 | 96 |
| KIM-1 (mg/mL) | Hemoglobin | 500 | 108 |
| | Bilirubin | 20 | 117 |
| | Triglyceride | 500 | 84 |
| VEGF (mg/mL) | Hemoglobin | 500 | 112 |
| | Bilirubin | 20 | 85 |
| | Triglyceride | 500 | 114 |
| β-2M (µg/mL) | Hemoglobin | 500 | 84 |
| | Bilirubin | 20 | 75 |
| | Triglyceride | 500 | 104 |
| Cystatin C (ng/mL) | Hemoglobin | 500 | 91 |
| | Bilirubin | 20 | 102 |
| | Triglyceride | 500 | 124 |
| NGAL (ng/mL) | Hemoglobin | 500 | 99 |
| | Bilirubin | 20 | 92 |
| | Triglyceride | 500 | 106 |
| Osteopontin (ng/mL) | Hemoglobin | 500 | 83 |
| | Bilirubin | 20 | 86 |
| | Triglyceride | 500 | 106 |
| TIMP-1 (ng/mL) | Hemoglobin | 500 | 87 |
| | Bilirubin | 20 | 86 |
| | Triglyceride | 500 | 93 |
| A-1M (µg/mL) | Hemoglobin | 500 | 103 |
| | Bilirubin | 20 | 110 |
| | Triglyceride | 500 | 112 |
| THP (µg/mL) | Hemoglobin | 500 | 108 |
| | Bilirubin | 20 | 101 |
| | Triglyceride | 500 | 121 |
| TFF-3 (µg/mL) | Hemoglobin | 500 | 101 |
| | Bilirubin | 20 | 101 |
| | Triglyceride | 500 | 110 |

The results of this experiment demonstrated that hemoglobin, bilirubin, and triglycerides, three common compounds found in urine, plasma, and serum samples, did not significantly degrade the ability of the sandwich-capture assay to detect any of the analytes tested.

Example 6

Sample Stability of Analytes Associated with Renal Disorders

To assess the ability of analytes spiked into urine, serum, and plasma samples to tolerate freeze-thaw cycles, the following experiment was conducted. The analytes measured were alpha-1 microglobulin (A1M), beta-2 microglobulin (B2M), calbindin, clusterin, CTGF, cystatin C, GST-alpha, KIM-1, NGAL, osteopontin (OPN), THP, TIMP-1, TFF-3, and VEGF. Each analyte was spiked into known urine, serum, and plasma samples at a known analyte concentration. The concentrations of the analytes in the samples were measured using the methods described in Example 1 after the initial addition of the analyte, and after one, two and three cycles of freezing and thawing. In addition, analyte concentrations in urine, serum and plasma samples were measured immediately after the addition of the analyte to the samples as well as after storage at room temperature for two hours and four hours, and after storage at 4° C. for 2 hours, four hours, and 24 hours.

The results of the freeze-thaw stability analysis are summarized in Table 7. The % recovery of each analyte was calculated as a percentage of the analyte measured in the sample prior to any freeze-thaw cycles.

TABLE 7

Freeze-Thaw Stability of the Analytes in Urine, Serum, and Plasma

| Analyte | Period and Temp | Urine Sample Concentration | Recovery (%) | Serum Sample Concentration | Recovery (%) | Plasma Sample Concentration | Recovery (%) |
|---|---|---|---|---|---|---|---|
| Calbindin (ng/mL) | Control | 212 | 100 | 31 | 100 | 43 | 100 |
|  | 1X | 221 | 104 | 30 | 96 | 41 | 94 |
|  | 2X | 203 | 96 | 30 | 99 | 39 | 92 |
|  | 3X | 234 | 110 | 30 | 97 | 40 | 93 |
| Clusterin (ng/mL) | 0 | 315 | 100 | 232 | 100 | 187 | 100 |
|  | 1X | 329 | 104 | 227 | 98 | 177 | 95 |
|  | 2X | 341 | 108 | 240 | 103 | 175 | 94 |
|  | 3X | 379 | 120 | 248 | 107 | 183 | 98 |
| CTGF (ng/mL) | 0 | 6.7 | 100 | 1.5 | 100 | 1.2 | 100 |
|  | 1X | 7.5 | 112 | 1.3 | 82 | 1.2 | 94 |
|  | 2X | 6.8 | 101 | 1.4 | 90 | 1.2 | 100 |
|  | 3X | 7.7 | 115 | 1.2 | 73 | 1.3 | 107 |
| GST-alpha (ng/mL) | 0 | 12 | 100 | 23 | 100 | 11 | 100 |
|  | 1X | 13 | 104 | 24 | 105 | 11 | 101 |
|  | 2X | 14 | 116 | 21 | 92 | 11 | 97 |
|  | 3X | 14 | 111 | 23 | 100 | 12 | 108 |
| KIM-1 (ng/mL) | 0 | 1.7 | 100 | 0.24 | 100 | 0.24 | 100 |
|  | 1X | 1.7 | 99 | 0.24 | 102 | 0.22 | 91 |
|  | 2X | 1.7 | 99 | 0.22 | 94 | 0.19 | 78 |
|  | 3X | 1.8 | 107 | 0.23 | 97 | 0.22 | 93 |
| VEGF (pg/mL) | 0 | 1,530 | 100 | 1,245 | 100 | 674 | 100 |
|  | 1X | 1,575 | 103 | 1,205 | 97 | 652 | 97 |
|  | 2X | 1,570 | 103 | 1,140 | 92 | 612 | 91 |
|  | 3X | 1,700 | 111 | 1,185 | 95 | 670 | 99 |
| β-2 M (μg/mL) | 0 | 0.0070 | 100 | 1.2 | 100 | 15 | 100 |
|  | 1X | 0.0073 | 104 | 1.1 | 93 | 14 | 109 |
|  | 2X | 0.0076 | 108 | 1.2 | 103 | 15 | 104 |
|  | 3X | 0.0076 | 108 | 1.1 | 97 | 13 | 116 |
| Cystatin C (ng/mL) | 0 | 1,240 | 100 | 1,330 | 100 | 519 | 100 |
|  | 1X | 1,280 | 103 | 1,470 | 111 | 584 | 113 |
|  | 2X | 1,410 | 114 | 1,370 | 103 | 730 | 141 |
|  | 3X | 1,420 | 115 | 1,380 | 104 | 589 | 113 |
| NGAL (ng/mL) | 0 | 45 | 100 | 245 | 100 | 84 | 100 |
|  | 1X | 46 | 102 | 179 | 114 | 94 | 112 |
|  | 2X | 47 | 104 | 276 | 113 | 91 | 108 |
|  | 3X | 47 | 104 | 278 | 113 | 91 | 109 |
| Osteopontin (ng/mL) | 0 | 38 | 100 | 1.7 | 100 | 5.0 | 100 |
|  | 1X | 42 | 110 | 1.8 | 102 | 5.5 | 110 |
|  | 2X | 42 | 108 | 1.5 | 87 | 5.5 | 109 |
|  | 3X | 42 | 110 | 1.3 | 77 | 5.4 | 107 |
| TIMP-1 (ng/mL) | 0 | 266 | 100 | 220 | 100 | 70 | 100 |
|  | 1X | 265 | 100 | 220 | 10 | 75 | 108 |
|  | 2X | 255 | 96 | 215 | 98 | 77 | 110 |
|  | 3X | 295 | 111 | 228 | 104 | 76 | 109 |
| A-1 M (μg/mL) | 0 | 14 | 100 | 26 | 100 | 4.5 | 100 |
|  | 1X | 13 | 92 | 25 | 96 | 4.2 | 94 |
|  | 2X | 15 | 107 | 25 | 96 | 4.3 | 97 |
|  | 3X | 16 | 116 | 23 | 88 | 4.0 | 90 |
| THP (μg/mL) | 0 | 4.6 | 100 | 31 | 100 | 9.2 | 100 |
|  | 1X | 4.4 | 96 | 31 | 98 | 8.8 | 95 |
|  | 2X | 5.0 | 110 | 31 | 100 | 9.2 | 100 |
|  | 3X | 5.2 | 114 | 27 | 85 | 9.1 | 99 |
| TFF-3 (μg/mL) | 0 | 4.6 | 100 | 24 | 100 | 22 | 100 |
|  | 1X | 4.4 | 96 | 23 | 98 | 22 | 103 |
|  | 2X | 5.0 | 110 | 24 | 103 | 22 | 101 |
|  | 3X | 5.2 | 114 | 19 | 82 | 22 | 102 |

The results of the short-term stability assessment are summarized in Table 8. The % recovery of each analyte was calculated as a percentage of the analyte measured in the sample prior to any short-term storage.

TABLE 8

Short-Term Stability of Analytes in Urine, Serum, and Plasma

| Analyte | Storage Time/Temp | Urine Sample Sample Conc. | Urine Sample Recovery (%) | Serum Sample Sample Conc. | Serum Sample Recovery (%) | Plasma Sample Sample Conc. | Plasma Sample Recovery (%) |
| --- | --- | --- | --- | --- | --- | --- | --- |
| Calbindin (ng/mL) | Control | 226 | 100 | 33 | 100 | 7 | 100 |
| | 2 hr/room temp | 242 | 107 | 30 | 90 | 6.3 | 90 |
| | 2 hr. @ 4° C. | 228 | 101 | 29 | 89 | 6.5 | 93 |
| | 4 hr @ room temp | 240 | 106 | 28 | 84 | 5.6 | 79 |
| | 4 hr. @ 4° C. | 202 | 89 | 29 | 86 | 5.5 | 79 |
| | 24 hr. @ 4° C. | 199 | 88 | 26 | 78 | 7.1 | 101 |
| Clusterin (ng/mL) | Control | 185 | 100 | 224 | 100 | 171 | 100 |
| | 2 hr @ room temp | 173 | 94 | 237 | 106 | 180 | 105 |
| | 2 hr. @ 4° C. | 146 | 79 | 225 | 100 | 171 | 100 |
| | 4 hr @ room temp | 166 | 89 | 214 | 96 | 160 | 94 |
| | 4 hr. @ 4° C. | 157 | 85 | 198 | 88 | 143 | 84 |
| | 24 hr. @ 4° C. | 185 | 100 | 207 | 92 | 162 | 94 |
| CTGF (ng/mL) | Control | 1.9 | 100 | 8.8 | 100 | 1.2 | 100 |
| | 2 hr @ room temp | 1.9 | 99 | 6.7 | 76 | 1 | 83 |
| | 2 hr. @ 4° C. | 1.8 | 96 | 8.1 | 92 | 1.1 | 89 |
| | 4 hr @ room temp | 2.1 | 113 | 5.6 | 64 | 1 | 84 |
| | 4 hr. @ 4° C. | 1.7 | 91 | 6.4 | 74 | 0.9 | 78 |
| | 24 hr. @ 4° C. | 2.2 | 116 | 5.9 | 68 | 1.1 | 89 |
| GST-alpha (ng/mL) | Control | 14 | 100 | 21 | 100 | 11 | 100 |
| | 2 hr @ room temp | 11 | 75 | 23 | 107 | 11 | 103 |
| | 2 hr. @ 4° C. | 13 | 93 | 22 | 104 | 9.4 | 90 |
| | 4 hr @ room temp | 11 | 79 | 21 | 100 | 11 | 109 |
| | 4 hr. @ 4° C. | 12 | 89 | 21 | 98 | 11 | 100 |
| | 24 hr. @ 4° C. | 13 | 90 | 22 | 103 | 14 | 129 |
| KIM-1 (ng/mL) | Control | 1.5 | 100 | 0.23 | 100 | 0.24 | 100 |
| | 2 hr @ room temp | 1.2 | 78 | 0.2 | 86 | 0.22 | 90 |
| | 2 hr. @ 4° C. | 1.6 | 106 | 0.23 | 98 | 0.21 | 85 |
| | 4 hr @ room temp | 1.3 | 84 | 0.19 | 82 | 0.2 | 81 |
| | 4 hr. @ 4° C. | 1.4 | 90 | 0.22 | 93 | 0.19 | 80 |
| | 24 hr. @ 4° C. | 1.1 | 76 | 0.18 | 76 | 0.23 | 94 |
| VEGF (pg/mL) | Control | 851 | 100 | 1215 | 100 | 670 | 100 |
| | 2 hr @ room temp | 793 | 93 | 1055 | 87 | 622 | 93 |
| | 2 hr. @ 4° C. | 700 | 82 | 1065 | 88 | 629 | 94 |
| | 4 hr @ room temp | 704 | 83 | 1007 | 83 | 566 | 84 |
| | 4 hr. @ 4° C. | 618 | 73 | 1135 | 93 | 544 | 81 |
| | 24 hr. @ 4° C. | 653 | 77 | 1130 | 93 | 589 | 88 |

TABLE 8-continued

Short-Term Stability of Analytes in Urine, Serum, and Plasma

| Analyte | Storage Time/Temp | Urine Sample Sample Conc. | Urine Sample Recovery (%) | Serum Sample Sample Conc. | Serum Sample Recovery (%) | Plasma Sample Sample Conc. | Plasma Sample Recovery (%) |
|---|---|---|---|---|---|---|---|
| β-2 M (μg/mL) | Control | 0.064 | 100 | 2.6 | 100 | 1.2 | 100 |
| | 2 hr @ room temp | 0.062 | 97 | 2.4 | 92 | 1.1 | 93 |
| | 2 hr. @ 4° C. | 0.058 | 91 | 2.2 | 85 | 1.2 | 94 |
| | 4 hr @ room temp | 0.064 | 101 | 2.2 | 83 | 1.2 | 94 |
| | 4 hr. @ 4° C. | 0.057 | 90 | 2.2 | 85 | 1.2 | 98 |
| | 24 hr. @ 4° C. | 0.06 | 94 | 2.5 | 97 | 1.3 | 103 |
| Cystatin C (ng/mL) | Control | 52 | 100 | 819 | 100 | 476 | 100 |
| | 2 hr @ room temp | 50 | 96 | 837 | 102 | 466 | 98 |
| | 2 hr. @ 4° C. | 44 | 84 | 884 | 108 | 547 | 115 |
| | 4 hr @ room temp | 49 | 93 | 829 | 101 | 498 | 105 |
| | 4 hr. @ 4° C. | 46 | 88 | 883 | 108 | 513 | 108 |
| | 24 hr. @ 4° C. | 51 | 97 | 767 | 94 | 471 | 99 |
| NGAL (ng/mL) | Control | 857 | 100 | 302 | 100 | 93 | 100 |
| | 2 hr @ room temp | 888 | 104 | 287 | 95 | 96 | 104 |
| | 2 hr. @ 4° C. | 923 | 108 | 275 | 91 | 92 | 100 |
| | 4 hr @ room temp | 861 | 101 | 269 | 89 | 88 | 95 |
| | 4 hr. @ 4° C. | 842 | 98 | 283 | 94 | 94 | 101 |
| | 24 hr. @ 4° C. | 960 | 112 | 245 | 81 | 88 | 95 |
| Osteopontin (ng/mL) | Control | 2243 | 100 | 6.4 | 100 | 5.2 | 100 |
| | 2 hr @ room temp | 2240 | 100 | 6.8 | 107 | 5.9 | 114 |
| | 2 hr. @ 4° C. | 2140 | 95 | 6.4 | 101 | 6.2 | 120 |
| | 4 hr @ room temp | 2227 | 99 | 6.9 | 108 | 5.8 | 111 |
| | 4 hr. @ 4° C. | 2120 | 95 | 7.7 | 120 | 5.2 | 101 |
| | 24 hr. @ 4° C. | 2253 | 100 | 6.5 | 101 | 6 | 116 |
| TIMP-1 (ng/mL) | Control | 17 | 100 | 349 | 100 | 72 | 100 |
| | 2 hr @ room temp | 17 | 98 | 311 | 89 | 70 | 98 |
| | 2 hr. @ 4° C. | 16 | 94 | 311 | 89 | 68 | 95 |
| | 4 hr @ room temp | 17 | 97 | 306 | 88 | 68 | 95 |
| | 4 hr. @ 4° C. | 16 | 93 | 329 | 94 | 74 | 103 |
| | 24 hr. @ 4° C. | 18 | 105 | 349 | 100 | 72 | 100 |
| A-1 M (μg/mL) | Control | 3.6 | 100 | 2.2 | 100 | 1 | 100 |
| | 2 hr @ room temp | 3.5 | 95 | 2 | 92 | 1 | 105 |
| | 2 hr. @ 4° C. | 3.4 | 92 | 2.1 | 97 | 0.99 | 99 |
| | 4 hr @ room temp | 3.2 | 88 | 2.2 | 101 | 0.99 | 96 |
| | 4 hr. @ 4° C. | 3 | 82 | 2.2 | 99 | 0.97 | 98 |
| | 24 hr. @ 4° C. | 3 | 83 | 2.2 | 100 | 1 | 101 |
| THP (μg/mL) | Control | 1.2 | 100 | 34 | 100 | 2.1 | 100 |
| | 2 hr @ room temp | 1.2 | 99 | 34 | 99 | 2 | 99 |
| | 2 hr. @ 4° C. | 1.1 | 90 | 34 | 100 | 2 | 98 |
| | 4 hr @ room temp | 1.1 | 88 | 27 | 80 | 2 | 99 |

TABLE 8-continued

Short-Term Stability of Analytes in Urine, Serum, and Plasma

| Analyte | Storage Time/ Temp | Urine Sample | | Serum Sample | | Plasma Sample | |
|---|---|---|---|---|---|---|---|
| | | Sample Conc. | Recovery (%) | Sample Conc. | Recovery (%) | Sample Conc. | Recovery (%) |
| | 4 hr. @ 4° C. | 0.95 | 79 | 33 | 97 | 2 | 95 |
| | 24 hr. @ 4° C. | 0.91 | 76 | 33 | 98 | 2.4 | 116 |
| TFF-3 (µg/mL) | Control | 1230 | 100 | 188 | 100 | 2240 | 100 |
| | 2 hr @ room temp | 1215 | 99 | 179 | 95 | 2200 | 98 |
| | 2 hr. @ 4° C. | 1200 | 98 | 195 | 104 | 2263 | 101 |
| | 4 hr @ room temp | 1160 | 94 | 224 | 119 | 2097 | 94 |
| | 4 hr. @ 4° C. | 1020 | 83 | 199 | 106 | 2317 | 103 |
| | 24 hr. @ 4° C. | 1030 | 84 | 229 | 122 | 1940 | 87 |

The results of this experiment demonstrated that the analytes associated with renal disorders tested were suitably stable over several freeze/thaw cycles, and up to 24 hrs of storage at a temperature of 4° C.

Example 8

Analysis of Kidney Biomarkers in Plasma and Urine from Patients with Renal Injury A screen for potential protein biomarkers in relation to kidney toxicity/damage was performed using a panel of biomarkers, in a set of urine and plasma samples from patients with documented renal damage. The investigated patient groups included diabetic nephropathy (DN), obstructive uropathy (OU), analgesic abuse (AA) and glomerulonephritis (GN) along with age, gender and BMI matched control groups. Multiplexed immunoassays were applied in order to quantify the following protein analytes: Alpha-1 Microglobulin ($\alpha$1M), KIM-1, Microalbumin, Beta-2-Microglobulin ($\beta$2M), Calbindin, Clusterin, CystatinC, TreFoilFactor-3 (TFF-3), CTGF, GST-alpha, VEGF, Calbindin, Osteopontin, Tamm-HorsfallProtein (THP), TIMP-1 and NGAL.

Li-Heparin plasma and mid-stream spot urine samples were collected from four different patient groups. Samples were also collected from age, gender and BMI matched control subjects. 20 subjects were included in each group resulting in a total number of 160 urine and plasma samples. All samples were stored at −80° C. before use. Glomerular filtration rate for all samples was estimated using two different estimations (Modification of Diet in Renal Disease or MDRD, and the Chronic Kidney Disease Epidemiology Collaboration or CKD-EPI) to outline the eGFR (estimated glomerular filtration rate) distribution within each patient group (FIG. 1). Protein analytes were quantified in human plasma and urine using multiplexed immunoassays in the Luminex xMAP™ platform. The microsphere-based multiplex immunoassays consist of antigen-specific antibodies and optimized reagents in a capture-sandwich format. Output data was given as g/ml calculated from internal standard curves. Because urine creatinine (uCr) correlates with renal filtration rate, data analysis was performed without correction for uCr. Univariate and multivariate data analysis was performed comparing all case vs. control samples as well as cases vs. control samples for the various disease groups.

The majority of the measured proteins showed a correlation to eGFR. Measured variables were correlated to eGFR using Pearson's correlations coefficient, and samples from healthy controls and all disease groups were included in the analysis. 11 and 7 proteins displayed P-values below 0.05 for plasma and urine (Table 9) respectively.

TABLE 9

Correlation analysis of eGFR and variables for all case samples

| URINE | | | PLASMA | | |
|---|---|---|---|---|---|
| Variable | Pearson's r | P-Value | Variable | Pearson's r | P-Value |
| Alpha-1-Microglobulin | −0.08 | 0.3 | Alpha-1-Microglobulin | −0.33 | *<0.0001* |
| Beta-2-Microglobulin | −0.23 | *0.003* | Beta-2-Microglobulin | −0.39 | *<0.0001* |
| Calbindin | −0.16 | 0.04 | Calbindin | −0.18 | <0.02 |
| Clusterin | −0.07 | 0.4 | Clusterin | −0.51 | *<0.0001* |
| CTGF | −0.08 | 0.3 | CTGF | −0.05 | 0.5 |
| Creatinine | −0.32 | *<0.0001* | Cystatin-C | −0.42 | <0.0001 |
| Cystatin-C | −0.24 | *0.002* | GST-alpha | −0.12 | 0.1 |
| GST-alpha | −0.11 | 0.2 | KIM-1 | −0.17 | 0.03 |
| KIM-1 | −0.08 | 0.3 | NGAL | −0.28 | *<0.001* |
| Microalbumin_UR | −0.17 | 0.03 | Osteopontin | −0.33 | *<0.0001* |
| NGAL | −0.15 | 0.07 | THP | −0.31 | *<0.0001* |

TABLE 9-continued

Correlation analysis of eGFR and variables for all case samples

| | URINE | | | PLASMA | |
|---|---|---|---|---|---|
| Variable | Pearson's r | P-Value | Variable | Pearson's r | P-Value |
| Osteopontin | −0.19 | 0.02 | TIMP-1 | −0.28 | <0.001 |
| THP | −0.05 | 0.6 | TFF3 | −0.38 | *<0.0001* |
| TIMP-1 | −0.19 | 0.01 | VEGF | −0.14 | 0.08 |
| TFF2 | −0.09 | 0.3 | | | |
| VEGF | −0.07 | 0.4 | | | |

Figure 2A:
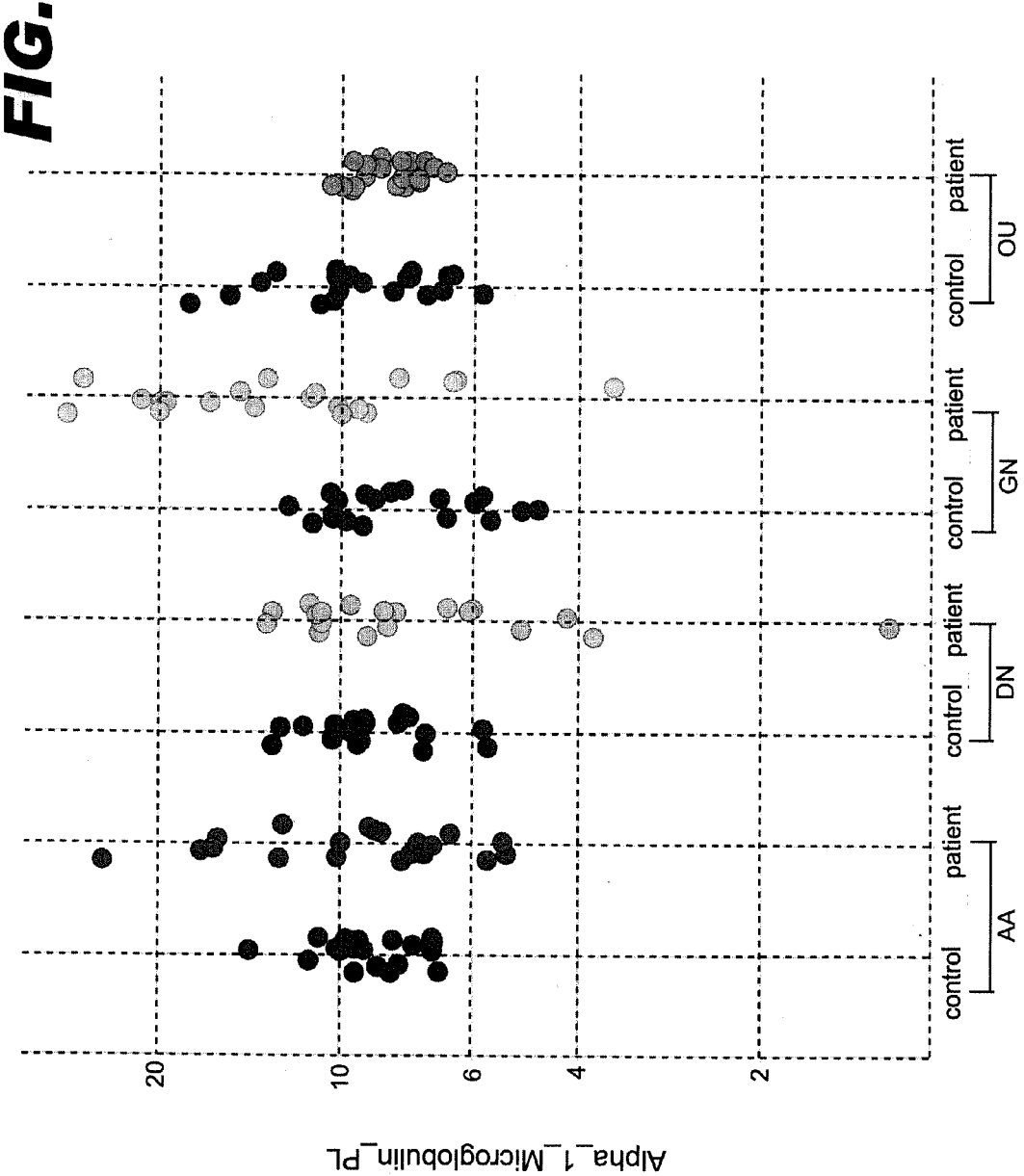
FIG. 2 is a number of scatter plots of results on selected proteins in urine and plasma. The various groups are indicated as follows—control: blue, AA: red, DN: green, GN: yellow, OU: orange. (A) A1M in plasma, (B) cystatin C in plasma, (C) B2M in urine, (D) cystatin C in urine.

P values <0.0001 are shown in bold italics
P values <0.005 are shown in bold
P values <0.05 are shown in italics For the various disease groups, univariate statistical analysis revealed that in a direct comparison (T-test) between cases and controls, a number of proteins were differentially expressed in both urine and plasma (Table 10 and FIG. 2). In particular, clusterin showed a marked differential pattern in plasma.

TABLE 10

Differentially regulated proteins by univariate statistical analysis

| Group | Matrix | Protein | p-value |
|---|---|---|---|
| AA | Urine | Calbindin | 0.016 |
| AA | Urine | NGAL | 0.04 |
| AA | Urine | Osteopontin | 0.005 |
| AA | Urine | Creatinine | 0.001 |
| AA | Plasma | Calbindin | 0.05 |
| AA | Plasma | Clusterin | 0.003 |
| AA | Plasma | KIM-1 | 0.03 |
| AA | Plasma | THP | 0.001 |
| AA | Plasma | TIMP-1 | 0.02 |
| DN | Urine | Creatinine | 0.04 |
| DN | Plasma | Clusterin | 0.006 |
| DN | Plasma | KIM-1 | 0.01 |
| GN | Urine | Creatinine | 0.004 |
| GN | Urine | Microalbumin | 0.0003 |
| GN | Urine | NGAL | 0.05 |
| GN | Urine | Osteopontin | 0.05 |
| GN | Urine | TFF3 | 0.03 |
| GN | Plasma | Alpha 1 Microglobulin | 0.002 |
| GN | Plasma | Beta 2 Microglobulin | 0.03 |
| GN | Plasma | Clusterin | 0.00 |
| GN | Plasma | Cystatin C | 0.01 |
| GN | Plasma | KIM-1 | 0.003 |
| GN | Plasma | NGAL | 0.03 |
| GN | Plasma | THP | 0.001 |
| GN | Plasma | TIMP-1 | 0.003 |
| GN | Plasma | TFF3 | 0.01 |
| GN | Plasma | VEGF | 0.02 |
| OU | Urine | Clusterin | 0.02 |
| OU | Urine | Microalbumin | 0.007 |
| OU | Plasma | Clusterin | 0.00 |

Figure 3:
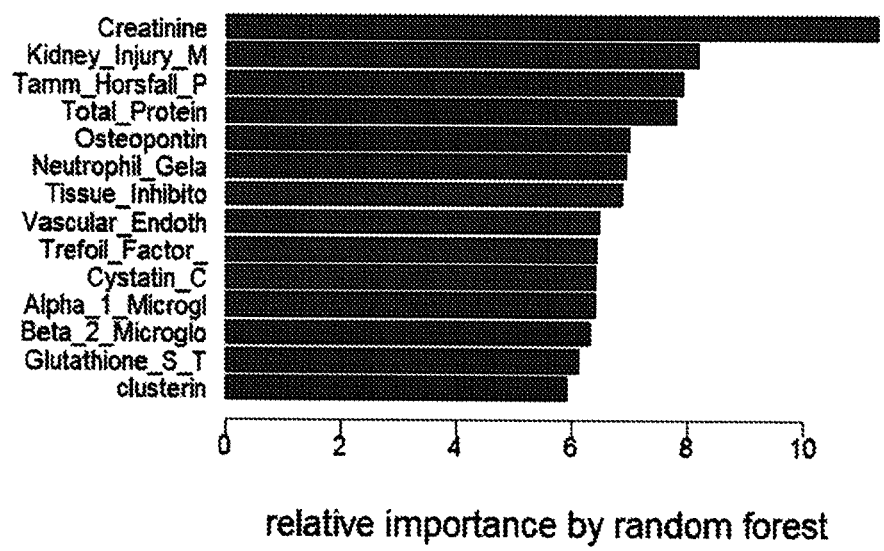
FIG. 3 depicts the multivariate analysis of the disease groups and their respective matched controls using plasma results. Relative importance shown using the random forest model.

Application of multivariate analysis yielded statistical models that predicted disease from control samples (plasma results are shown in FIG. 3)

In conclusion, these results form a valuable base for further studies on these biomarkers in urine and plasma both regarding baseline levels in normal populations and regarding the differential expression of the analytes in various disease groups. Using this panel of analytes, error rates from adaboosting and/or random forest were low enough (<10%) to allow a prediction model to differentiate between control and disease patient samples. Several of the analytes showed a greater correlation to eGFR in plasma than in urine.

Example 9

Statistical Analysis of Kidney Biomarkers in Plasma and Urine from Patients with Renal Injury Urine and plasma samples were taken from 80 normal control group subjects and 20 subjects from each of four disorders: analgesic abuse, diabetic nephropathy, glomerulonephritis, and obstructive uropathy. The samples were analyzed for the quantity and presence of 16 different proteins (alpha-1 microglobulin ($\alpha$1M), beta-2 microglobulin ($\beta$2M), calbindin, clusterin, CTGF, creatinine, cystatin C, GST-alpha, KIM-1, microalbumin, NGAL, osteopontin, THP, TIMP-1, TFF-3, and VEGF) as described in Example 1 above. The goal was to determine the analytes that distinguish between a normal sample and a diseased sample, a normal sample and an obstructive uropathy (OU) sample, and finally, an obstructive uropathy sample from the other disease samples (diabetic nephropathy (DN), analgesic abuse (AA), and glomerulonephritis (GN)).

From the above protein analysis data, bootstrap analysis was used to estimate the future performance of several classification algorithms. For each bootstrap run, training data and testing data was randomly generated. Then, the following algorithms were applied on the training data to generate models and then apply the models to the testing data to make predictions: automated Matthew's classification algorithm, classification and regression tree (CART), conditional inference tree, bagging, random forest, boosting, logistic regression, SVM, and Lasso. The accuracy rate and ROC areas were recorded for each method on the prediction of the testing data. The above was repeated 100 times. The mean and the standard deviation of the accuracy rates and of the ROC areas were calculated.

Figure 4A:
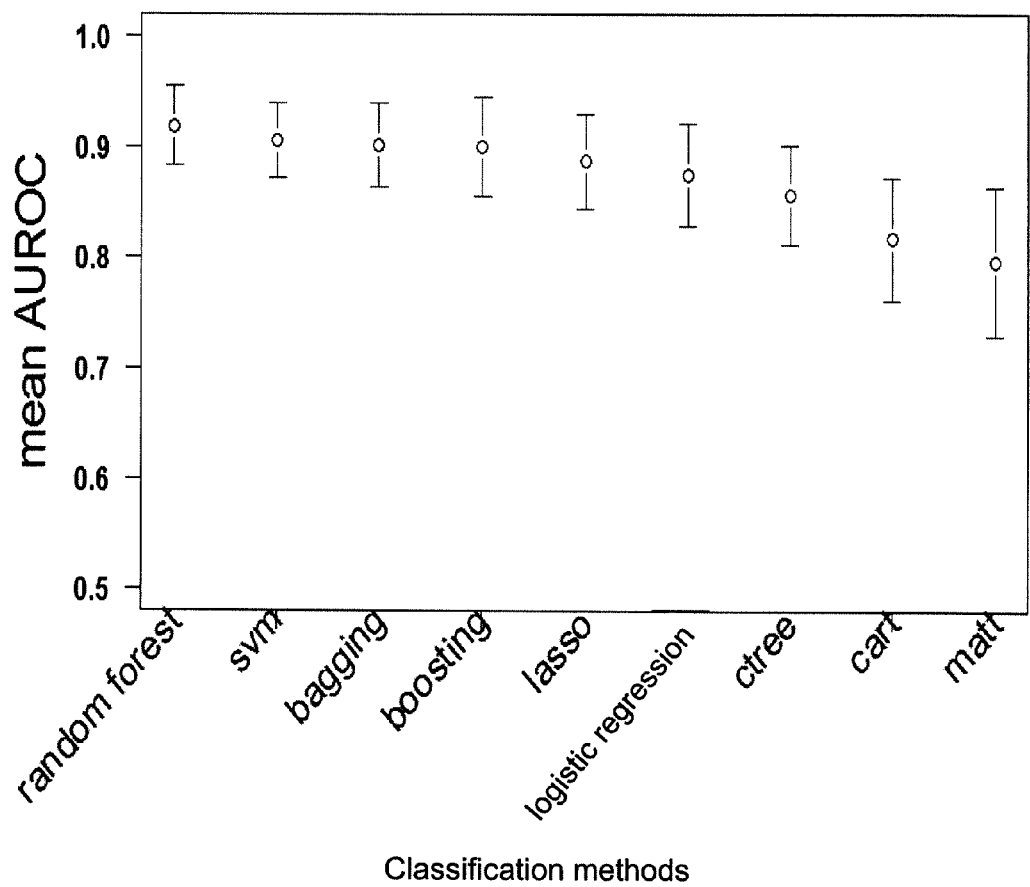
FIG. 4 depicts three graphs showing the mean AUROC and its standard deviation (A) for plasma samples, and mean error rates (B) and mean AUROC (C) from urine samples for each classification method used to distinguish disease samples vs. normal samples. Disease encompasses analgesic abuse (AA), glomerulonephritis (GN), obstructive uropathy (OU), and diabetic nephropathy (DN). Normal=NL.
Figure 4B:
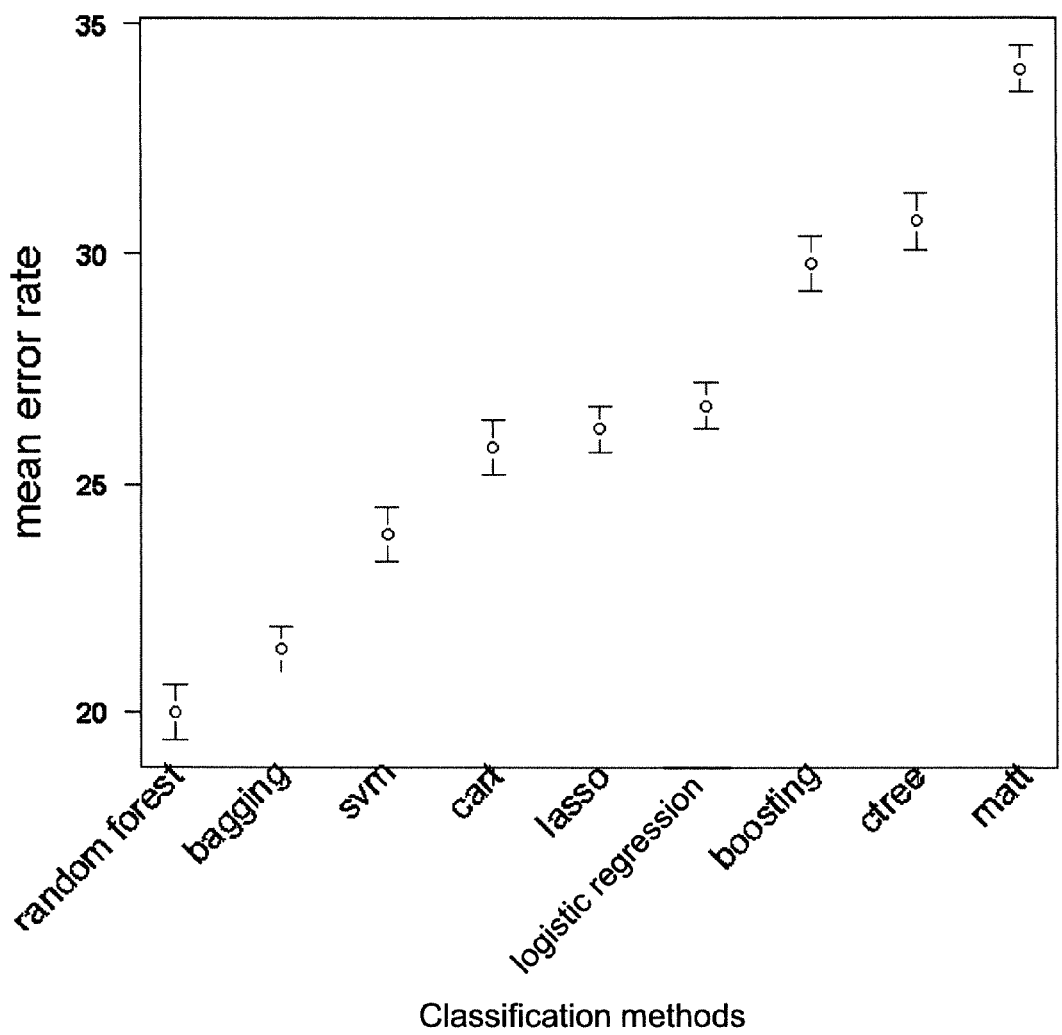
Figure 4C:
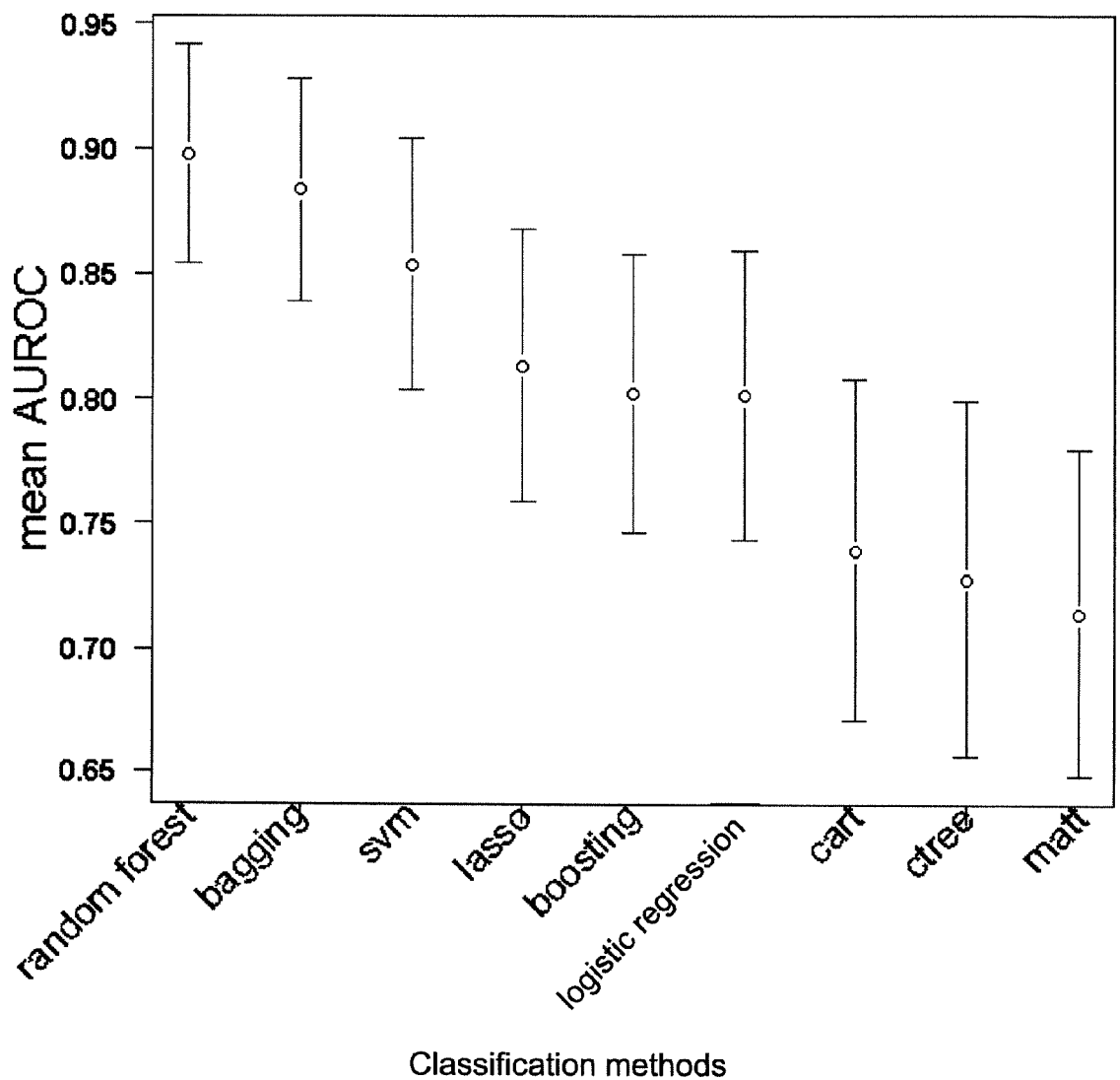
Figure 6A:
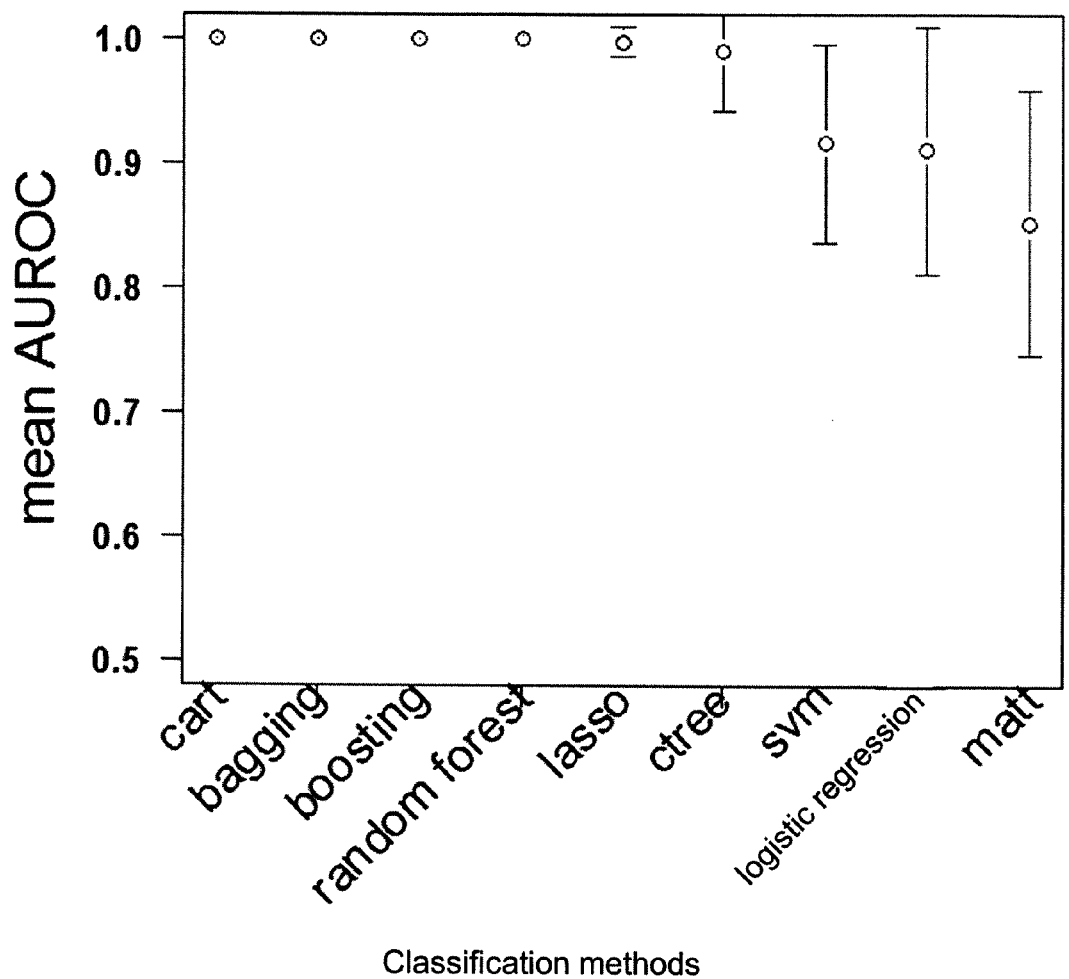
FIG. 6 depicts three graphs showing the mean AUROC and its standard deviation (A) for plasma samples, and mean error rates (B) and mean AUROC (C) from urine samples for each classification method used to distinguish obstructive uropathy samples vs. normal samples. Abbreviations as in FIG. 4.
Figure 6B:
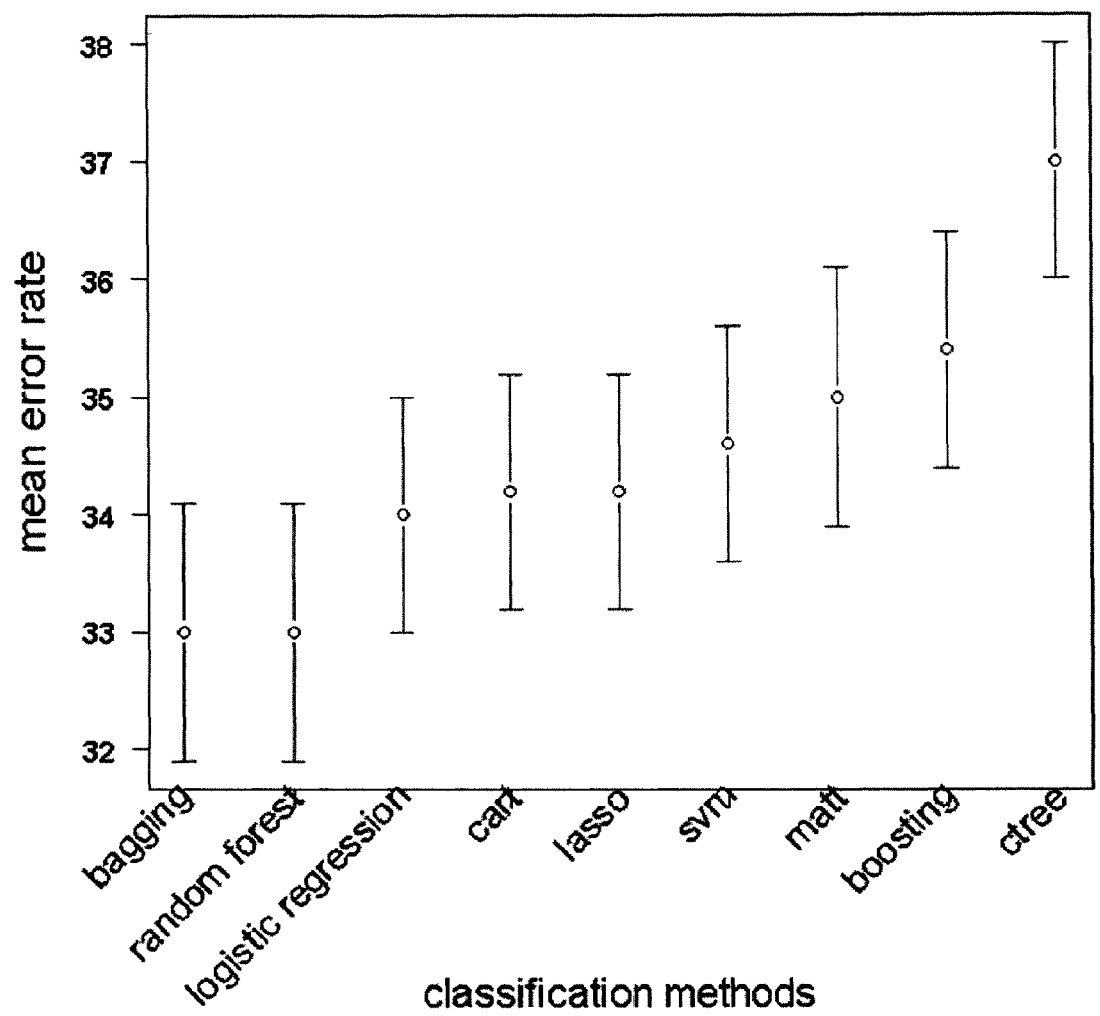
Figure 6C:
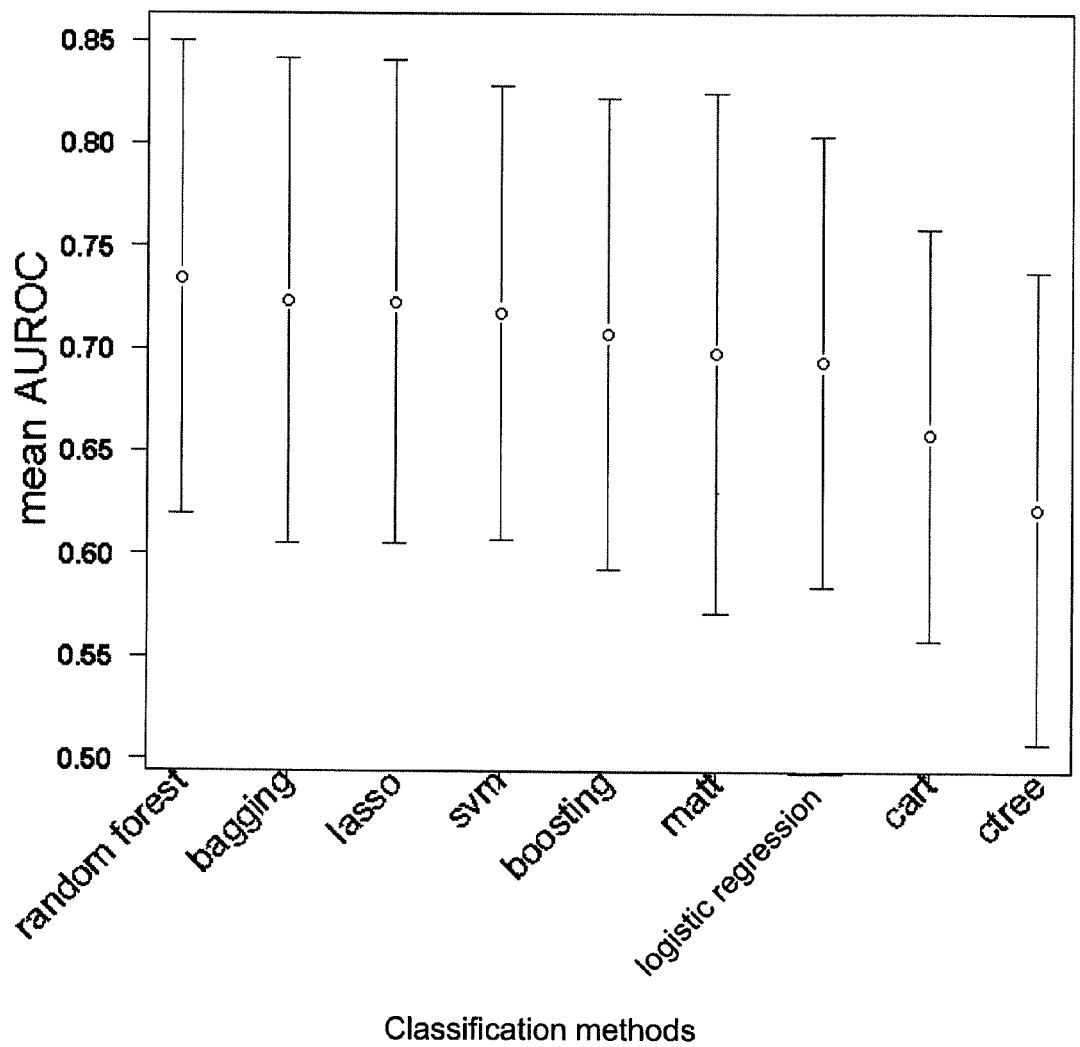
Figure 8A:
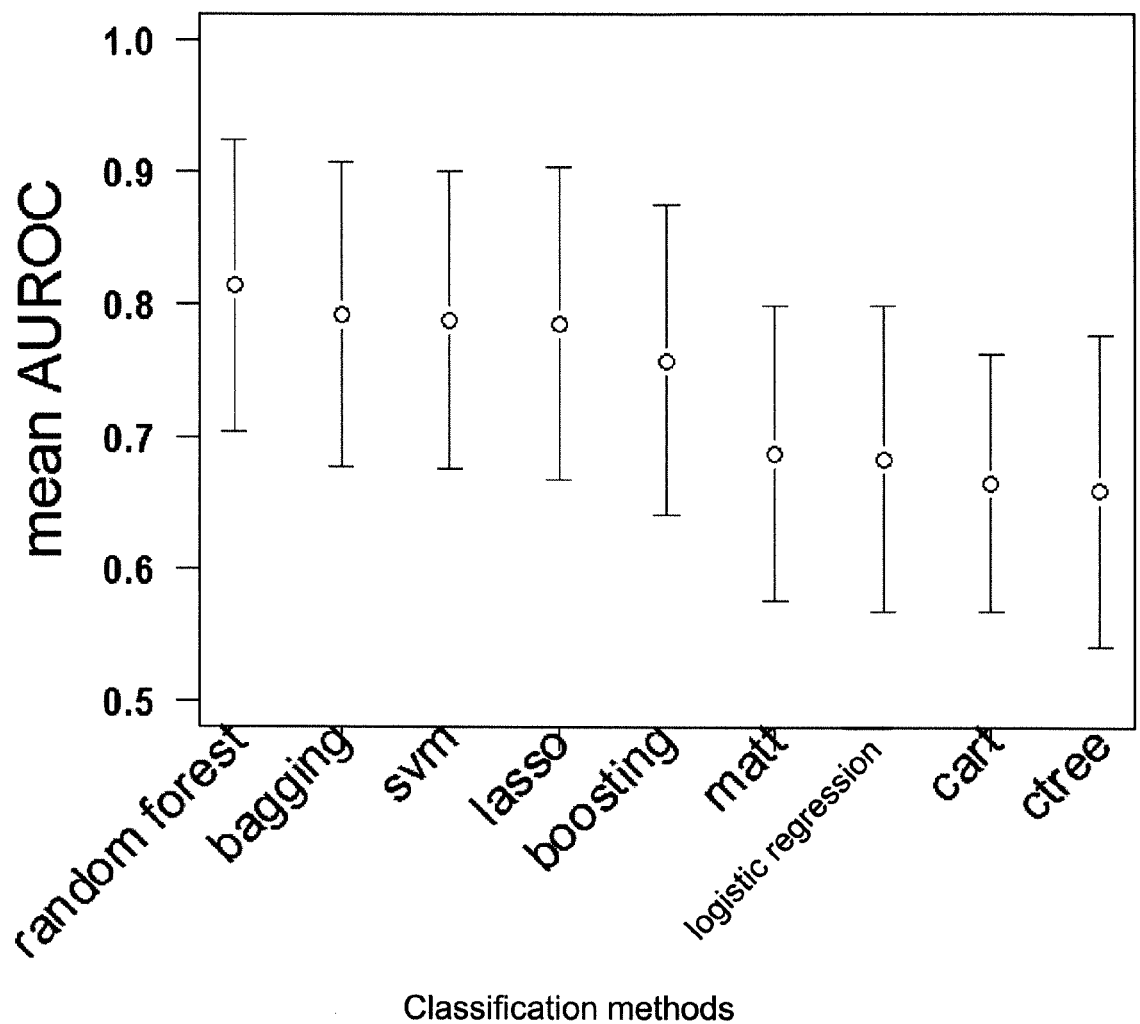
FIG. 8 depicts three graphs showing the mean AUROC and its standard deviation (A) for plasma samples, and mean error rates (B) and mean AUROC (C) from urine samples for each classification method used to distinguish analgesic abuse samples vs. obstructive uropathy samples. Abbreviations as in FIG. 4.
Figure 8B:
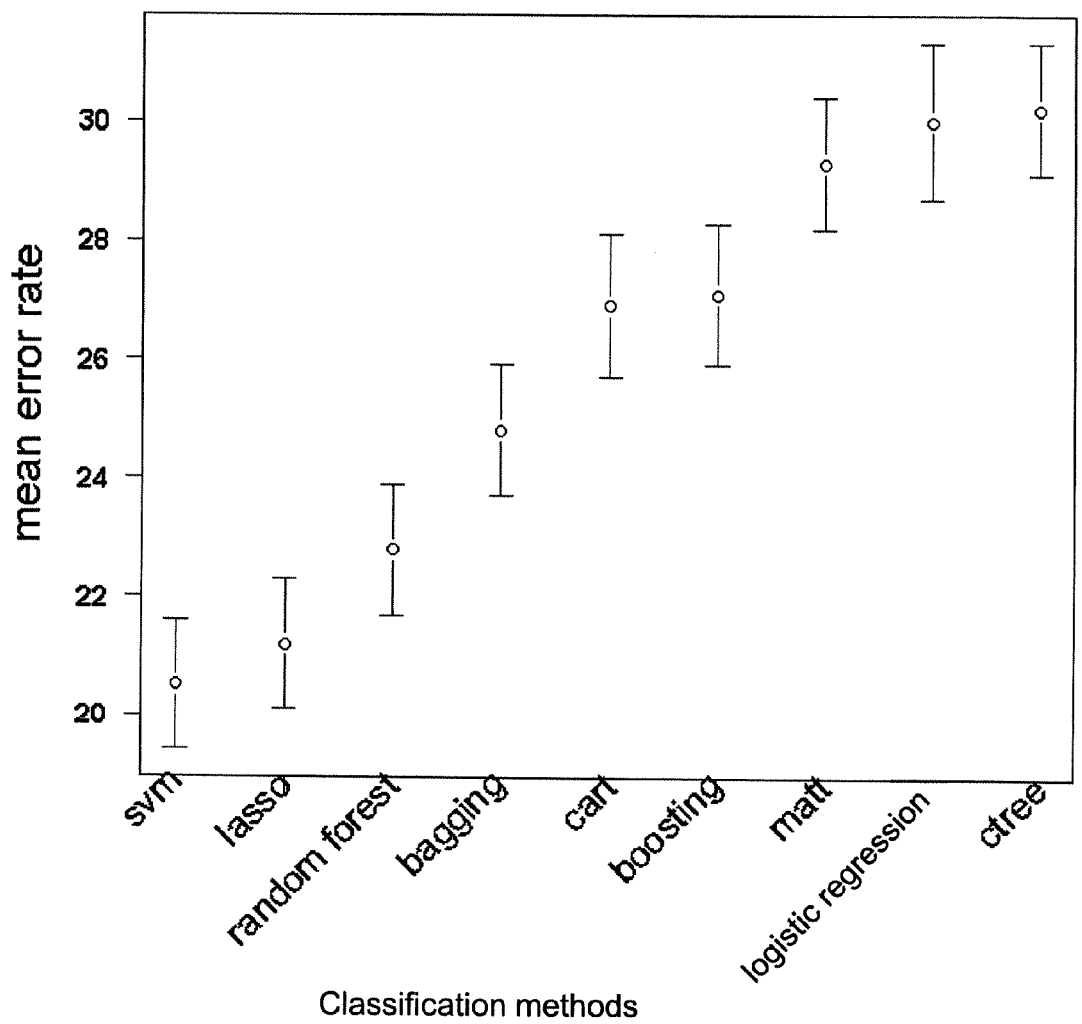
Figure 8C:
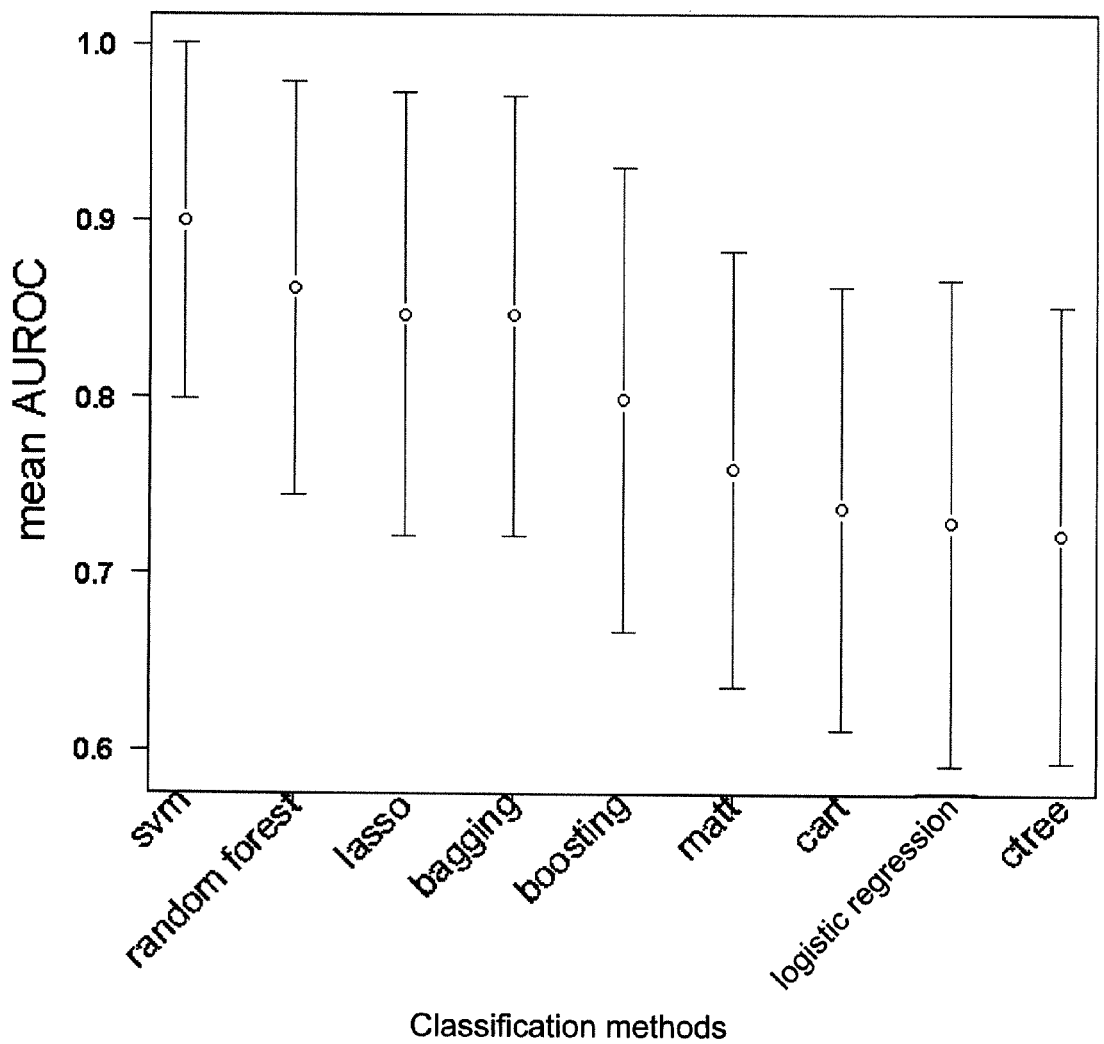
Figure 10A:
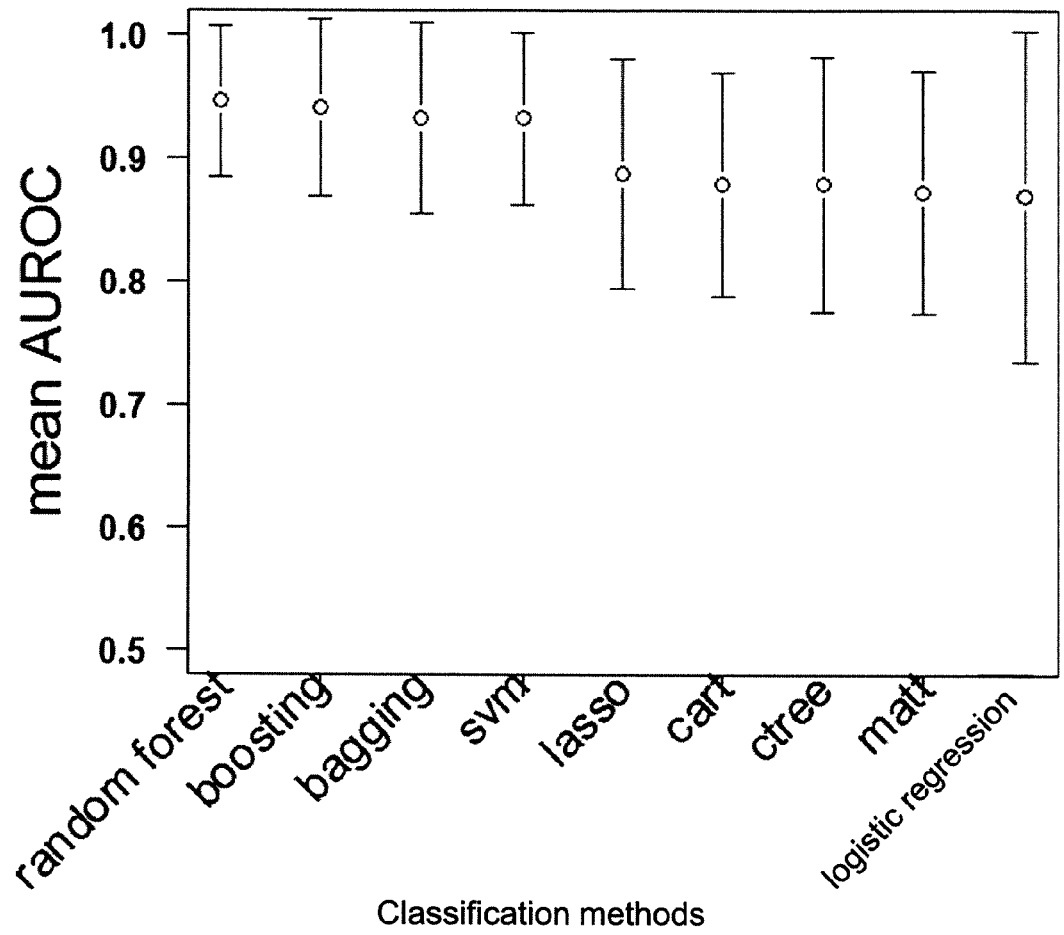
FIG. 10 depicts three graphs showing the mean AUROC and its standard deviation (A) for plasma samples, and mean error rates (B) and mean AUROC (C) from urine samples for each classification method used to distinguish obstructive uropathy samples vs. glomerulonephritis samples. Abbreviations as in FIG. 4.
Figure 10B:
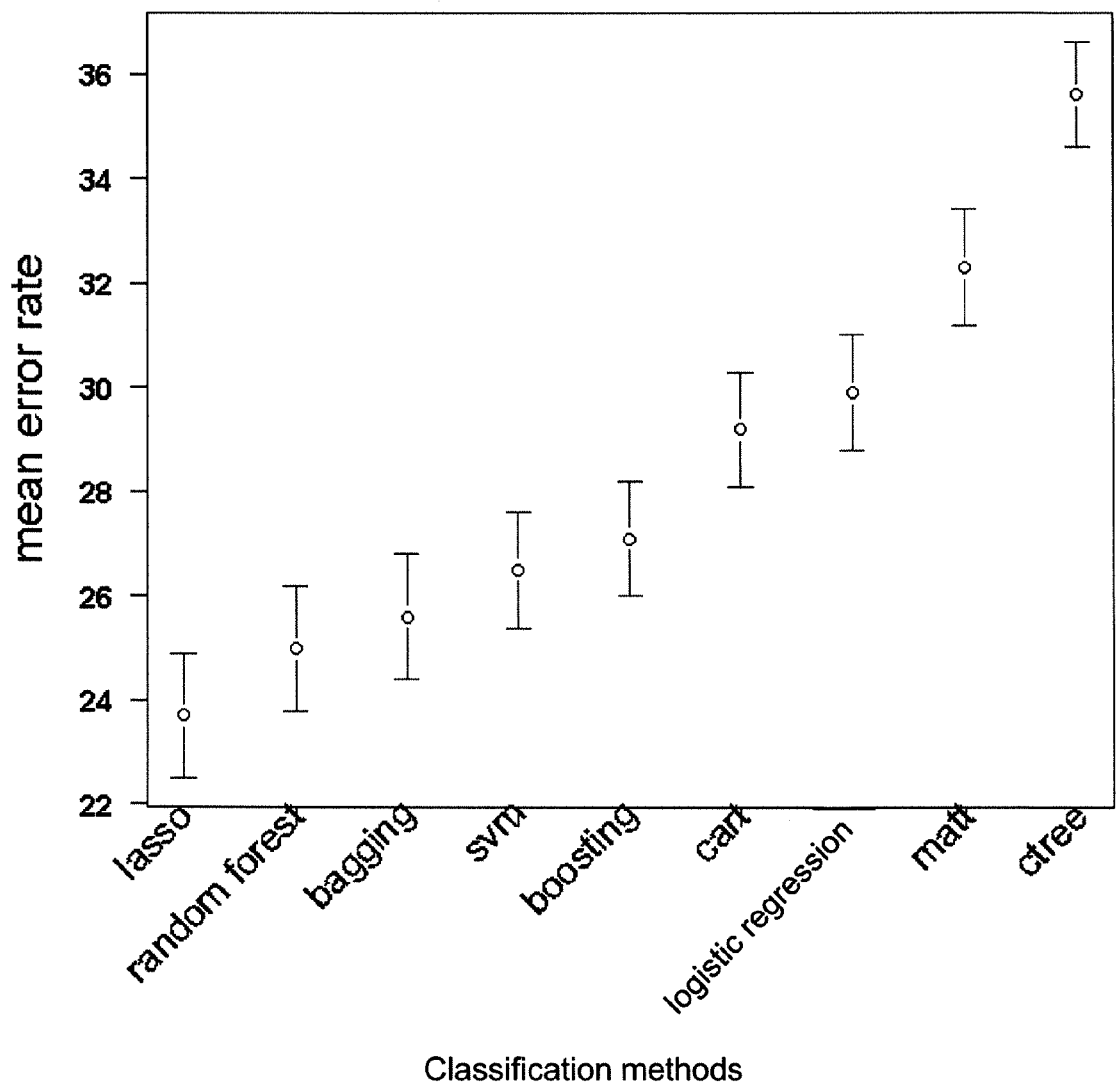
Figure 10C:
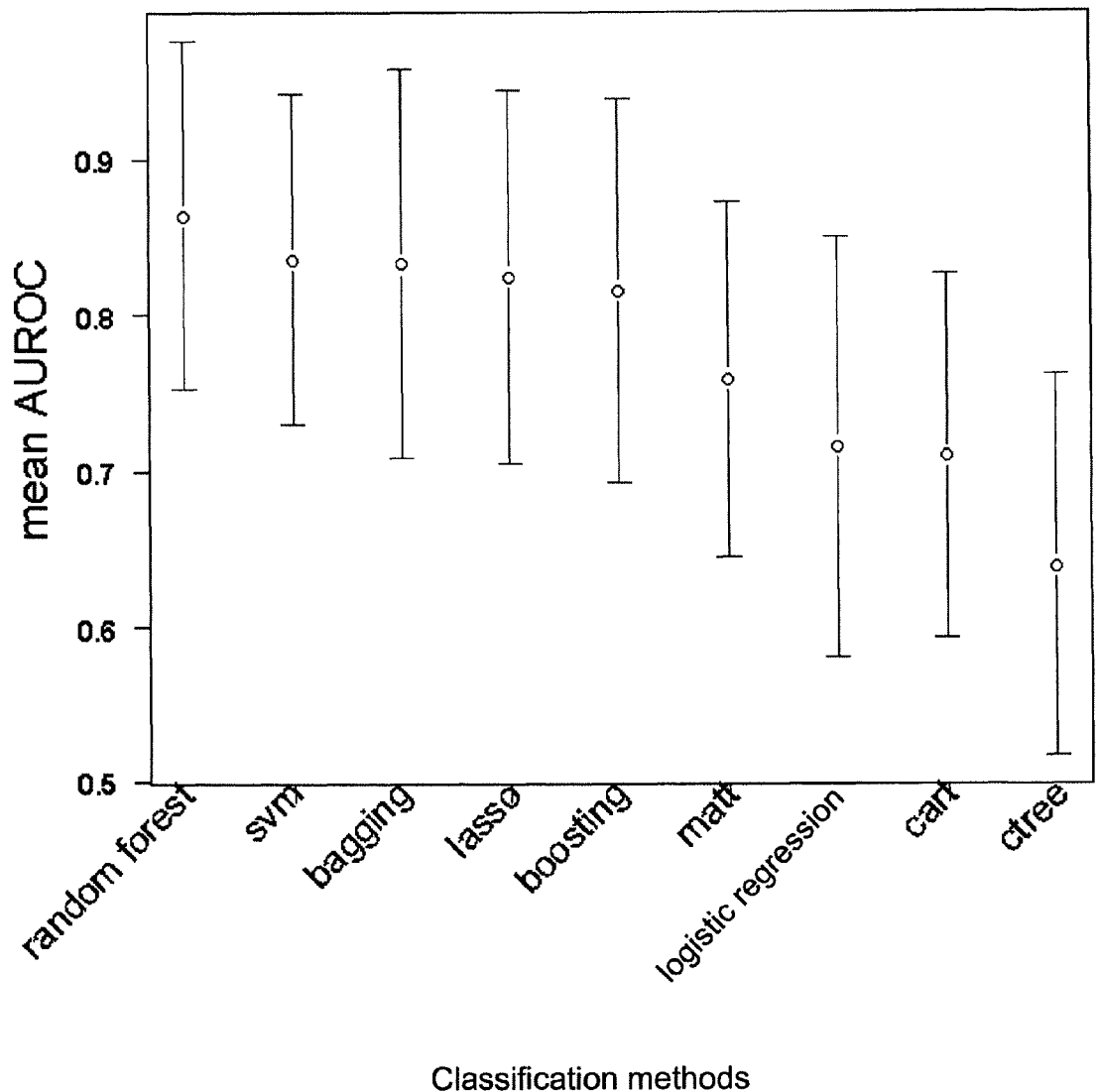
Figure 12A:
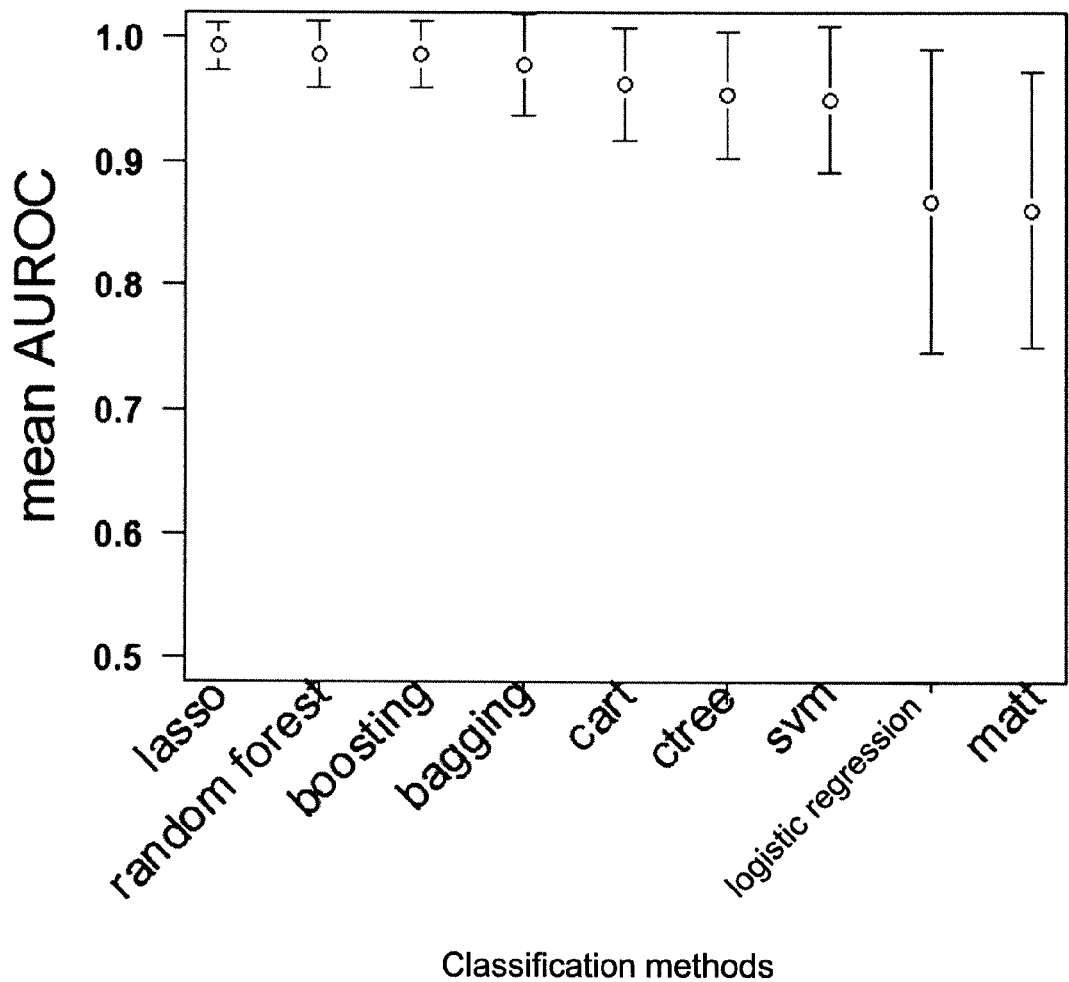
FIG. 12 depicts three graphs showing the mean AUROC and its standard deviation (A) for plasma samples, and mean error rates (B) and mean AUROC (C) from urine samples for each classification method used to distinguish diabetic nephropathy samples vs. obstructive uropathy samples. Abbreviations as in FIG. 4.
Figure 12B:
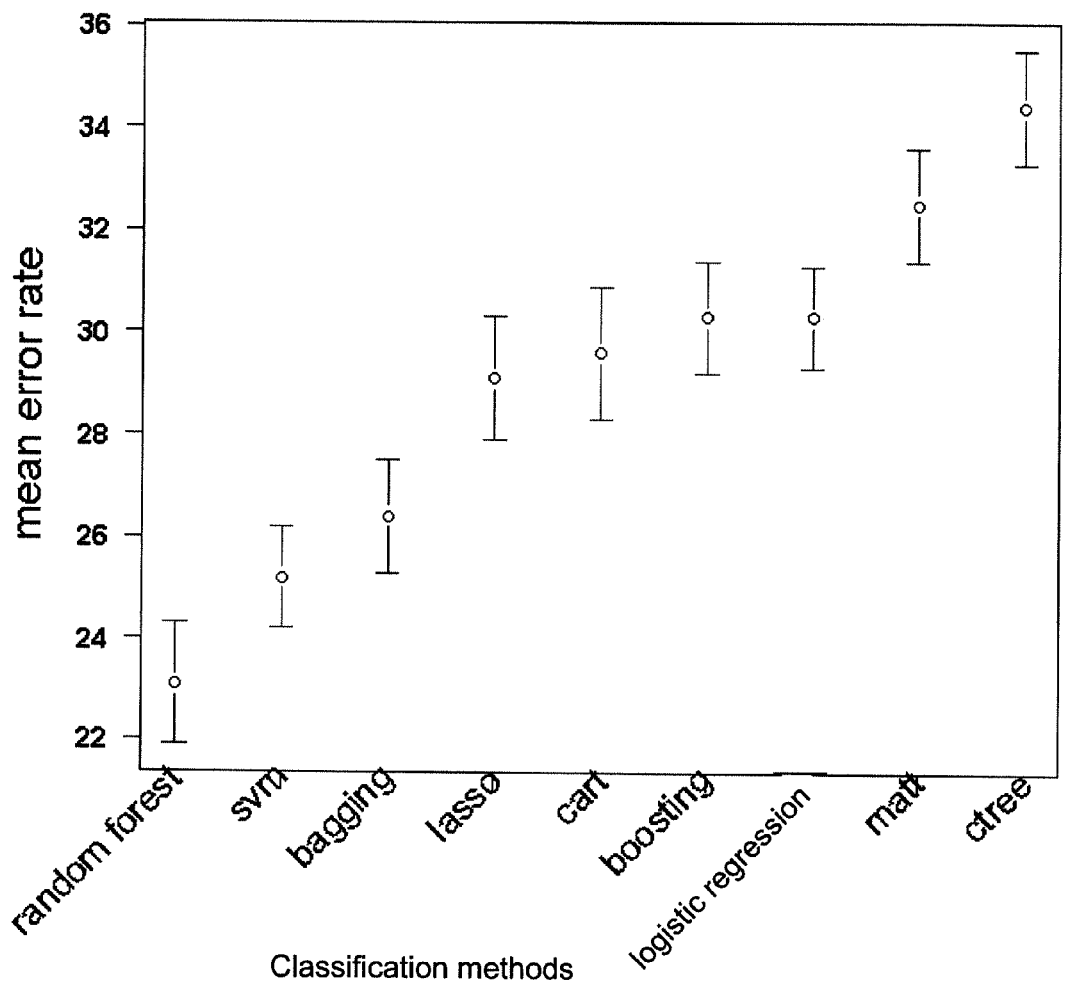
Figure 12C:
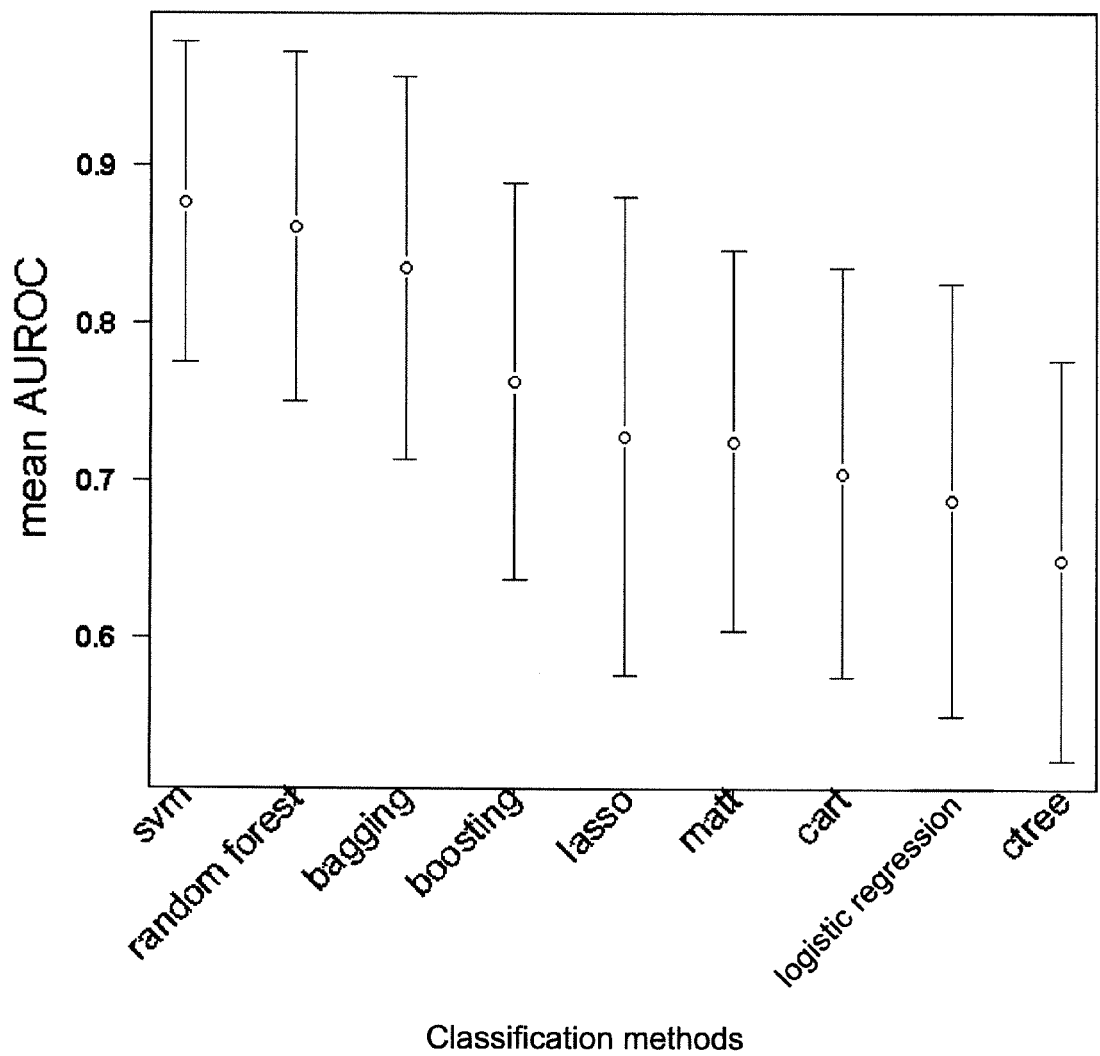

The mean error rates and AUROC were calculated from urine and AUROC was calculated from plasma for 100 runs of the above method for each of the following comparisons: disease (AA+GN+OU+DN) vs. normal (FIG. 4, Table 11), OU vs. normal (FIG. 6, Table 13), OU vs. AA (FIG. 8, Table 15), OU vs. GN (FIG. 10, Table 17), and OU vs. DN (FIG. 12, Table 19).

Figure 5A:
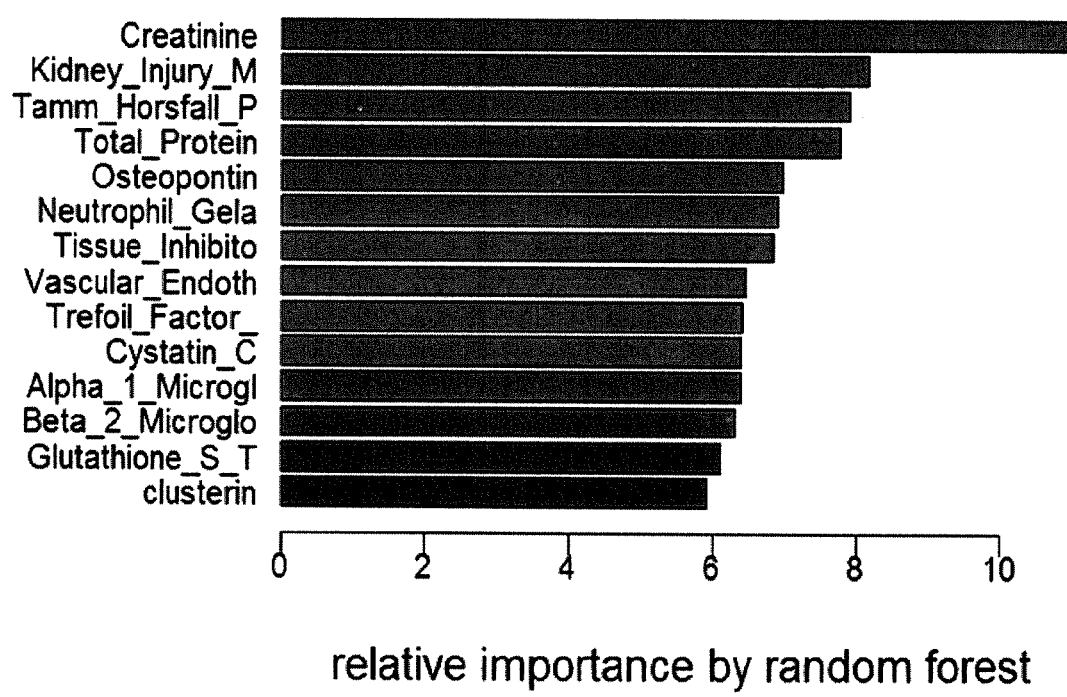
FIG. 5 depicts three graphs showing the average importance of analytes and clinical variables from 100 bootstrap runs measured by random forest (A and B) or boosting (C) to distinguish disease (AA+GN+ON+DN) samples vs. normal samples from plasma (A) and urine (B and C).
Figure 5B:
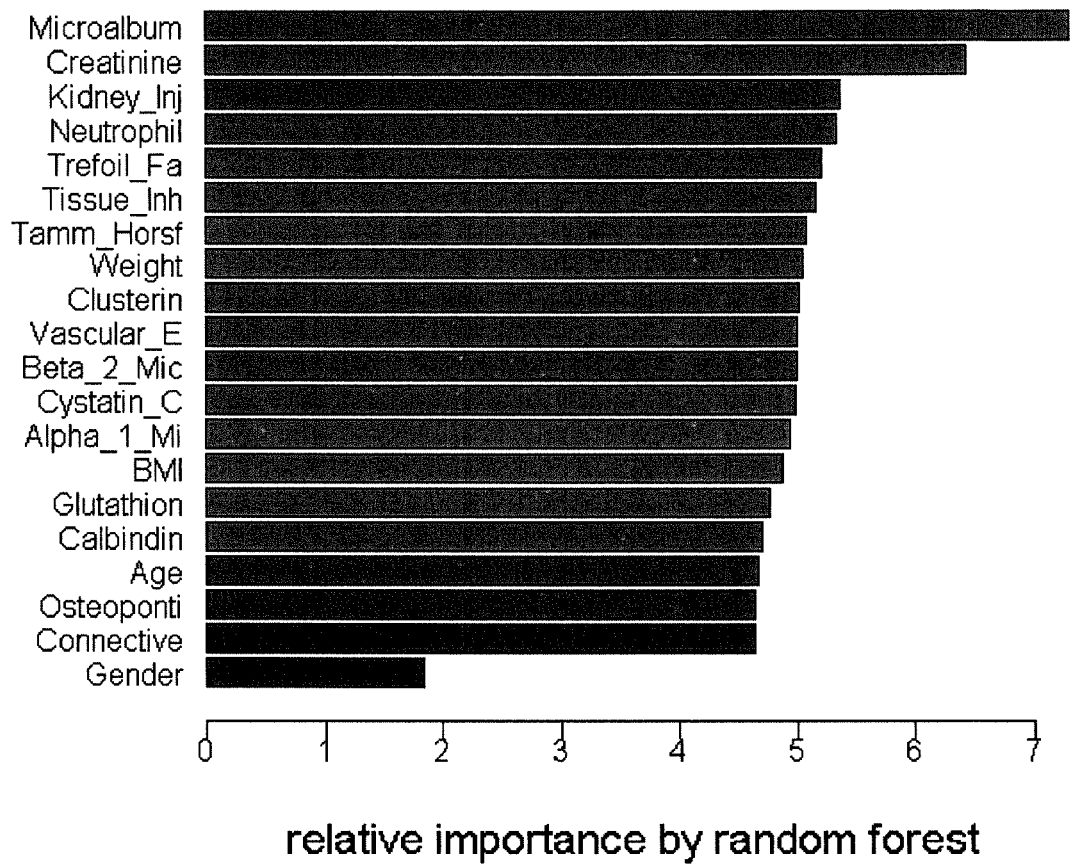
Figure 5C:
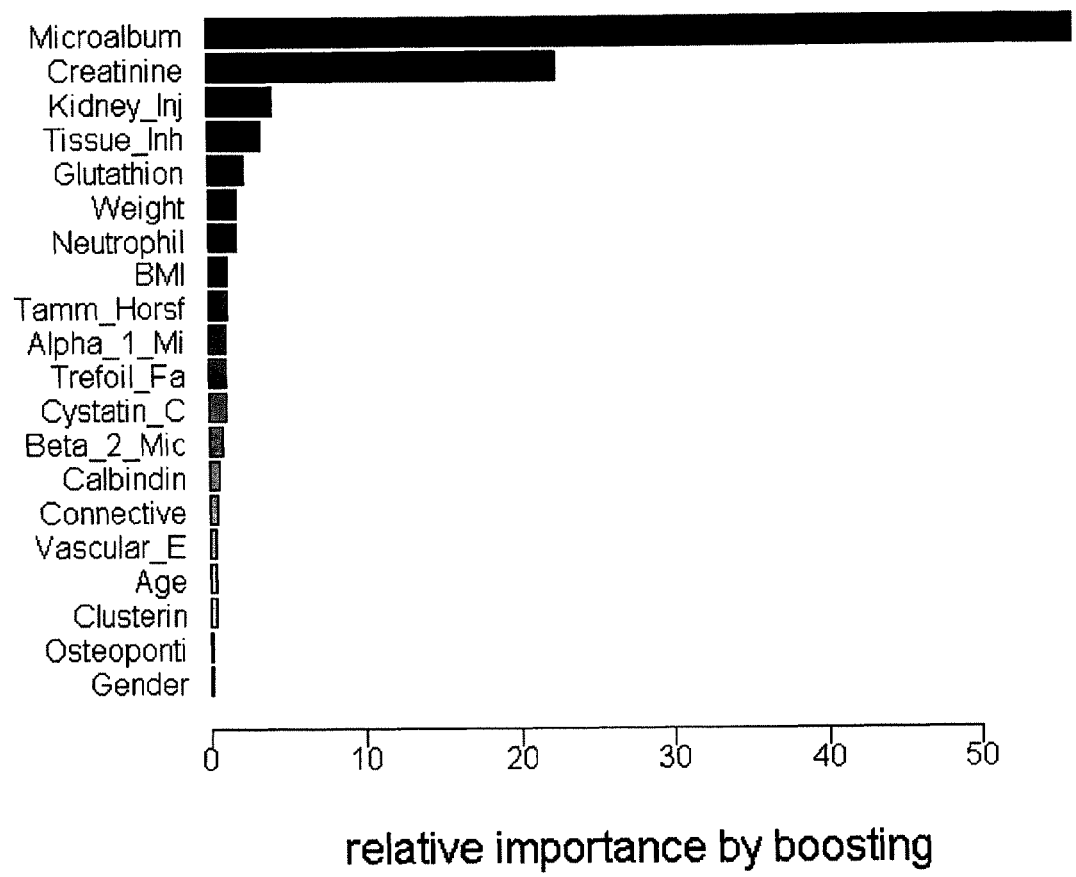
Figure 7A:
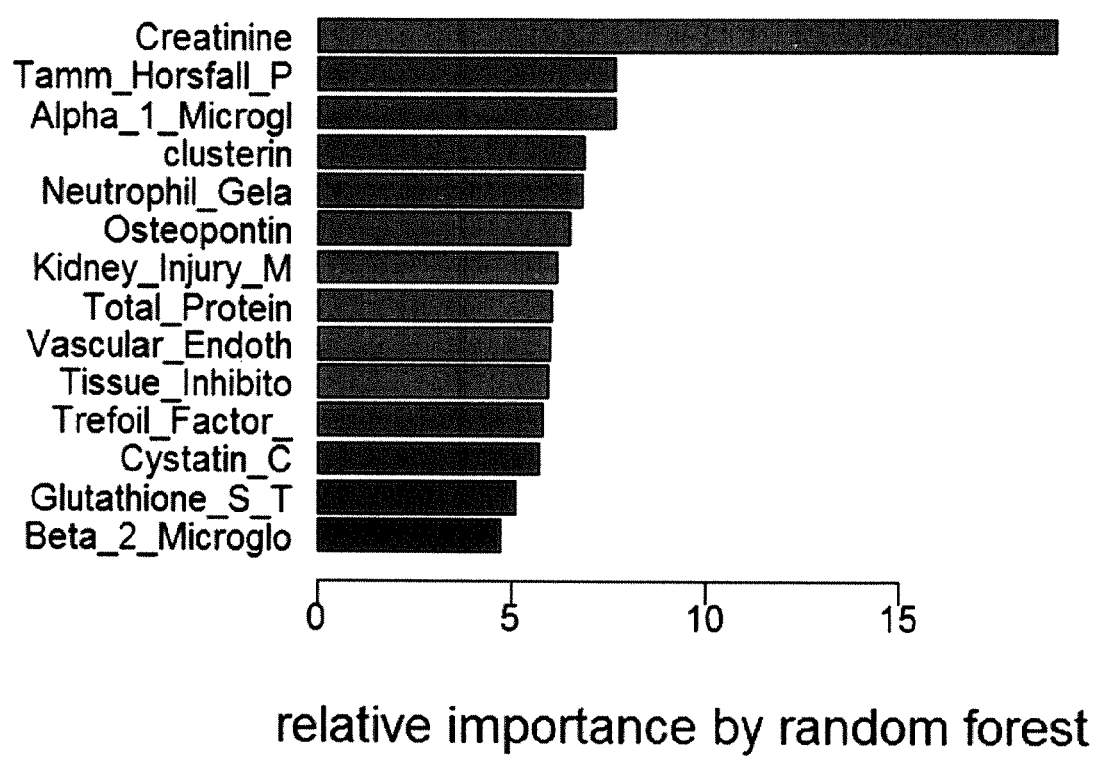
FIG. 7 depicts three graphs showing the average importance of analytes and clinical variables from 100 bootstrap runs measured by random forest (A and B) or boosting (C) to distinguish obstructive uropathy samples vs. normal samples from plasma (A) and urine (B and C).
Figure 7B:
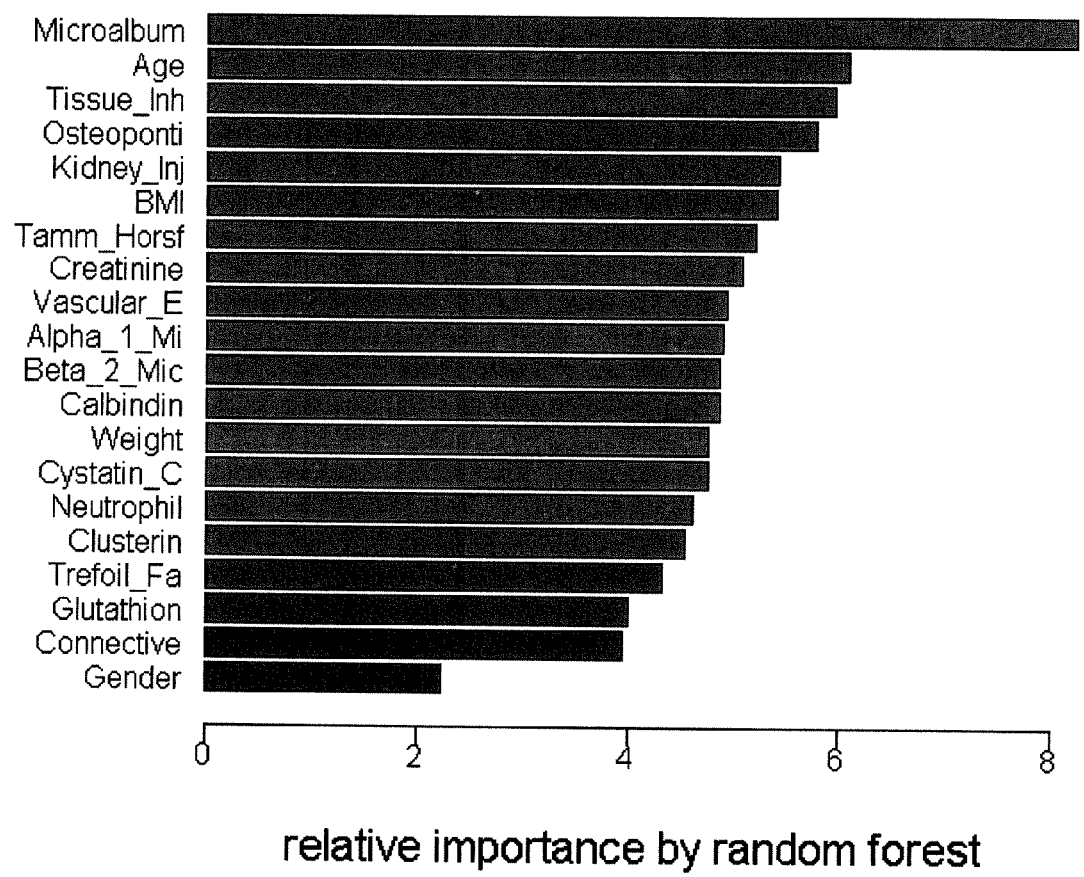
Figure 7C:
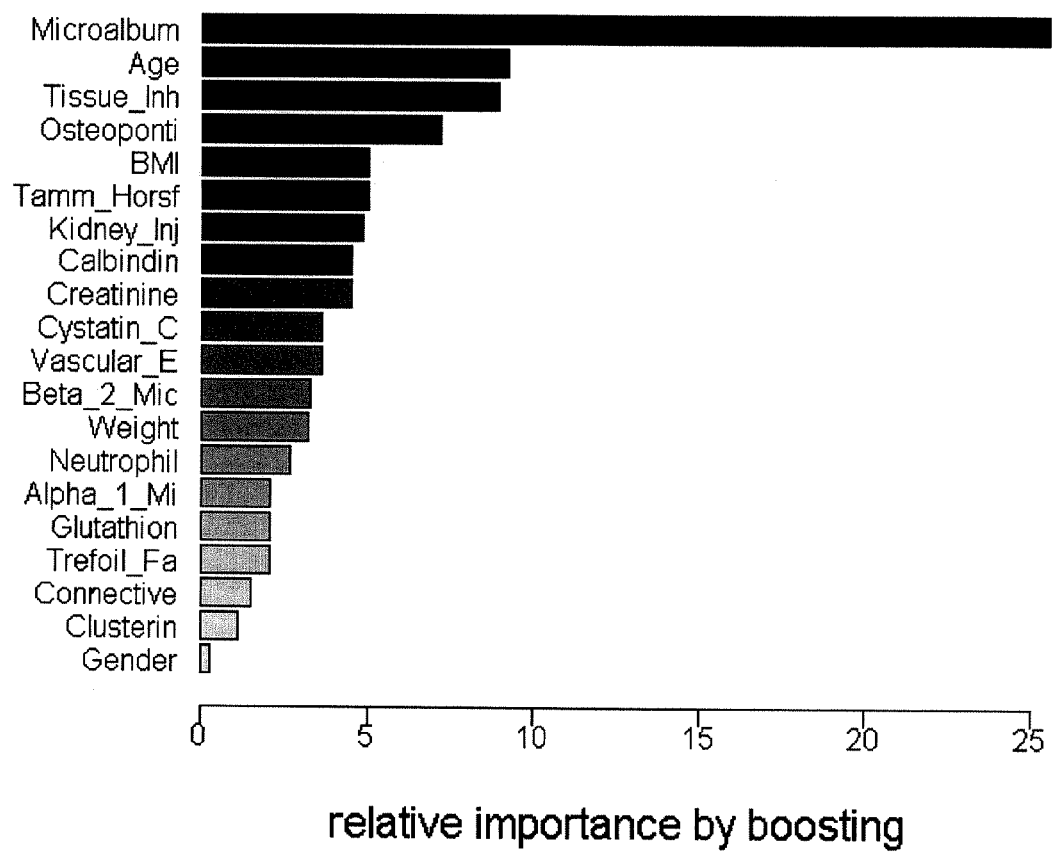
Figure 9A:
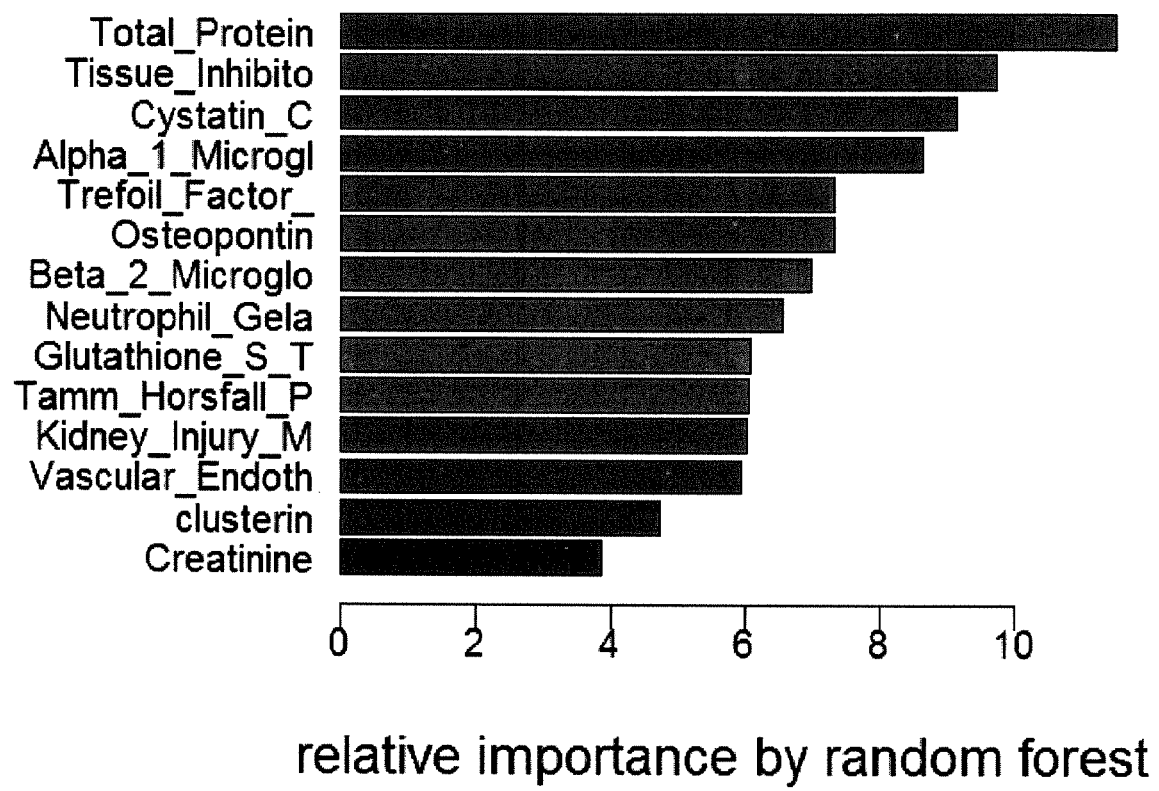
FIG. 9 depicts three graphs showing the average importance of analytes and clinical variables from 100 bootstrap runs measured by random forest (A and B) or boosting (C) to distinguish analgesic abuse samples vs. obstructive uropathy samples from plasma (A) and urine (B and C).
Figure 9B:
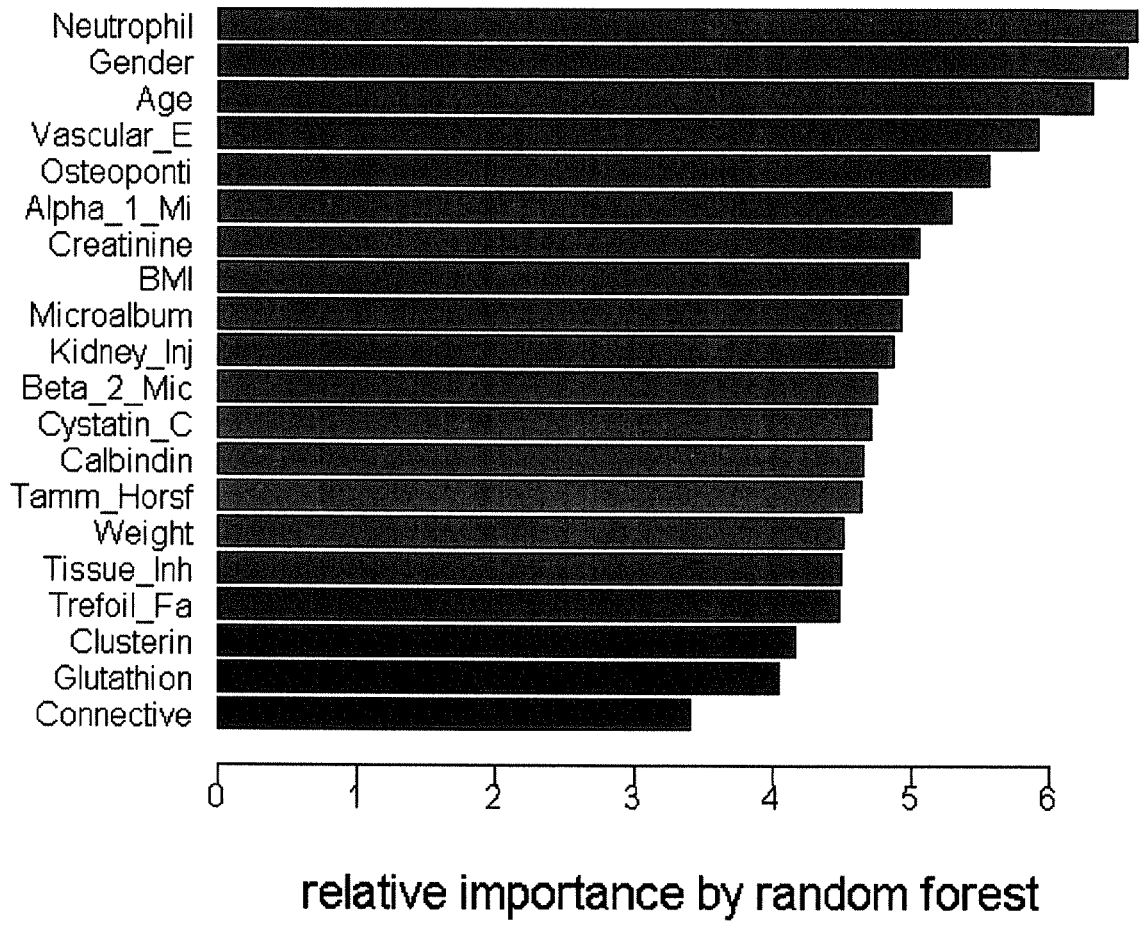
Figure 9C:
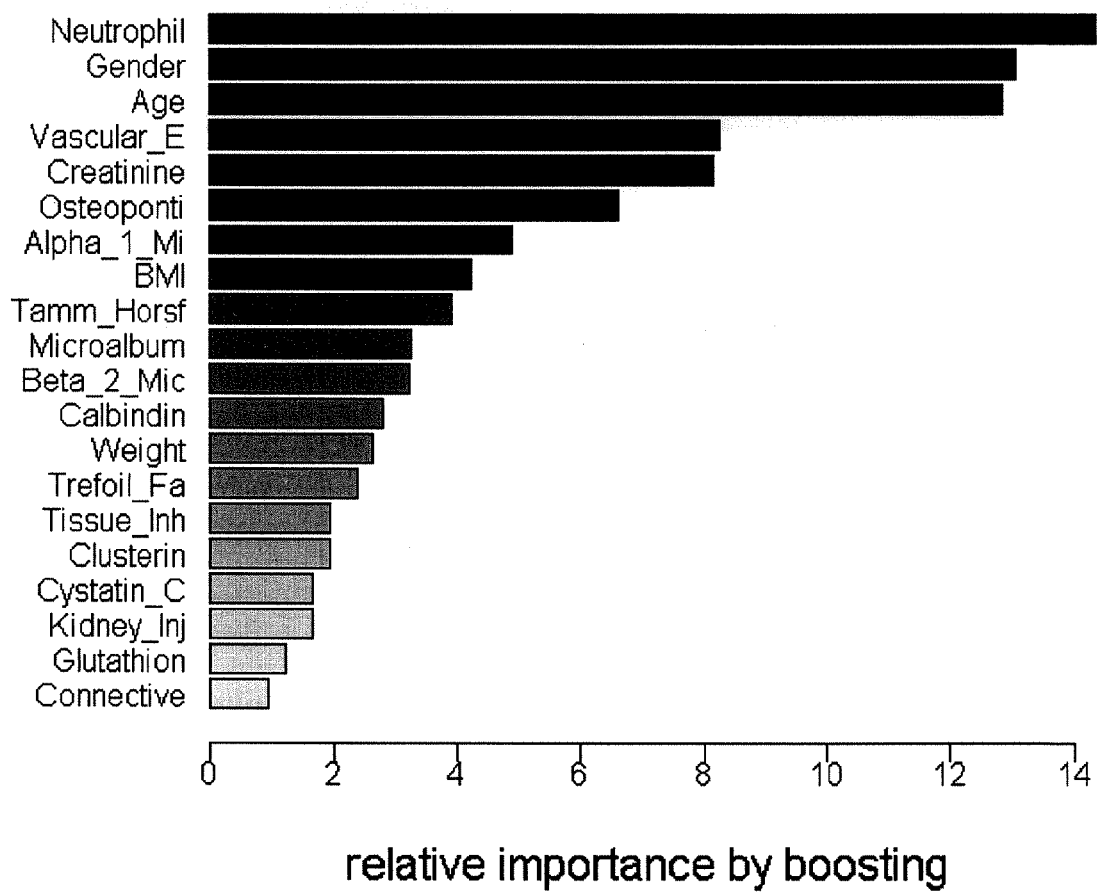
Figure 11A:
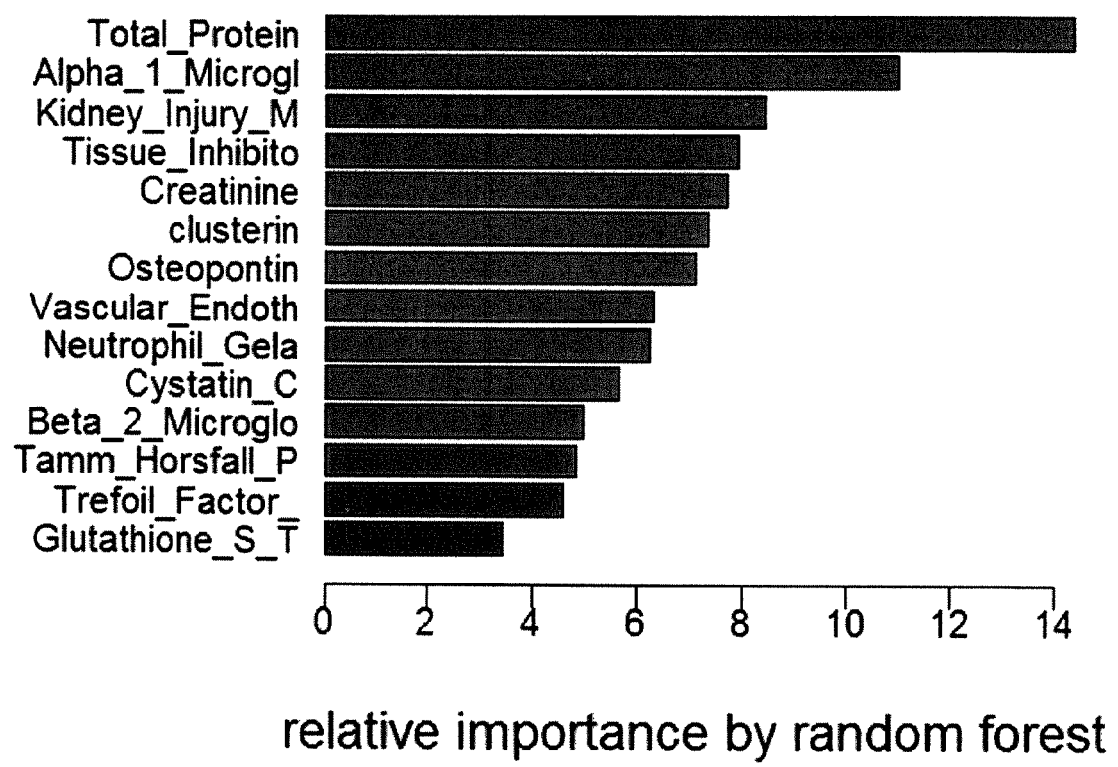
FIG. 11 depicts three graphs showing the average importance of analytes and clinical variables from 100 bootstrap runs measured by random forest (A and B) or boosting (C) to distinguish obstructive uropathy samples vs. glomerulonephritis samples from plasma (A) and urine (B and C).
Figure 11B:
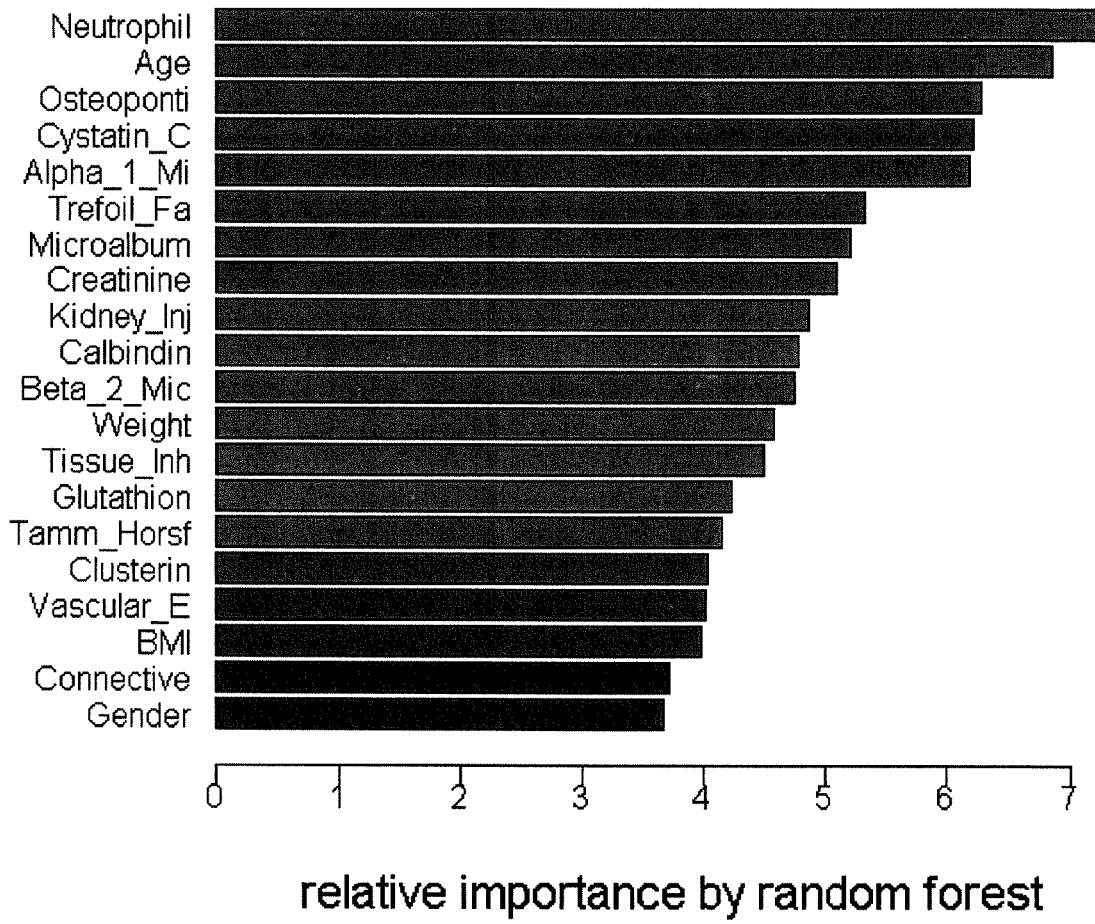
Figure 11C:
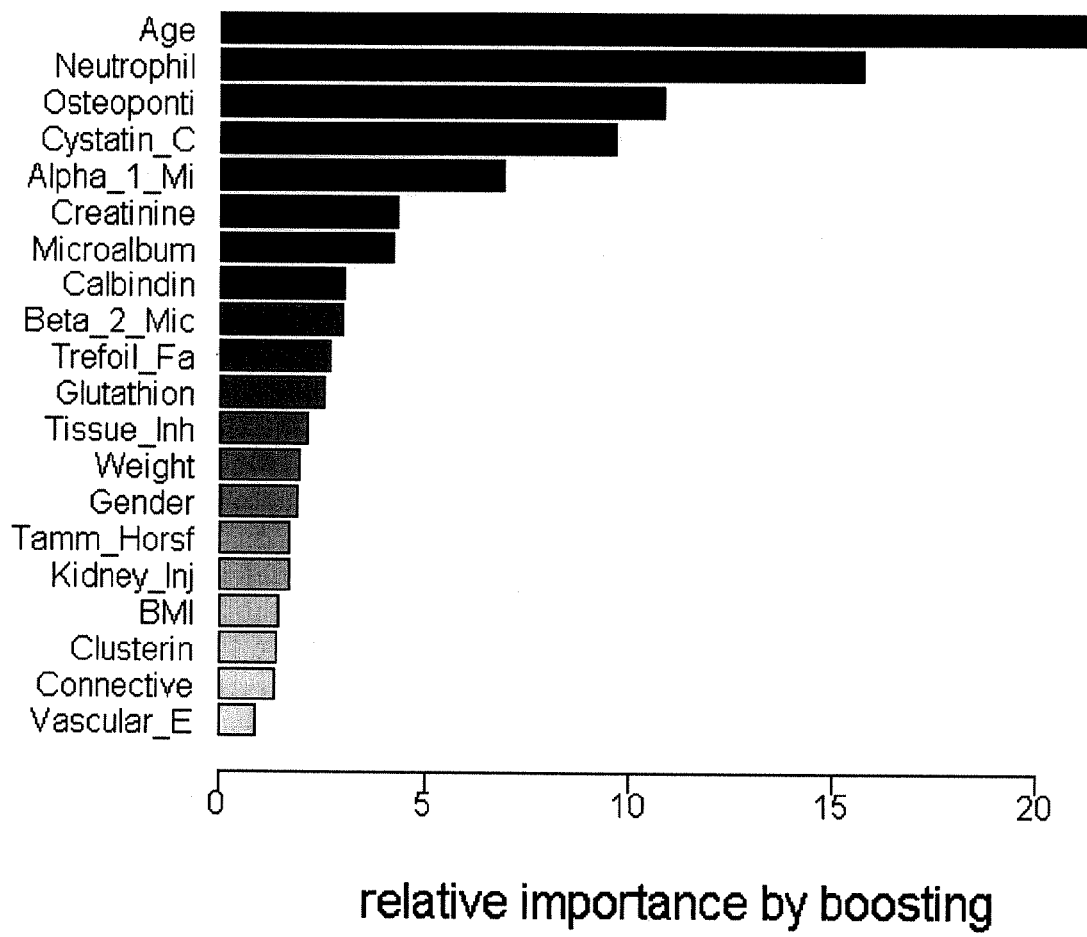
Figure 13A:
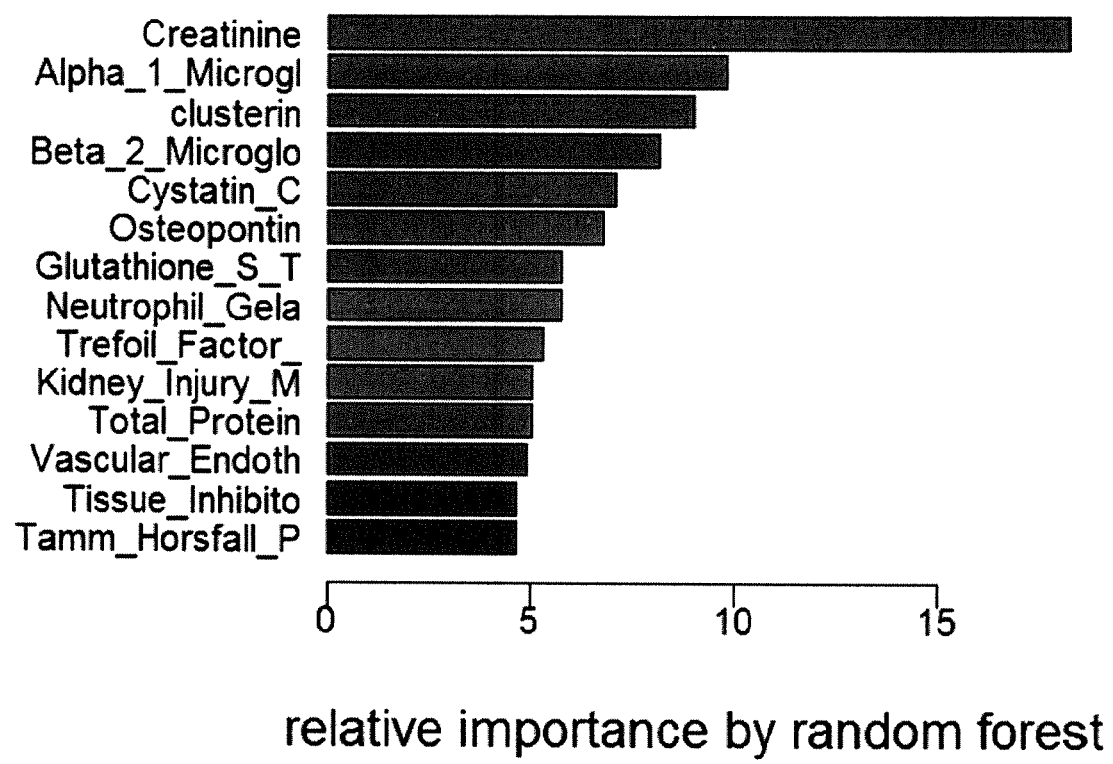
FIG. 13 depicts three graphs showing the average importance of analytes and clinical variables from 100 bootstrap runs measured by random forest (A and B) or boosting (C) to distinguish diabetic nephropathy samples vs. obstructive uropathy samples from plasma (A) and urine (B and C).
Figure 13B:
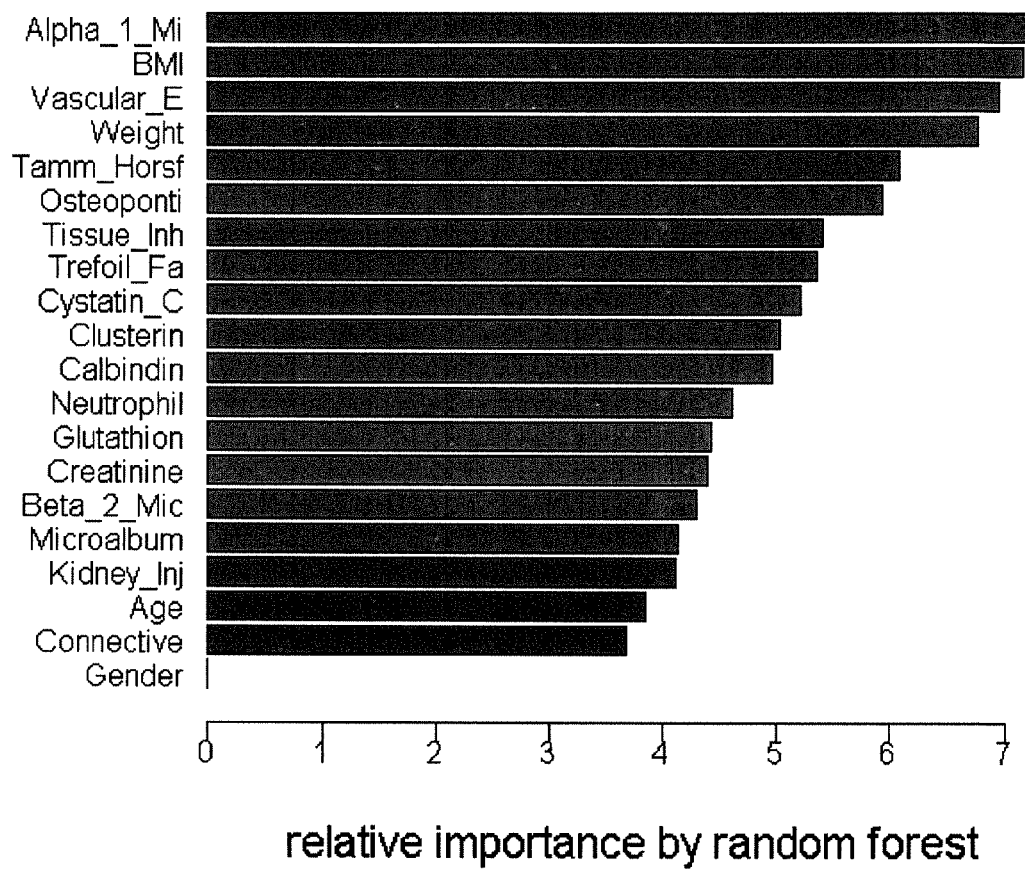
Figure 13C:
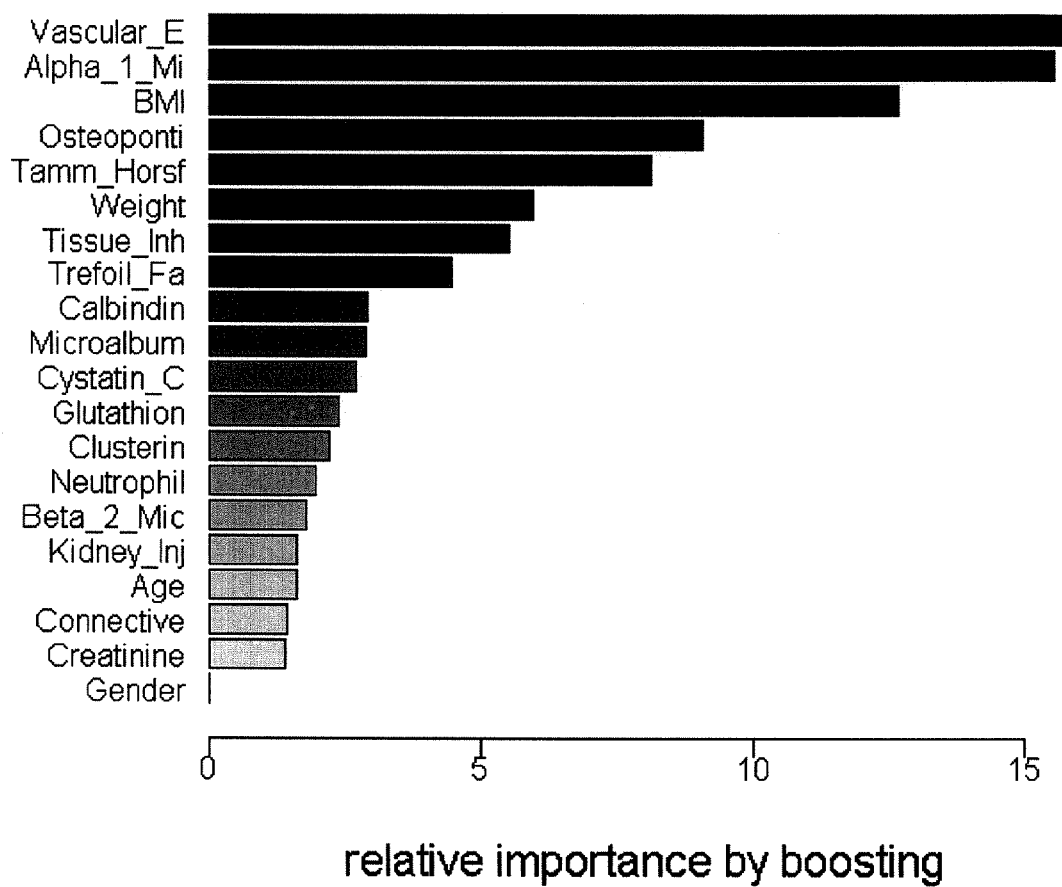

The average relative importance of 16 different analytes (alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF) and 4 different clinical variables (weight, BMI, age, and gender) from 100 runs were analyzed with two different statistical methods—random forest (plasma and urine samples) and boosting (urine samples)—for each of the following comparisons: disease (AA+GN+OU+DN) vs. normal (FIG. 5, Table 12), OU vs. normal (FIG. 7, Table 14), OU vs. AA (FIG. 9, Table 16), OU vs. GN (FIG. 11, Table 18), and OU vs. DN (FIG. 13, Table 20).

TABLE 11 disease v. NL

| method | Mean AUROC | Standard deviation AUROC |
|---|---|---|
| random forest | 0.931 | 0.039 |
| bagging | 0.919 | 0.045 |
| svm | 0.915 | 0.032 |
| boosting | 0.911 | 0.06 |
| lasso | 0.897 | 0.044 |
| logistic regression | 0.891 | 0.041 |
| ctree | 0.847 | 0.046 |
| cart | 0.842 | 0.032 |
| matt | 0.83 | 0.023 |

TABLE 12 disease v. NL

| analyte | relative importance |
|---|---|
| Creatinine | 11.606 |
| Kidney_Injury_M | 8.486 |
| Tamm_Horsfall_P | 8.191 |
| Total_Protein | 6.928 |
| Osteopontin | 6.798 |
| Neutrophil_Gela | 6.784 |
| Tissue_Inhibito | 6.765 |
| Vascular_Endoth | 6.716 |
| Trefoil_Factor_ | 6.703 |
| Cystatin_C | 6.482 |
| Alpha_1_Microgl | 6.418 |
| Beta_2_Microglo | 6.228 |
| Glutathione_S_T | 6.053 |
| clusterin | 5.842 |

TABLE 13

OU v. NL

| method | Mean AUROC | Standard deviation of AUROC |
|---|---|---|
| cart | 1 | 0 |
| bagging | 1 | 0 |
| boosting | 1 | 0 |
| random forest | 1 | 0.003 |
| lasso | 0.997 | 0.012 |
| ctree | 0.991 | 0.048 |
| svm | 0.917 | 0.079 |
| logistic regression | 0.911 | 0.099 |
| matt | 0.853 | 0.107 |

TABLE 14

OU v. NL

| analyte | |
|---|---|
| Creatinine | 19.055 |
| Tamm_Horsfall_P | 7.682 |

TABLE 14-continued

OU v. NL

| analyte | |
|---|---|
| Alpha_1_Microgl | 7.664 |
| clusterin | 6.863 |
| Neutrophil_Gela | 6.825 |
| Osteopontin | 6.517 |
| Kidney_Injury_M | 6.156 |
| Total_Protein | 6.021 |
| Vascular_Endoth | 5.971 |
| Tissue_Inhibito | 5.941 |
| Trefoil_Factor_ | 5.779 |
| Cystatin_C | 5.683 |
| Glutathione_S_T | 5.097 |
| Beta_2_Microglo | 4.746 |

TABLE 15

OU v. AA

| method | Mean AUROC | Standard deviation of AUROC |
|---|---|---|
| random forest | 0.814 | 0.11 |
| bagging | 0.792 | 0.115 |
| svm | 0.788 | 0.112 |
| lasso | 0.786 | 0.118 |
| boosting | 0.757 | 0.117 |
| matt | 0.687 | 0.111 |
| logistic regression | 0.683 | 0.116 |
| cart | 0.665 | 0.097 |
| ctree | 0.659 | 0.118 |

TABLE 16

OU v. AA

| analyte | Relative importance |
|---|---|
| Total_Protein | 11.502 |
| Tissue_Inhibito | 9.736 |
| Cystatin_C | 9.161 |
| Alpha_1_Microgl | 8.637 |
| Trefoil_Factor_ | 7.329 |
| Osteopontin | 7.326 |
| Beta_2_Microglo | 6.978 |
| Neutrophil_Gela | 6.577 |
| Glutathione_S_T | 6.100 |
| Tamm_Horsfall_P | 6.066 |
| Kidney_Injury_M | 6.038 |
| Vascular_Endoth | 5.946 |
| clusterin | 4.751 |
| Creatinine | 3.854 |

TABLE 17

OU v. GN

| method | Mean AUROC | Standard deviation of AUROC |
|---|---|---|
| random forest | 0.946 | 0.061 |
| boosting | 0.941 | 0.071 |
| bagging | 0.933 | 0.078 |

TABLE 17-continued

OU v. GN

| method | Mean AUROC | Standard deviation of AUROC |
|---|---|---|
| svm | 0.932 | 0.07 |
| lasso | 0.888 | 0.092 |
| cart | 0.879 | 0.091 |
| ctree | 0.879 | 0.104 |
| matt | 0.872 | 0.099 |
| logistic regression | 0.869 | 0.134 |

TABLE 18

OU v. GN

| analyte | Relative importance |
|---|---|
| Total_Protein | 14.391 |
| Alpha_1_Microgl | 11.033 |
| Kidney_Injury_M | 8.453 |
| Tissue_Inhibito | 7.934 |
| Creatinine | 7.714 |
| clusterin | 7.353 |
| Osteopontin | 7.123 |
| Vascular_Endoth | 6.321 |
| Neutrophil_Gela | 6.244 |
| Cystatin_C | 5.632 |
| Beta_2_Microglo | 4.962 |
| Tamm_Horsfall_P | 4.829 |
| Trefoil_Factor_ | 4.594 |
| Glutathione_S_T | 3.418 |

TABLE 19

DN v. OU

| method | mean_AUROC | std_AUROC |
|---|---|---|
| lasso | 0.993 | 0.019 |
| random forest | 0.986 | 0.027 |
| boosting | 0.986 | 0.027 |
| bagging | 0.977 | 0.04 |
| cart | 0.962 | 0.045 |
| ctree | 0.954 | 0.05 |
| svm | 0.95 | 0.059 |
| logistic regression | 0.868 | 0.122 |
| matt | 0.862 | 0.111 |

TABLE 20

DN v. OU

| analyte | Relative importance |
|---|---|
| Creatinine | 18.278 |
| Alpha_1_Microgl | 9.808 |
| clusterin | 9.002 |
| Beta_2_Microglo | 8.140 |
| Cystatin_C | 7.101 |
| Osteopontin | 6.775 |
| Glutathione_S_T | 5.731 |
| Neutrophil_Gela | 5.720 |
| Trefoil_Factor_ | 5.290 |
| Kidney_Injury_M | 5.031 |
| Total_Protein | 5.030 |

TABLE 20-continued

DN v. OU

| analyte | Relative importance |
|---|---|
| Vascular_Endoth | 4.868 |
| Tissue_Inhibito | 4.615 |
| Tamm_Horsfall_P | 4.611 |

It should be appreciated by those of skill in the art that the techniques disclosed in the examples above represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

What is claimed is:

1. A method for diagnosing, monitoring, or determining obstructive uropathy in a mammal, the method comprising:
   a. providing a test sample comprising a sample of bodily fluid taken from the mammal;
   b. determining sample concentrations for sample analytes in the test sample, wherein the sample analytes are creatinine, THP, A1M (alpha-1 microglobulin), clusterin, NGAL, and osteopontin;
   c. comparing the combination of sample concentrations to a data set comprising at least one entry, wherein each entry of the data set comprises a list comprising three or more corresponding minimum diagnostic concentrations indicative of obstructive uropathy, wherein each minimum diagnostic concentration comprises a maximum of a range of analyte concentrations for a healthy mammal;
   d. determining a matching entry of the dataset in which all minimum diagnostic concentrations are less than the corresponding sample concentrations; and,
   e. identifying an indicated disorder comprising the particular disorder of the matching entry.

2. A method for diagnosing, monitoring, or determining obstructive uropathy in a mammal, the method comprising:
   a. providing a test sample comprising a sample of bodily fluid taken from the mammal;
   b. determining a combination of sample concentrations for three or more sample analytes in the test sample, wherein the sample analytes are selected from the group consisting of alpha-1 microglobulin, beta-2 microglobulin, calbindin, clusterin, CTGF, creatinine, cystatin C, GSTalpha, KIM-1, microalbumin, NGAL, osteopontin, THP, TIMP-1, TFF-3, and VEGF;
   c. comparing the combination of sample concentrations to a data set comprising at least one entry, wherein each entry of the data set comprises a list comprising three or more corresponding minimum diagnostic concentrations indicative of obstructive uropathy, wherein each minimum diagnostic concentration comprises a maximum of a range of analyte concentrations for a healthy mammal;
   d. determining a matching entry of the dataset in which all minimum diagnostic concentrations are less than the corresponding sample concentrations; and,
   e. identifying an indicated disorder comprising the particular disorder of the matching entry.

3. The method of claim 2, wherein the mammal is selected from the group consisting of humans, apes, monkeys, rats, mice, dogs, cats, pigs, and livestock including cattle and oxen.

4. The method of claim 2, wherein the bodily fluid is selected from the group consisting of urine, blood, plasma, serum, saliva, semen, and tissue lysates.

5. The method of claim 2, wherein the minimum diagnostic concentration in human plasma of alpha-1 microglobulin is about 16 µg/ml, beta-2 microglobulin is about 2.2 µg/ml, calbindin is greater than about 5 ng/ml, clusterin is about 134 µg/ml, CTGF is about 16 ng/ml, cystatin C is about 1170 ng/ml, GST-alpha is about 62 ng/ml, KIM-1 is about 0.57 ng/ml, NGAL is about 375 ng/ml, osteopontin is about 25 ng/ml, THP is about 0.052 µg/ml, TIMP-1 is about 131 ng/ml, TFF-3 is about 0.49 µg/ml, and VEGF is about 855 pg/ml.

6. The method of claim 2, wherein the minimum diagnostic concentration in human sera of alpha-1 microglobulin is about 17 µg/ml, beta-2 microglobulin is about 2.6 µg/ml, calbindin is greater than about 2.6 ng/ml, clusterin is about 152 µg/ml, CTGF is greater than about 8.2 ng/ml, cystatin C is about 1250 ng/ml, GST-alpha is about 52 ng/ml, KIM-1 is greater than about 0.35 ng/ml, NGAL is about 822 ng/ml, osteopontin is about 12 ng/ml, THP is about 0.053 µg/ml, TIMP-1 is about 246 ng/ml, TFF-3 is about 0.17 µg/ml, and VEGF is about 1630 pg/ml.

7. The method of claim 2, wherein the minimum diagnostic concentration in human urine of alpha-1 microglobulin is about 233 µg/ml, beta-2 microglobulin is greater than about 0.17 µg/ml, calbindin is about 233 ng/ml, clusterin is greater than about 0.089 µg/ml, CTGF is greater than about 0.90 ng/ml, cystatin C is about 1170 ng/ml, GST-alpha is greater than about 26 ng/ml, KIM-1 is about 0.67 ng/ml, NGAL is about 81 ng/ml, osteopontin is about 6130 ng/ml, THP is about 2.6 µg/ml, TIMP-1 is greater than about 3.9 ng/ml, TFF-3 is greater than about 2 µg/ml, and VEGF is about 517 pg/ml.

8. The method of claim 2, wherein a combination of sample concentrations for six or more sample analytes in the test sample are determined.

9. The method of claim 8, wherein sample concentrations are determined for the analytes selected from the group consisting of alpha-1 microglobulin, beta-2 microglobulin, cystatin C, KIM-1, THP, and TIMP-1.

10. The method of claim 2, wherein a combination of sample concentrations for said sixteen sample analytes in the test sample are determined.

11. A method for diagnosing, monitoring, or determining obstructive uropathy in a mammal, the method comprising:
a. providing a test sample comprising a sample of bodily fluid taken from the mammal;
b. determining the concentrations of three or more sample analytes in a panel of biomarkers in the test sample, wherein the sample analytes are selected from the group consisting of alpha-1 microglobulin, beta-2 microglobulin, calbindin, clusterin, CTGF, creatinine, cystatin C, GSTalpha, KIM-1, microalbumin, NGAL, osteopontin, THP, TIMP-1, TFF-3, and VEGF;
c. identifying diagnostic analytes in the test sample, wherein the diagnostic analytes are the sample analytes whose concentrations are statistically different from concentrations found in a control group of humans who do not suffer from obstructive uropathy;
d. comparing the combination of diagnostic analyte concentrations to a dataset comprising at least one entry, wherein each entry of the dataset comprises a combination of three or more diagnostic analyte concentrations as in step b reflective of obstructive uropathy; and,
e. identifying the particular disorder having the combination of diagnostic analyte concentrations that essentially match the combination of sample analytes.

12. The method of claim 11, wherein the mammal is selected from the group consisting of humans, apes, monkeys, rats, mice, dogs, cats, pigs, and livestock including cattle and oxen.

13. The method of claim 11, wherein the bodily fluid is selected from the group consisting of urine, blood, plasma, serum, saliva, semen, and tissue lysates.

14. The method of claim 11, wherein the test sample is plasma and the diagnostic analytes comprise creatinine, KIM-1 and THP or creatinine, THP, and AIM.

15. The method of claim 11, wherein the test sample is urine and the diagnostic analytes comprise microalbumin, creatinine, and KIM-1 or microalbumin, TIMP-1, and osteopontin.

16. The method of claim 11, wherein the test sample is urine and the diagnostic analytes comprise creatinine, THP, A1M, clusterin, NGAL, and osteopontin.

17. A method for diagnosing, monitoring, or determining obstructive uropathy in a mammal, the method comprising:
a. providing an analyte concentration measurement device comprising three or more detection antibodies, wherein each detection antibody comprises an antibody coupled to an indicator, wherein the antigenic determinants of the antibodies are sample analytes associated with obstructive uropathy, and wherein the sample analytes are selected from the group consisting of alpha-1 microglobulin, beta-2 microglobulin, calbindin, clusterin, CTGF, creatinine, cystatin C, GST-alpha, KIM-1, microalbumin, NGAL, osteopontin, THP, TIMP-1, TFF-3, and VEGF;
b. providing a test sample comprising three or more sample analytes and a bodily fluid taken from the mammal;
c. contacting the test sample with the detection antibodies and allowing the detection antibodies to bind to the sample analytes;
d. determining the concentrations of the sample analytes by detecting the indicators of the detection antibodies bound to the sample analytes in the test sample, thereby providing a combination of sample concentrations;
e. comparing the combination of sample concentrations to a corresponding combination of minimum diagnostic concentration reflective of obstructive uropathy;
f. identifying an indicated obstructive uropathy comprising the particular disorder of the matching entry.

18. The method of claim 17, wherein the bodily fluid is selected from the group consisting of urine, blood, plasma, serum, saliva, semen, and tissue lysates.

19. The method of claim 17, wherein the analyte concentration measurement device comprises six or more detection antibodies.

20. The method claim 17, wherein the analyte concentration measurement device comprises sixteen detection antibodies.

21. The method of claim 16, wherein the sample analytes are selected from the group consisting of alpha-1 microglobulin, beta-2 microglobulin, cystatin C, KIM-1, THP, and TIMP-1.

22. The method of claim 17, wherein the sample analytes are selected from the group consisting of creatinine, THP, A1M, clusterin, NGAL, and osteopontin.

* * * * *

UNITED STATES PATENT AND TRADEMARK OFFICE
CERTIFICATE OF CORRECTION

PATENT NO. : 8,735,080 B2
APPLICATION NO. : 12/852236
DATED : May 27, 2014
INVENTOR(S) : LaBrie et al.

Page 1 of 1

It is certified that error appears in the above-identified patent and that said Letters Patent is hereby corrected as shown below:

On the Title Page Foreign reference WO 2008109797, change "06/2008" to "09/2008"

On the Title Page Foreign reference WO 2008109797, delete entire reference "WO 2008109797 03/2008"

On the Title Page Other publication, change "TROF et al., "BIOMARKERS OF ACUTE RENAL INJURY AND RENAL FAILURE." Shock [online], September 2006 [Retrieved on 2010-09-29], Vol. 26, No. 3, pp. 245-253, Retrieved from the Internet: <URL: http://journals.www.com/shockjournal/Fulltext/2006/09000/Biomarkers_of Acute_Renal_Injury_and_Renal.Failure.4.aspx>." to ""TROF et al., "BIOMARKERS OF ACUTE RENAL INJURY AND RENAL FAILURE." Shock [online], September 2006 [Retrieved on 2010-09-29], Vol. 26, No. 3, pp. 245-253, Retrieved from the Internet: <URL: http://journals.lww.com/shockjournal/Fulltext/2006/09000/Biomarkers_of Acute_Renal_Injury_and_Renal_Failure.4.aspx>."

On Title Page 2 Other publication, change "RODRIGO et al., Circulating levels of matrix metalloproteinases MMP-3 and MMP-2 in renal transplant rebipients with chronic transplant nephropathy. Nephrol. Dial. Transplant. December 2000 (12.2000), Vol. 15, No. 12, pages 2041-2045." to "RODRIGO et al., Circulating levels of matrix metalloproteinases MMP-3 and MMP-2 in renal transplant recipients with chronic transplant nephropathy. Nephrol. Dial. Transplant December 2000 (12.2000), Vol. 15, No. 12, pages 2041-2045."

In the Claims

Col. 45 claim 7, line 36, change "2" to "21"

Col. 46 claim 14, line 15, change "AIM" to "A1M"

Col. 46 claim 21, line 59, change "16" to "17"

Signed and Sealed this
Fifth Day of August, 2014

Michelle K. Lee
*Deputy Director of the United States Patent and Trademark Office*